United States Patent
Stilz et al.

(10) Patent No.: US 6,365,572 B1
(45) Date of Patent: Apr. 2, 2002

(54) LOW MOLECULAR WEIGHT PEPTIDE DERIVATIVES AS INHIBITORS OF THE LAMININ/NIDOGEN INTERACTION

(75) Inventors: Hans Ulrich Stilz, Frankfurt; Martin Gerl, Niedernhausen, both of (DE); Gary A. Flynn, Tucson, AZ (US); Magda Stankova, Tucson, AZ (US); Robert A. Binnie, Tucson, AZ (US)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/517,123

(22) Filed: Feb. 29, 2000

(30) Foreign Application Priority Data

Mar. 1, 1999 (EP) .............................. 99103869

(51) Int. Cl.[7] ........................ A61K 38/06; A61K 38/07; A61K 38/08; C07K 5/10; C07K 7/06
(52) U.S. Cl. ........................... 514/17; 436/87; 436/501; 514/18; 530/329; 530/330; 530/331
(58) Field of Search .................. 424/9.1, 9.2; 436/501, 436/503, 504, 87; 514/17, 18, 19, 20; 530/329, 330, 331

(56) References Cited

U.S. PATENT DOCUMENTS 5,493,008 A   2/1996   Fox et al. .................... 530/326

FOREIGN PATENT DOCUMENTS

WO   98/31709   7/1998

OTHER PUBLICATIONS

Yanaihara et al. Synthetic Study on Human C–Peptide . . . Hoppe–Seyler's Z. Physiol. Chem. vol. 362, pp. 775–797, Jun. 19, 1981.*

Zhang, X. et al., "A non–mammalian in vivo model for cellular and molecular analysis of glucose–mediated thickening of basement membranes", Diabetologia, vol. 33, pp. 704–707, (1990).

Wilson, R. et al., "2.2 Mb of contiguous nucleotide sequence from Chromosome III of C. elegans", Nature, vol. 368, pp. 32–38, (1994).

Veber, D. et al. "The design of metabolically–stable peptide analogs", Trends Neurosci., vol. 8, pp. 392–396, (1985).

Stetefeld, J. et al., "Crystal Structure of Three Consecutive Laminin–type Epidermal Growth Factor–like (LE) Modules of Laminin γ 1 Chain Harboring the Nidogen Binding Site", J. Mol. Biol., vol. 257, pp. 644–657.

Smola, H. et al., "Dynamics of Basement Membrane Fromation by Keratinocyte–Fibroblast Interactions in Organotypic Skin Culture", Experimental Cell Research, vol. 239, pp. 399–410, (1998).

Nicosia, R. et al., "Growth of Microvessels in Serum–Free Matrix Culture of Rat Aorta", Laboratory Investigation, vol. 63, No. 1, pp. 115–122, (1990).

Pöschl, E. et al., "Site–directed mutagenesis and structural interpretation of the nidogen binding site of the laminin γ 1 chain", The EMBO Journal, vol. 15, No. 19, pp. 5154–5159 (1996).

Pöschl, E. et al., "Two non–contiguous regions contribute to nidogen binding to a single EGF–like motif of the laminin γ 1 chain", The EMBO Journal, vol. 13, No. 16, pp. 3741–3747, (1994).

(List continued on next page.)

Primary Examiner—Jeffrey E. Russel
(74) Attorney, Agent, or Firm—Finnegan, Henderson, Farabow, Garrett & Dunner, LLP

(57) ABSTRACT

Low molecular weight peptide derivatives which are able to act as inhibitors of the interaction between laminin and nidogen (laminin/nidogen interaction), a process for their preparation, pharmaceutical compositions prepared therefrom and their use for preparing pharmaceuticals and for identifying inhibitors of the laminin/nidogen interaction.

34 Claims, 12 Drawing Sheets

OTHER PUBLICATIONS

Pikkarainen, T. et al., "Human Laminim B2 Chain", The Journal of Biological Chemistry, vol. 263, No. 14, pp. 6751–6758 (1988).

O'Reilly, M. et al., "Treatment of Murine Hemangioendotheliomas With the Angiogenesis Inhibitor AGM–1470", Journal of Pediatric Surgery, vol. 30, No. 2, pp. 325–330, (1995).

Nehls, V. et al., "A Novel, Microcarrier–Based in Vitro Assay for Rapid and Reliable Quantification of Three–Dimensional Cell Migration and Angiogenesis", Microvascular Research, vol. 50, pp. 311–322, (1995).

Milner–White, E.J., "Predicting the biologically active conformations of short polypeptides", Trends Pharmacol. Sci., vol. 10, pp. 70–74, (1989).

Mayer, U. et al., "A single EGF–like motif of laminin is responsible for high affinity nidogen binding", The EMBO Journal vol. 12, pp. 1879–1885, (1993).

Mann, K. et al., "Characterization of proteolytic fragments of the laminin–nidogen complex and their activity in ligand–binding assays", Eur. J. Biochem, vol. 178, pp. 71–80, (1988).

Lebl, M. et al., "Screening of Completely Random OneBead One–Peptide Libraries for Activities in Solution", A Companion to Methods in Enzymology, vol. 6, pp. 381–387, (1994).

Lam, K. et al., "A new type of synthetic peptide library for identifying ligand–binding activity", Nature, vol. 354, pp. 82–84, (1991).

Krchñák, V. et al., "Noninvasive Continuous Monitoring of Solid–Phase Peptide Synthesis by Acid–Base Indicator", Collection Czechoslovak Chem. Commun., vol. 53, pp. 2542–2548, (1988).

Kočiš, P. et al., "Symmetrical Structure Allowing the Selective Multiple Release of a Defined Quantity of Peptide from a Single Bead of Polymeric Support", Tetrahedron Letters, vol. 34, No. 45, pp. 7251–7252, (1993).

Kadoya, Y. et al., "Importance of nidogen binding to laminin γ 1 for branching epithelial morphogenesis of the submandibular gland", Development 124, pp. 683–691, (1997).

Kaiser, E. et al., "Color Test for Detection of Free Terminal Amino Groups in the Solid–Phase Synthesis of Peptides", Anal. Biochem., vol. 34, pp. 595–598 (1969).

Jain, R. et al., "Quantitative angiogenesis assays: Progress and problems", Nature Medicine, vol. 3, No. 11, pp. 1203–1208, (1997).

Hruby, V.J., "Peptide chemistry: Designing peptides pseudopeptides and peptidomimetics for biological receptors", Petides, Proc. 13th American Petide Symposium, ESCOM, pp. 3–17, (1994).

Grobstein, C., "Trans–Filter Induction of Tubules in Mouse Metanephrogenic Mesenchyme", Experimental Cell Research, vol. 10, pp. 424–440, (1956).

Grobstein, C., "Epithelio–Mesenchymal Specificity in the Morphogenesis of Mouse Sub–Mandibular Rudiments in Vitro", J. Exp. Zool, vol. 124, pp. 383–413, (1953).

Gerl, M. et al., "Localization of a major nidogen–binding site to domain III of laminin B2 chain", Eur. J. Biochem, vol. 202, pp. 167–174, (1991).

Furka, A. et al., "General method for rapid synthesis of multicomponent peptide mixtures", Int. J. Peptide Protein, Res., vol. 37, pp. 487–493, (1991).

Engel, J., "EGF–like domains in extracellular matrix proteins: localized signals for growth differentiation?", FEBS Letters, vol. 251, No. 1, 2, pp. 1–7, (1989).

Ekblom, P. et al., "Role of mesenchymal nidogen for epithelial morphogenesis in vitro", Development, vol. 120, pp. 2003–2014, (1994).

Chi, H. et al., "Primary Structure of the Drosophila Laminin B2 Chain and comparison with Human, Mouse, and Drosophila Laminin B1 and B2 Chains", The Journal of Biological Chemistry, vol. 264, No. 3, pp. 1543–1550, (1989).

Burgeson, R. et al., "A New Nomenclature for the Laminins", Matrix Biology, vol. 14, pp. 209–211, (1994).

Baumgartner, R. et al., "Structure of the Nidogen Binding LE Module of the Lamin γ 1 Chain in Solution", J. Mol. Biol., vol. 257, pp. 658–668, (1996).

Fox, J. et al., "Recombinant nidogen consists of three globular domains and mediates binding of laminin to collagen type IV", The EMBO Journal, vol. 10, No. 11, pp. 3137–3146, (1991).

Adams, J. et al., "Regulation of development and differentiation by the extracellular matrix", Development 117, pp. 1183–1198, (1993).

* cited by examiner

Compound 1 (Control) (SEQ ID NO:8)

Compound 2 (Control) (SEQ ID NO:9)

Compound 3 (SEQ ID NO:10)

Compound 4 (SEQ ID NO:11)

Compound 5 (SEQ ID NO:12)

Compound 6 (SEQ ID NO:13)

Compound 7 (SEQ ID NO:14)

Compound 8 (SEQ ID NO:15)

Compound 9 (SEQ ID NO:16)

Compound 10 (SEQ ID NO:17)

Compound 11 (SEQ ID NO:18)

Compound 12 (SEQ ID NO:19)

Compound 13 (SEQ ID NO:20)

Compound 14 (SEQ ID NO:21)

Compound 15 (SEQ ID NO:22)

Compound 16 (SEQ ID NO:23)

Compound 17 (SED ID NO:24)

Compound 18 (SEQ ID NO:25)

Compound 19 (SEQ ID NO:26)

Compound 20 (SEQ ID NO:27)

Compound 21 (SEQ ID NO:28)

Compound 22 (SEQ ID NO:29)

Compound 23 (SEQ ID NO:30)

Compound 24 (SEQ ID NO:31)

Compound 25 (SEQ ID NO:32)

Compound 26 (SEQ ID NO:33)

Compound 27 (SEQ ID NO:34)

Compound 28 (SEQ ID NO:35)

Compound 29 (SEQ ID NO:36)

Compound 30 (SEQ ID NO:37)

Compound 31 (SEQ ID NO:38)

Compound 32 (SEQ ID NO:39)

Compound 33 (SEQ ID NO:40)

Compound 34 (SEQ ID NO:41)

Compound 35 (SEQ ID NO:42)

Compound 36 (SEQ ID NO:43)

Compound 37 (SEQ ID NO:44)

Compound 38 (SEQ ID NO:45)

Compound 39 (SEQ ID NO:46)

Compound 40 (SEQ ID NO:47)

Compound 41 (SEQ ID NO:48)

Compound 42 (SEQ ID NO:49)

Compound 43 (SEQ ID NO:50)

LOW MOLECULAR WEIGHT PEPTIDE DERIVATIVES AS INHIBITORS OF THE LAMININ/NIDOGEN INTERACTION

This application claims the benefit of foreign priority to European Application No. 99103869.6, filed on Mar. 1, 1999. This European priority document is incorporated by reference herein.

Objects of the present invention are low molecular weight peptide derivatives which are able to act as inhibitors of the interaction between laminin and nidogen (laminin/nidogen interaction), a process for their preparation, pharmaceutical compositions prepared therefrom and their use for preparing pharmaceuticals and for identifying inhibitors of the laminin/nidogen interaction.

The association of laminin (an 800 kDa glycoprotein) and nidogen (a 160 kDa glycoprotein) is regarded as a crucial biomolecular mechanism in the synthesis and stabilization of basement membranes (Mayer, U. and Timpl, R. (1994) in: Extracellular Matrix Assembly and Structure (P. D. Yurchenco, D. Birk and R. P. Mecham, Ed.) S. 389–416, Academic Press, Orlando, Fla.). The ability of nidogen to form ternary complexes with all main constituents of the basement membrane such as, for example, γ1-containing laminin isoforms (for nomenclature see: Burgeson, R. E.; Chiquet, M.; Deutzmann, R.; Ekblom, P.; Engel, J.; Kleinmann, H.; Martin, G. R.; Meneguzzi, G.; Paulsson M.; Sanes, J.; Timpl, R.; Tryggvasson, K.; Yamada, Y.; Yurchenco, P. D. (1994) Matrix Biology 14; 209–211), collagen IV, perlecan and fibulin, and the association structures of each of them, means that it assumes the function of a linker which connects together, spatially organizes and stabilizes the independent macrostructures (Fox, J. W.; Mayer, U.; Nischt, R.; Aumailley, M.; Reinhardt, D.; Wiedemann, H.; Mann, K.; Timpl, R.; Krieg, T., Engel, J.; and Chu, M.-L. (1991) EMBO J. 10, 3137–3146).

Basement membranes are highly specialized extracellular structures which are attributed with important functions in the control of cell and tissue functions, tissue architecture, tissue interactions, cell growth, cell transformation, cell migration and in tissue-specific gene expression (Adams, J. C. and Waft, F. M. (1993) Development 117, 1183–1198).

Experiments with polyclonal antilaminin antibodies have provided clear evidence of the central function of the laminin/nidogen interaction in the synthesis of a functional basement membrane. The described antibodies were obtained by immunizing rabbits with laminin P1 or with the recombinantly produced nidogen-binding domain of laminin (γ1 III 3–5). The antibodies concentrated by affinity chromatography on laminin P1 or laminin γ1 III 3–5 matrices showed complete inhibition of the laminin/nidogen association in inhibition assays. However, this is based on steric blockade of the access of nidogen to laminin by the antibodies, whose binding regions are located in the vicinity of the nidogen-binding sequences of laminin (Mayer, U.; Nischt, R.; Pöschl, E.; Mann, K.; Fukuda, K.; Gerl, M.; Yamada, Y.; Timpl, R. (1993) EMBO J. 12; 1879–1885).

In embryonic organ cultures, the described antibodies inhibited both the development of renal tubules, the formation of pulmonary alveoli and the morphogenesis of the embryonic salivary gland. These three models are representative of ontogenesis programs which depend on unimpeded synthesis of new basement membrane (Ekblom, P.; Ekblom, M.; Fecker, L.; Klein, G.; Zhang, H.-Y.; Kadoya, Y.; Chu, M.-L.; Mayer, U.; Timpl, R. (1994) Development 120; 2003–2014).

Antibodies directed against the laminin γ1 chain sequence region which is essential for nidogen binding are likewise able to inhibit the laminin/nidogen association. The inhibition is, however, competitive, in contrast to the antilaminin antibodies described above, because they compete directly with the nidogen for the binding site on laminin (WO 98/31709).

A monoclonal antibody of the IgM subclass (antilaminin P1 A6/2/4-DSM ACC2327; see WO 98/31709) inhibits the laminin/nidogen interaction in vitro with an IC50 of 30 nM. Like the polyclonal antilaminin antibody preparation described above, it prevents the morphogenesis of the embryonic salivary gland in organ culture. This underlines the specificity of the laminin/nidogen interaction, and the importance of the LE-4 module and of the identified sequence region in the laminin γ1 III 4 domain in this interaction.

The nidogen binding domain of laminin has been unambiguously identified and characterized in terms of its location, sequence and its spatial structure (X-ray crystal structure and NMR structure) (Gerl, M.; Mann, K.; Aumailley, M.; Timpl, R. (1991) Eur. J. Biochem. 202; 167–174. Mayer, U.; Nischt, R.; Pöschl, E.; Mann, K.; Fukuda, K.; Gerl, M.; Yamada, Y.; Timpl, R. (1993) EMBO J. 12; 1879–1885. Baumgartner, R.; Czisch, M.; Mayer, U.; Pöschl, E.; Huber, R.; Timpl, R.; Holak, T. A. (1996) J. Mol. Biol. 257; 658–668. Stetefeld, J.; Mayer, U.; Timpl, R.; Huber, R. (1996) J. Mol. Biol. 257; 644–657). It is located in an "LE module" (laminin type epidermal growth factor-like) of the short arm of the γ1 chain of laminin, in the domain γ1 III 4. "LE modules" are structural motifs of 50–60 amino acids which have a complex folding pattern, analogous to EGF, with 4 disulfide bridges (Bairoch, A.; (1995) Nomenclature of extracellular domains. The SWISS-PROT Protein sequence data bank. release 310. Engel, J. (1989) FEBS Letters 251; 1–7).

High-affinity binding of nidogen to the complementary laminin domain has been detected for laminin P1 from the EHS tumor of mice, laminin 2 and laminin 4 from human placenta and laminin from drosophila. The cause of this species-overlapping binding specificity is the extremely large identity of sequences present in the γ1 III 4 domain for the species investigated. It is 97% between human and mouse, 61% between mouse and drosophila and, astonishingly, 51% between mouse and Caenorhabditis elegans when the whole domain is taken into account (Pikkarinen, T.; Kallunki, T.; Tryggvasson, K. (1987) J. Biol. Chem. 263; 6751–6758. Chi, H.-C.; Hui, C.-F. (1989) J. Biol. Chem. 264; 1543–1550. Wilson, R. et al.(1994) Nature 368: 32–38. Pöschl, E.; Mayer, U.; Stetefeld, J.; Baumgartner, R.; Holak, T. A.; Huber, R.; Timpl, R. (1996) EMBO J. 15: 5154–5159).

Besides the dependency of nidogen binding on an intact three-dimensional structure, unambiguous sequence regions located in the S—S stabilized loops a and c of the domain γ1 III 4 have been identified. Five essential amino acids have been identified, four located inside a section of 7 amino acids in loop a, and a tyrosine side-chain in loop c (Mann, K.; Deutzmann, R.; Timpl, R. (1988) Eur. J. Biochem. 178; 71–80).

Synthetic peptides which can be derived from the appropriate regions of the γ1 III 4 domain and are able to inhibit completely the laminin/nidogen binding in specific binding assays have been disclosed by J. W. Fox and R. Timpl (U.S. Pat. No. 5,493,008).

The high-affinity binding to the laminin binding site of nidogen is thought to require an interaction with a tyrosine or histidine from a loop (loop c) adjacent to the actual binding sequence. This aromatic interaction was postulated as a precondition for inhibition in the IC50 range <500 nM on the basis of the 3D structure of the laminin γ1 III 3–5 and as a result of the structure/function relations described in the U.S. Pat. No. 5,493,008. The question of whether loop c interacts directly with the nidogen, or whether it makes a contribution to stabilizing the suitable spatial structure of the NIDPNAV (SEQ ID NO:1) sequence region remained unclarified, however (Pöschl, E.; Fox, J. W.; Block, D.; Mayer, U.; Timpl, R, (1994) EMBO J. 13; 3741–3747. Baumgartner, R.; Czisch, M.; Mayer, U.; Pöschl, E.; Huber, R.; Timpl, R.; Holak, T. A. (1996) J. Mol. Biol. 257; 658–668. Stetefeld, J.; Mayer, U.; Timpl, R.; Huber, R. (1996) J. Mol. Biol. 257; 644–657).

The laminin/nidogen interaction is influenced by a strong conformational component (Mayer, U.; Nischt, R.; Pöschl, E.; Mann, K.; Fukuda, K.; Gerl, M.; Yamada, Y.; Timpl, R. (1993) EMBO J. 12; 1879–1885. Mann, K.; Deutzmann, R.; Timpl, R. (1988) Eur. J. Biochem. 178; 71–80). The synthetic peptides which can be derived from the nidogen binding site of laminin are not able to form a disulfide linkage pattern as is present in LE modules, but they show an activity in inhibition assays which is about 400–10,000-fold weaker than that of intact laminin P1 or laminin γ1 III 3–5 (Pöschl, E.; Fox, J. W.; Block, D., Mayer, U.; Timpl, R, (1994) EMBO J. 13; 3741–3747. J. W. Fox and R. Timpl; U.S. Pat. No. 5,493,008). This decline in activity is not unusual, since it is known that peptides may assume a myriad of different conformations in aqueous solution and that only a certain percentage of peptides is to be found in the biologically active conformation. The most active peptide described to date (IC50 of 22 nM) has a molecular weight of about 2700 Da (≅about 50% of an LE module). It comprises an intact S—S loop which presumably stabilizes the structure of the essential NIDPNAV (SEQ ID NO:1) sequence region (Pöschl, E.; Fox, J. W.; Block, D.; Mayer, U.; Timpl, R, (1994) EMBO J. 13; 3741–3747. J. W. Fox and R. Timpl; U.S. Pat. No. 5,493,008).

The chemical formula of the sequence NIDPNAV (Asn-Iie-Asp-Pro-Asn-Ala-Val) (SEQ ID NO:1) is as follows:

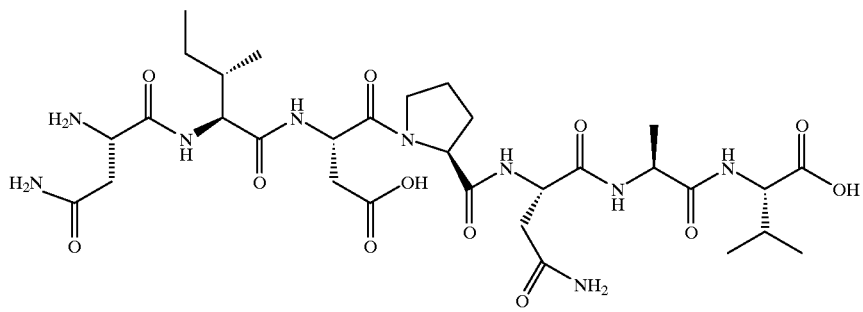

Inhibitors of the laminin/nidogen interaction should be suitable for preparing pharmaceuticals for diseases which are related to an increased or unwanted synthesis of basement membranes.

Such diseases are e.g. all types of late complications of diabetes which are accompanied by thickening of basement membranes (especially in the kidney, eye, vascular system), hepatic fibrosis, especially alcoholic hepatic fibrosis, characterized by synthesis of a continuous basement membrane in the sinusoids and a capillarization caused thereby, all fibroses (chronic or iatrogenic) in which an increased synthesis of basement membrane or components of the basement membrane can be observed (kidney, lung, skin), atherosclerosis characterized by a limitation of the regulation of lipid metabolism, which may be caused inter alia by impaired filtration of lipoproteins through the partly capillarized liver sinusoids (the pathological changes in the vascular system which can be observed with atherosclerosis may also in part be attributed to modifications of the composition and structure of the basement membranes in the vessels), diseases in which angiogenesis contributes to a deterioration in the clinical picture, for example cancers in which neovascularization is required for tumor growth, diabetic retinopathy, retrolental fibroplasia, disorders with a strong inflammatory component (for example rheumatoid arthritis, osteoarthritis, vasculitis), hemangiomas, psoriasis, and many others.

The use of peptides like those described in U.S. Pat. No. 5,493,008 as medicine is however limited to a considerable extent because of their conformational flexibility, their instability to proteases and their poor bioavailability and pharmacodynamics (Milner-White, E. J. (1989) Trends Pharmacol. Sci. 10; 70–74. Verber, D. F.; Freidinger, R. M.; (1985) Trends Neurosci. 8; 392–396. Hruby, V. J. (1994) in: Peptides, Proc. Thirteenth American Peptide Symposium; (Hodges, R. S.; Smith, J. A.; Ed.) S. 3–17; ESCOM: Leiden, Netherlands).

An object of this application was thus to find low molecular weight peptide derivatives which are able to interact specifically with the laminin binding site of nidogen and to inhibit competitively the association between laminin and nidogen at low concentration.

Therefore, an object of the present invention is a compound of the formula I

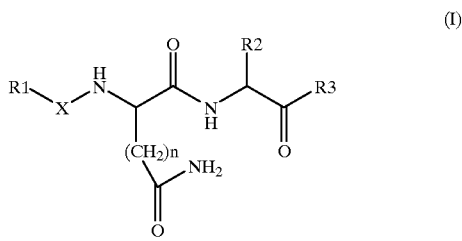

wherein

R1 is a group of one of the following formulae

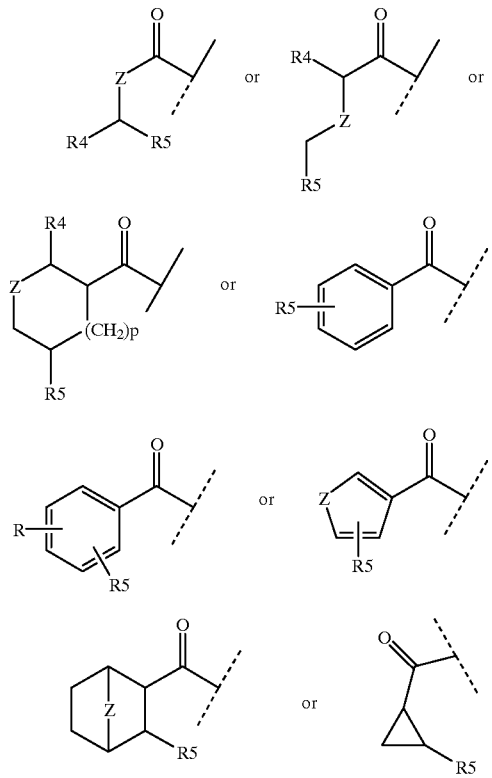

wherein

R4 means —A, —NH$_2$, —NHR, —NR$_2$, A$_2$, —NHR1,

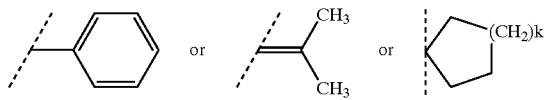

and R5 means —(CH$_2$)$_l$COOA, —(CH$_2$)$_l$CONH$_2$, —(CH$_2$)$_l$NH$_2$ or —(CH$_2$)$_l$—SO$_3$H,

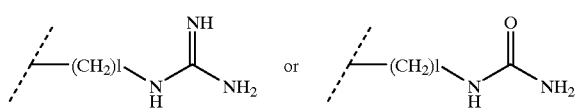

and X is a group of one of the following formulae

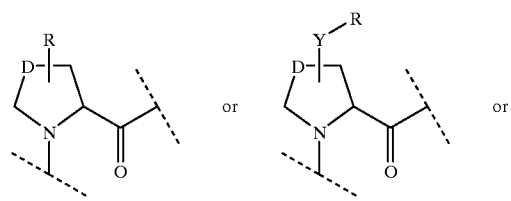

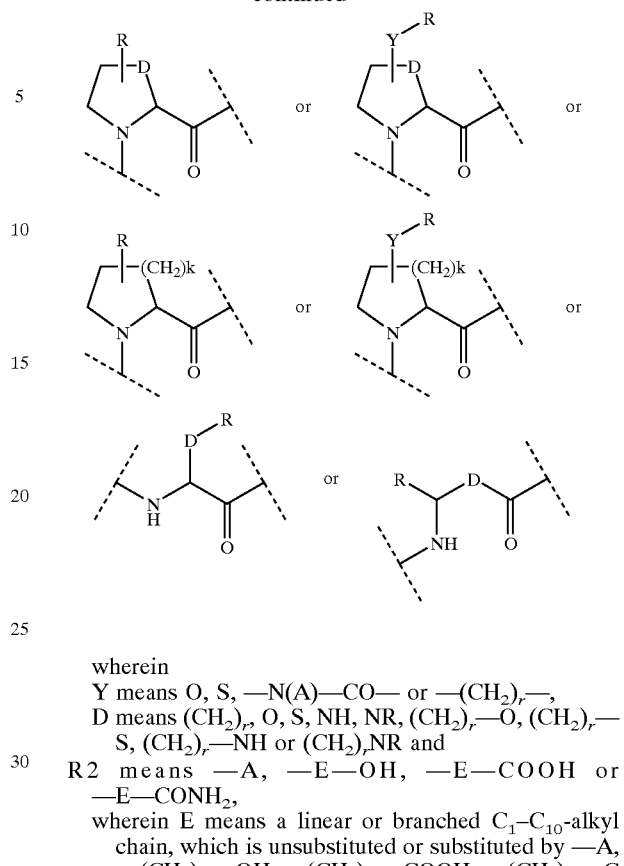

wherein
Y means O, S, —N(A)—CO— or —(CH$_2$)$_r$—,
D means (CH$_2$)$_r$, O, S, NH, NR, (CH$_2$)$_r$—O, (CH$_2$)$_r$—S, (CH$_2$)$_r$—NH or (CH$_2$)$_r$NR and
R2 means —A, —E—OH, —E—COOH or —E—CONH$_2$,
wherein E means a linear or branched C$_1$–C$_{10}$-alkyl chain, which is unsubstituted or substituted by —A, —(CH$_2$)$_m$—OH, —(CH$_2$)$_m$—COOH, —(CH$_2$)$_m$—C(O)NA$_2$ or by a C$_5$–C$_{10}$-cycloalkyl group,
or E means C$_5$–C$_{10}$-cycloalkyl, which is unsubstituted or substituted by —A, —(CH$_2$)$_m$—OH, —(CH$_2$)$_m$—COOH, —(CH$_2$)$_m$—C(O)NA$_2$ or by a C$_5$–C$_{10}$-cycloalkyl group,
and R3 is a group of one of the following formulae

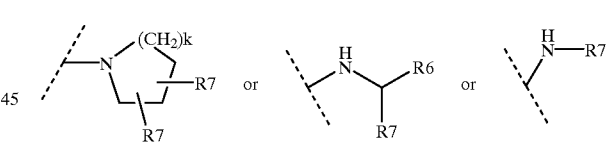

wherein R6 means —H, —COOH, —CONH$_2$, —CONHR, —CONR$_2$, —CH$_2$OH or

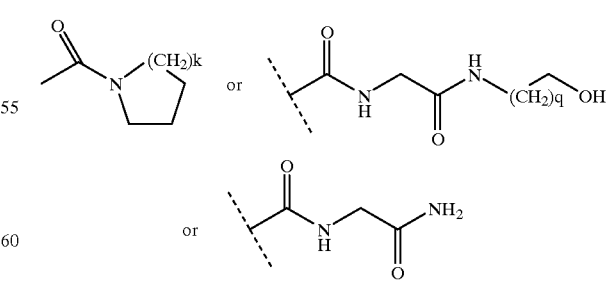

and wherein R7 means a linear or branched C$_1$–C$_{10}$-alkyl group, which is unsubstituted or substituted by —A, —(CH$_2$)$_m$—OH, —(CH$_2$)$_m$—COOH, —(CH$_2$)$_m$—C(O)NA$_2$ or by a C$_5$–C$_{10}$-cycloalkyl group, or R7 means a $C_5$–$C_{10}$-cycloalkyl group, which is unsubstituted or substituted by —A, —$(CH_2)_m$—OH, —$(CH_2)_m$—COOH, —$(CH_2)_m$—C(O)$NA_2$ or by a $C_5$–$C_{10}$-cycloalkyl group, and R means branched or unbranched $C_1$–$C_6$-alkyl, $C_2$–$C_6$-alkenyl, $C_2$–$C_6$-alkinyl, $C_5$–$C_{10}$-cycloalkyl, Het or Ar which are optionally substituted by one ore more halogen, $C_1$–$C_6$-alkyloxy, branched or unbranched $C_1$–$C_6$-alkyl, $C_2$–$C_6$-alkenyl, $C_2$–$C_6$-alkinyl or $C_5$–$C_{10}$-cycloalkyl groups or by —$C_1$–$C_6$-alkyl-Het, —$C_1$–$C_6$-alkyl-Ar, —O—$C_1$–$C_6$-alkyl-Het, —O—$C_1$–$C_6$-alkyl-Ar, Het or by Ar, wherein Het means a monocyclic or bicyclic, 5- up to 10-membered aromatic or non-aromatic ring containing 1 or 2 equal or different hetero-atoms as members of said ring, selected from the group consisting of nitrogen, oxygen and sulfur, which is unsubstituted or substituted by one or more hydroxy or carboxy groups, and wherein Ar means a monocyclic or bicyclic 5- up to 10-membered aromatic ring which is unsubstituted or substituted by one or more hydroxy or carboxy groups, and Z means $(CH_2)_m$, O, S, NH, NR, N—C(O)—R or $NSO_2R$, A means H or $C_1$–$C_4$-alkyl and l, m and r are integers from 0 to 3, n and k are integers from 1 to 2, p is an integer from 0 to 1 and q is an integer from 1 to 3, in all its stereoisomeric forms and mixtures thereof in all ratios including all its physiologically tolerable salts.

Physiologically tolerable salts are for example salts of inorganic and organic acids, e.g. hydrochloric acid, sulfuric acid, acetic acid, citric acid or p-toluenesulfonic acid, or salts of inorganic and organic bases, such as $NH_4OH$, NaOH, KOH, $Ca(OH)_2$, $Mg(OH)_2$, diethanolamine or ethylenediamine, or salts of amino acids, such as arginine, lysine, lysyl-lysine or glutamic acid.

One preferred embodiment of the present invention is a compound of formula I wherein n is 1.

A further preferred embodiment is a compound of formula I wherein R in group X means Het or Ar which are optionally substituted by —$C_1$–$C_6$-alkyl-Het, —$C_1$–$C_6$-alkyl-Ar, —O—$C_1$–$C_6$-alkyl-Het, —O—$C_1$–$C_6$-alkyl-Ar, Het or by Ar. More preferably, R in group X means Het. For example Het means

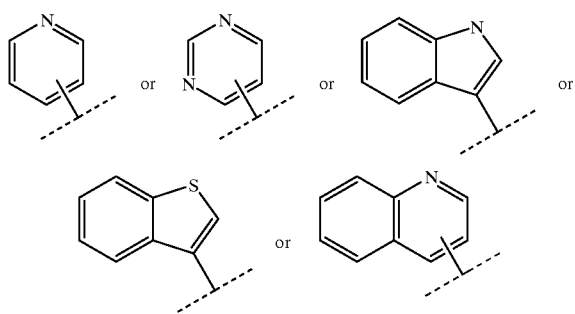

A preferred embodiment of the present invention is also compound of formula I wherein R in group X means Ar which is optionally substituted by —$C_1$–$C_6$-alkyl-Ar, —O—$C_1$–$C_6$-alkyl-Ar or by Ar. Preferably R in group X means Ar.

For example Ar means

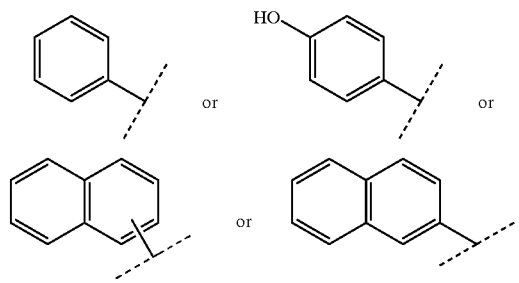

A preferred embodiment is also a compound of formula I wherein R in group X means

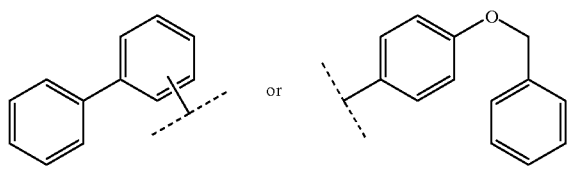

In the compound of formula I X is preferably a group of the following formula:

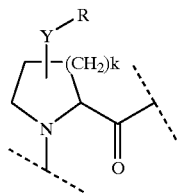

Preferably, Y means —$(CH_2)_r$, wherein r is preferably 0 or 1 and k is preferably 1 or 2.

A further preferred embodiment of the present invention is a compound of formula I wherein X is a group of the following formula

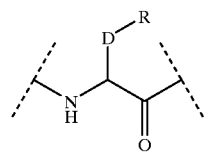

wherein D preferably means —$(CH_2)_r$—, wherein r is 0 or 1.

An also preferred embodiment of the present invention compound of formula I wherein R1 is a group of the following formula

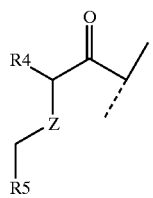

wherein Z means preferably $(CH_2)_m$ and m is 0 or 1. Preferably, R5 means —$(CH_2)_r$—COOA, wherein A means preferably H, or R5 means —(CH$_2$)$_l$—COONH$_2$, wherein l is 0. Preferably, R4 means —NH2 or —A, wherein A preferably means H, or preferably, R4 means —NHR1, wherein —NHR1 preferably means

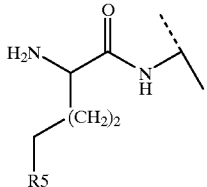

and wherein R5 of —NHR1 preferably means

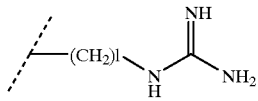

and l is preferably 0, or R5 of —NHR1 preferably means

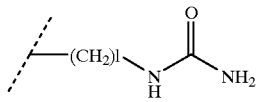

and l is preferably 0, or R5 of —NHR1 means preferably (CH$_2$)$_l$—NH$_2$ and l is preferably 0.

A further preferred embodiment of the present invention is a compound A compound of formula I wherein R1 is a group of the following formula

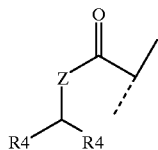

wherein Z means preferably —(CH$_2$)$_m$— and m is preferably 1 and wherein R4 preferably means —NH$_2$, and R5 preferably means —(CH$_2$)$_l$—COOA, wherein l is preferably 0 and wherein A preferably means H.

A further preferred embodiment of the present invention is a compound of formula I wherein R1 is a group of the following formula

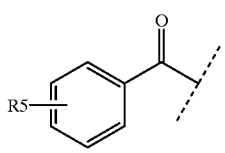

wherein R5 preferably means —(CH$_2$)$_l$—COOA, wherein l is preferably 0 and A preferably means H.

A further preferred embodiment of the present invention is a compound of formula I wherein R2 means A and A preferably means —CH$_3$, or wherein R2 means —E—COOH, preferably —CH$_2$—COOH, or wherein R2 means —E—OH, preferably —CH$_2$—OH.

A further preferred embodiment of the present invention is a compound of formula I wherein R3 is a group of the following formula

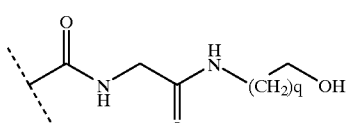

wherein k is preferably 2.

A further preferred embodiment of the present invention is a compound of formula I wherein R3 is a group of the following formula

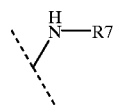

A further preferred embodiment of the present invention is a compound of formula I wherein R3 is a group of the following formula wherein R7 is preferably a branched C$_1$–C$_{10}$-alkyl group, preferably —CH(CH$_3$)$_2$, —C(CH$_3$)$_3$, —CH(CH$_3$)CH$_2$—CH$_3$ or —CH$_2$—CH(CH$_3$)$_2$, and wherein R6 preferably means —H, —COOH, —CONH$_2$, —CH$_2$OH, —CON(CH$_3$)$_2$ or, more preferably, wherein R6 means wherein q is preferably 2.

A further preferred embodiment of the present invention is a compound of formula I wherein R3 is a group of the following formula wherein R7 preferably means —CH(CH(CH$_3$)$_2$)$_2$ or —CH$_2$C(CH$_3$)$_3$.

Figure 1:
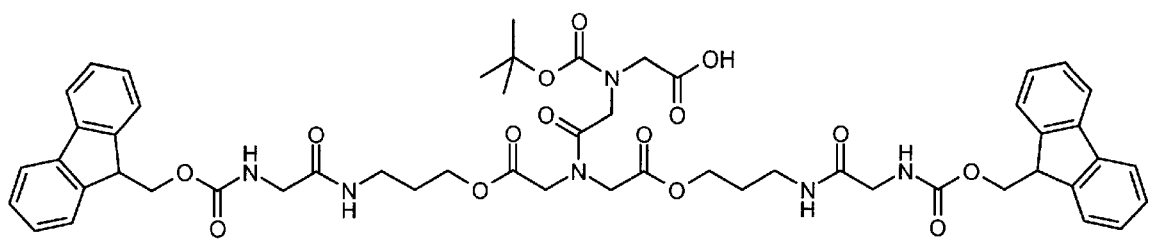
FIG. 1 illustrates a differentially cleavable linker.
Figure 2:
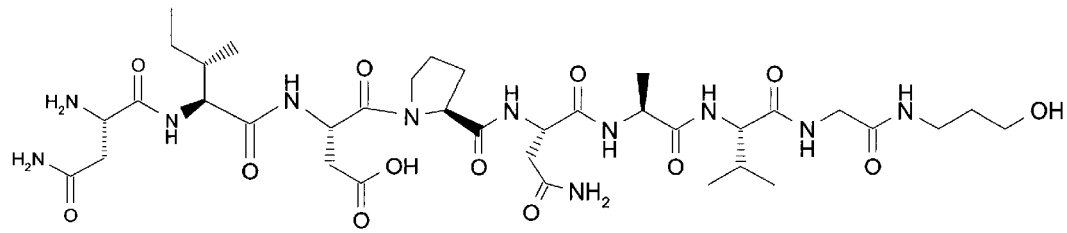
FIG. 2 illustrates the structures of compounds 1 to 4.
Figure 2:
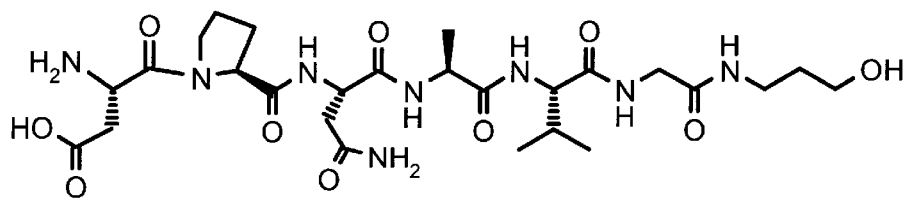
Figure 2:
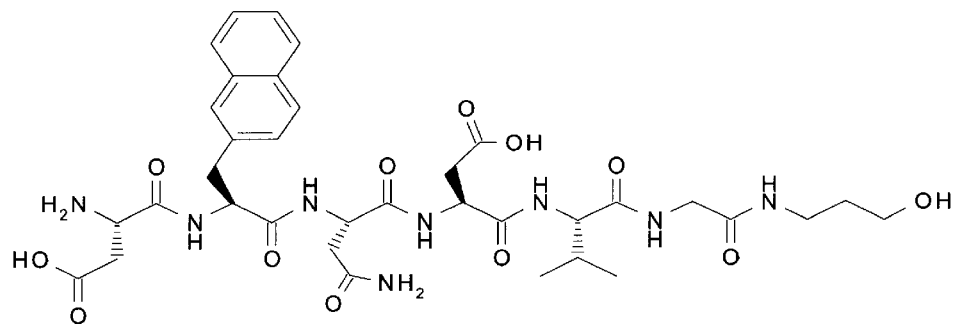
Figure 2:
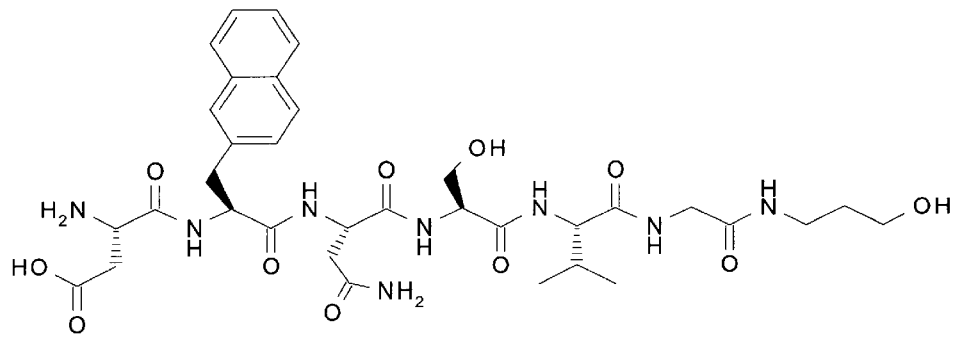
Figure 3:
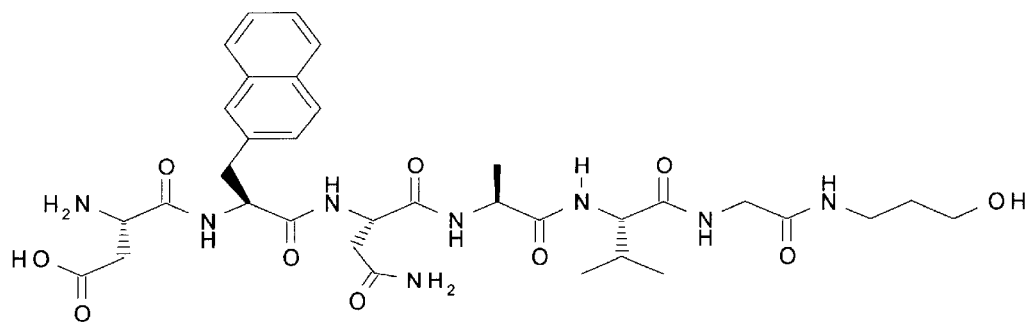
FIG. 3 illustrates the structures of compounds 5 to 8.
Figure 3:
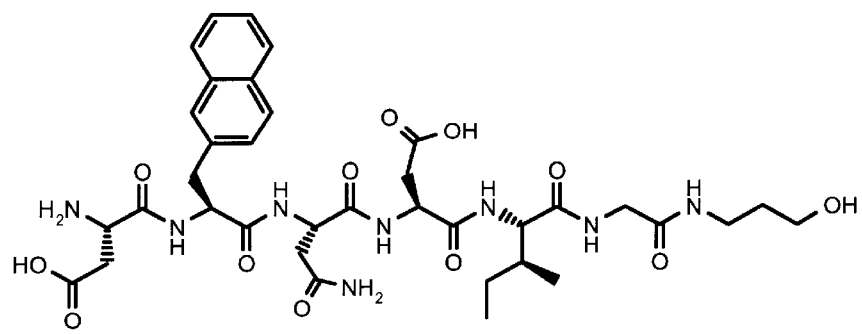
Figure 3:
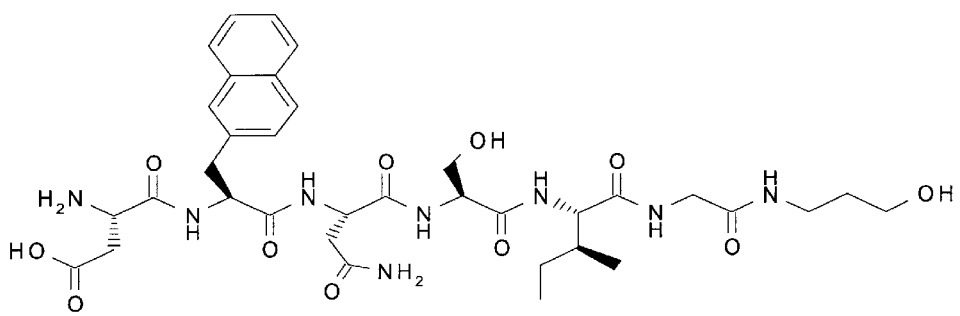
Figure 3:
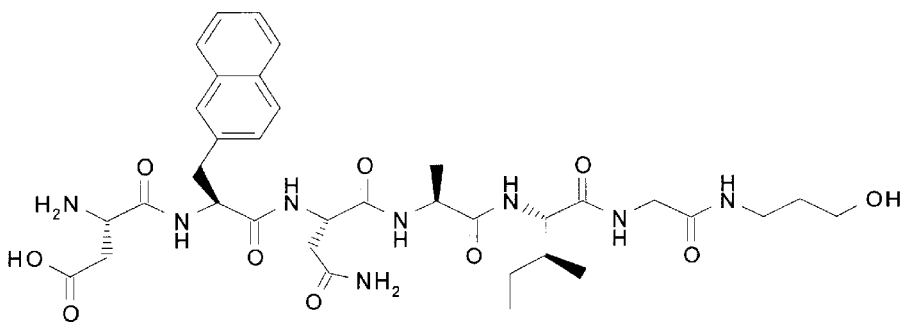
Figure 4:
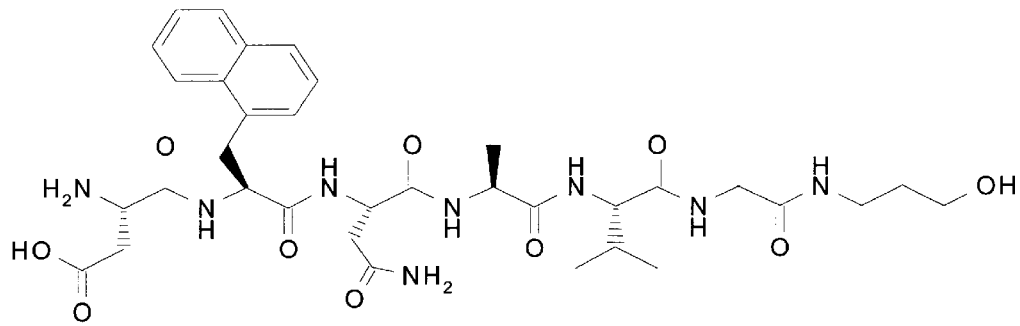
FIG. 4 illustrates the structures of compounds 9 to 12.
Figure 4:
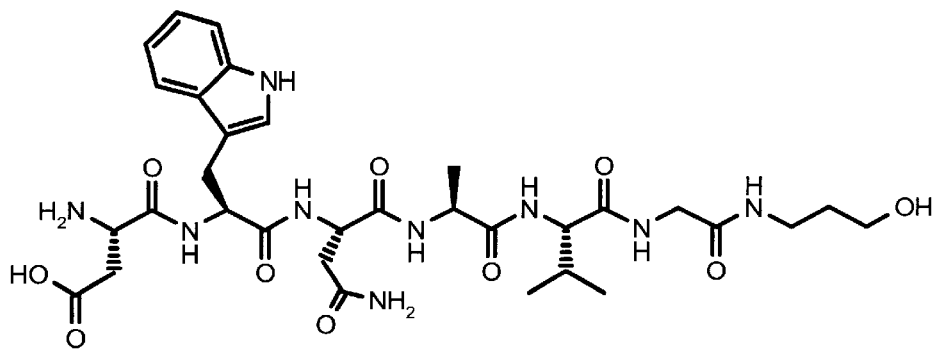
Figure 4:
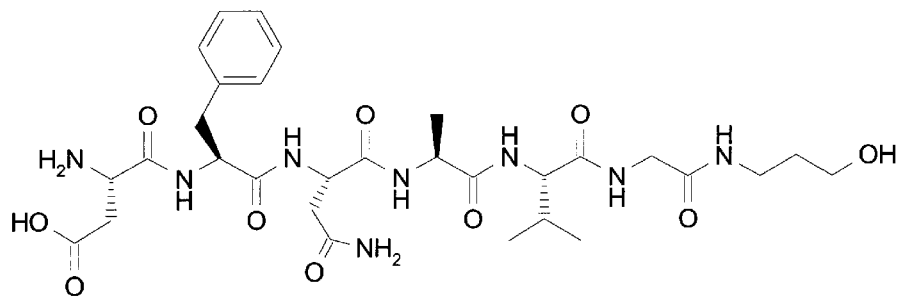
Figure 4:
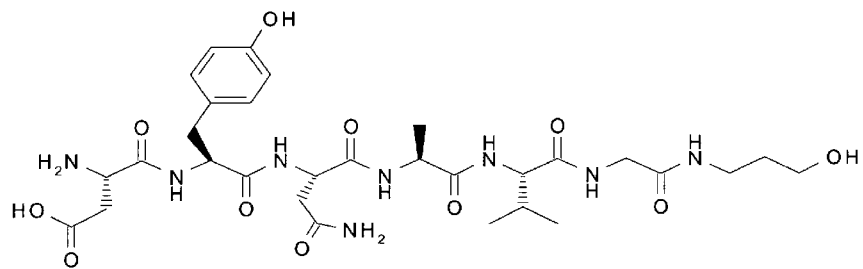
Figure 5:
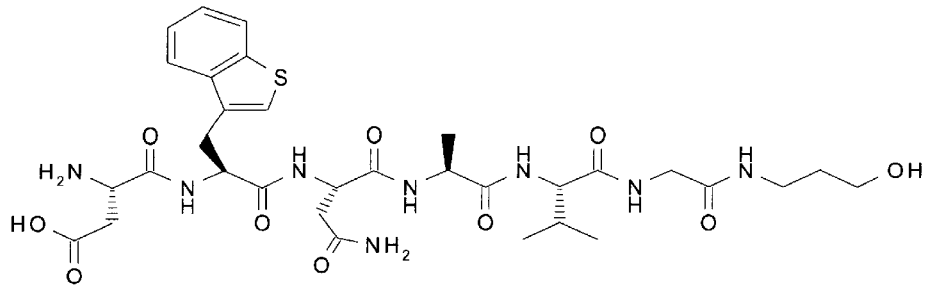
FIG. 5 illustrates the structures of compounds 13 to 16.
Figure 5:
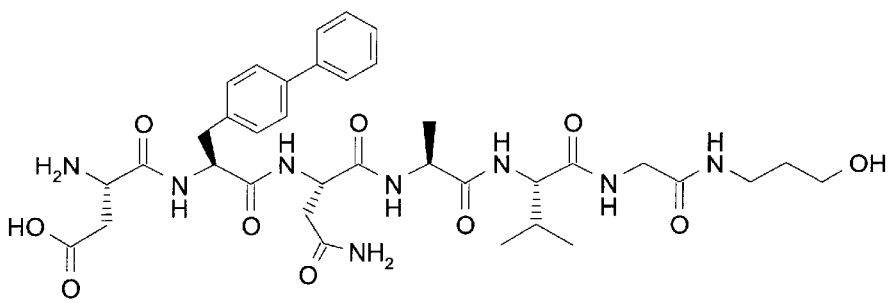
Figure 5:
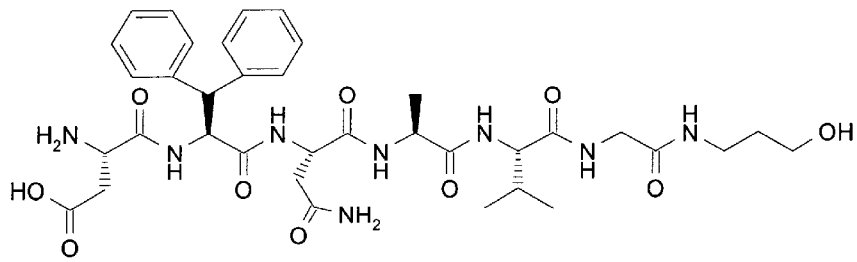
Figure 5:
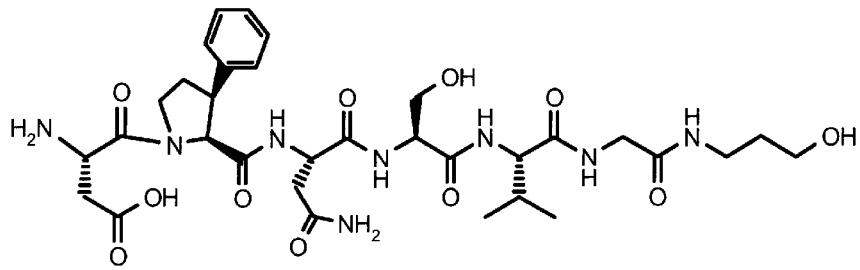
Figure 6:
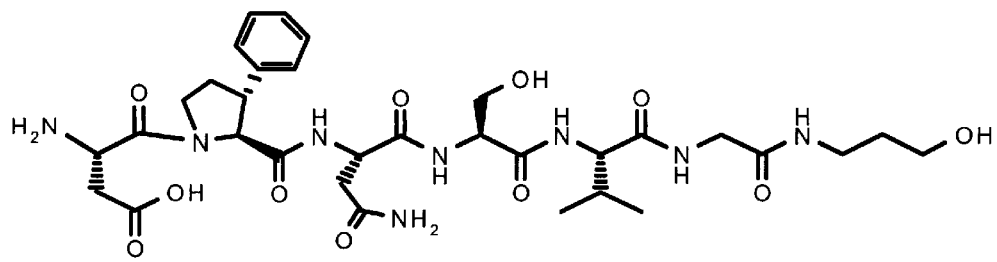
FIG. 6 illustrates the structures of compounds 17 to 20.
Figure 6:
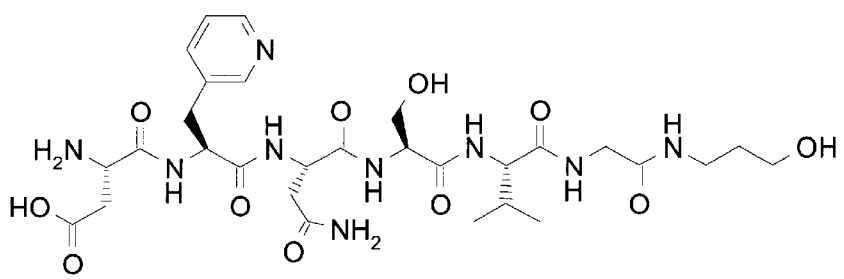
Figure 6:
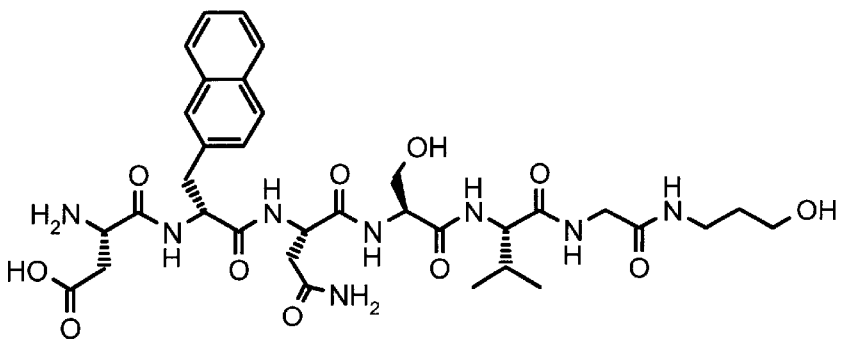
Figure 6:
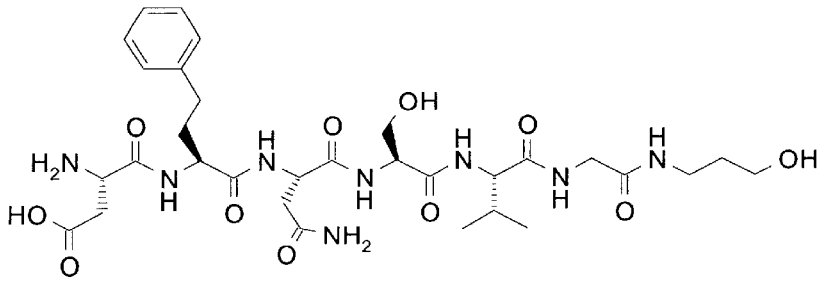
Figure 7:
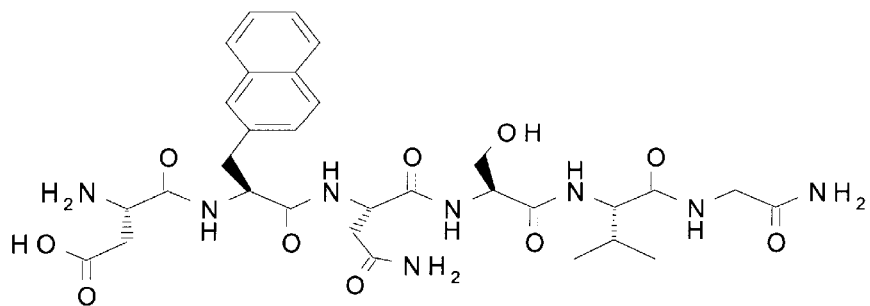
FIG. 7 illustrates the structures of compounds 21 to 24.
Figure 7:
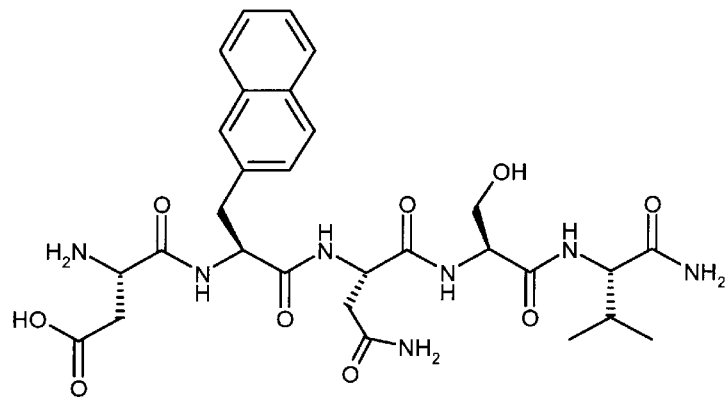
Figure 7:
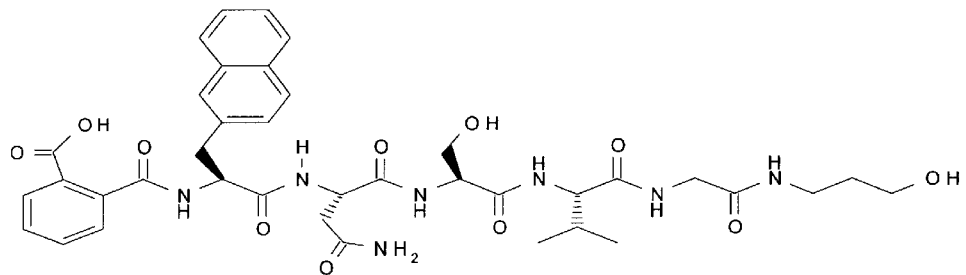
Figure 7:
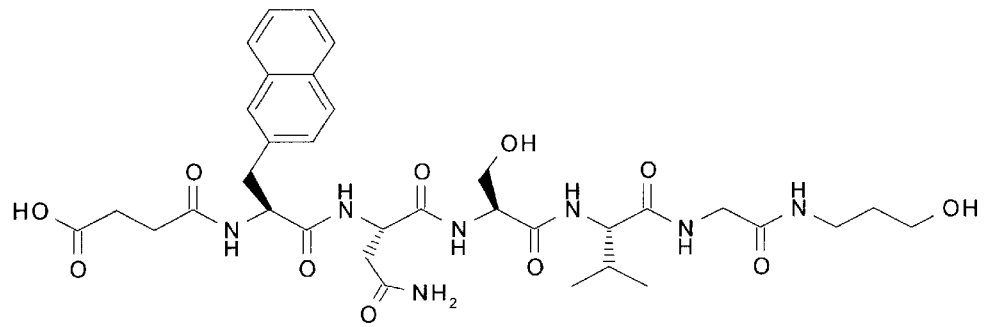
Figure 8:
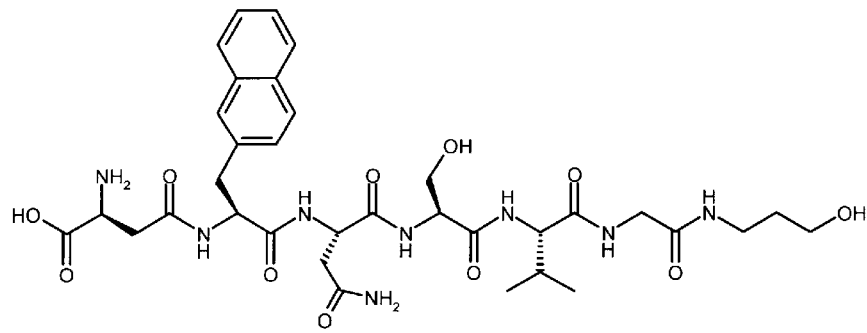
FIG. 8 illustrates the structures of compounds 25 to 28.
Figure 8:
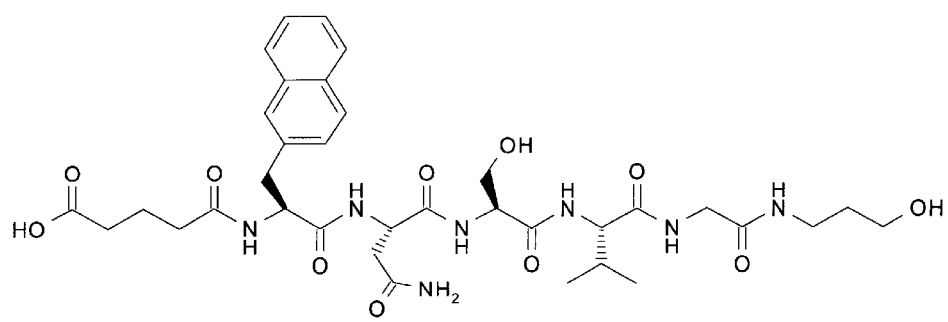
Figure 8:
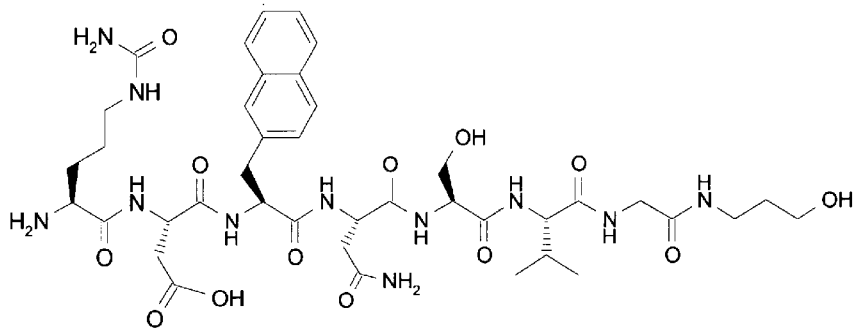
Figure 8:
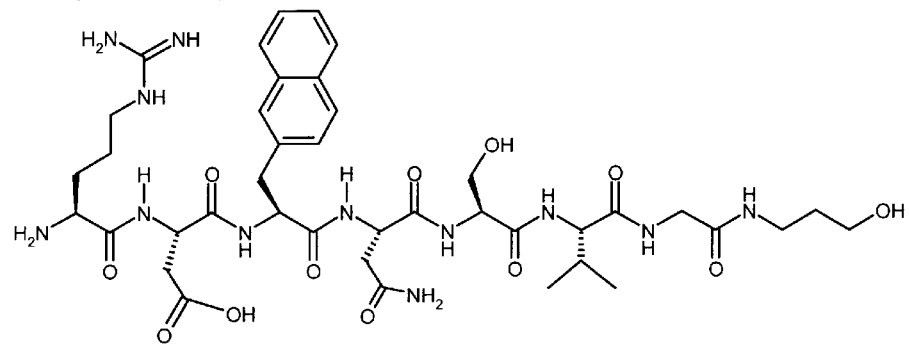
Figure 9:
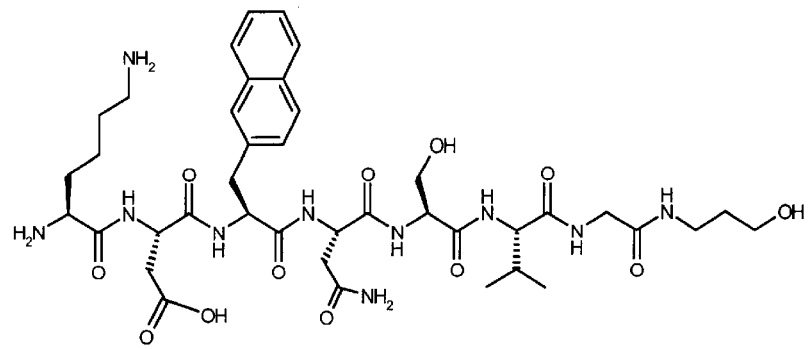
FIG. 9 illustrates the structures of compounds 29 to 32.
Figure 9:
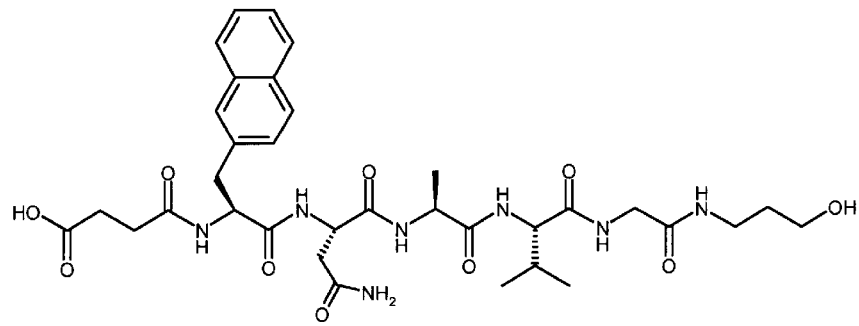
Figure 9:
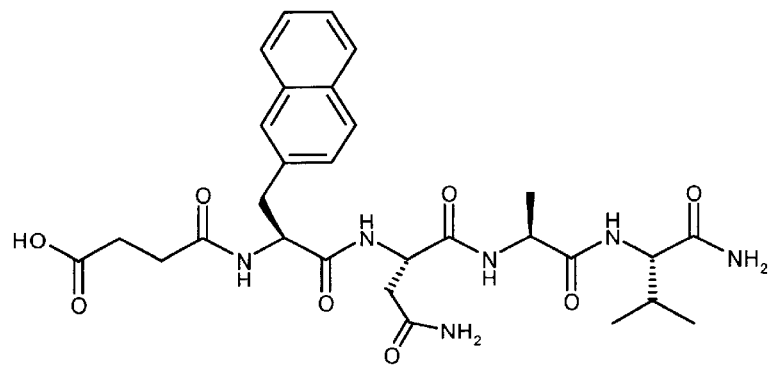
Figure 9:
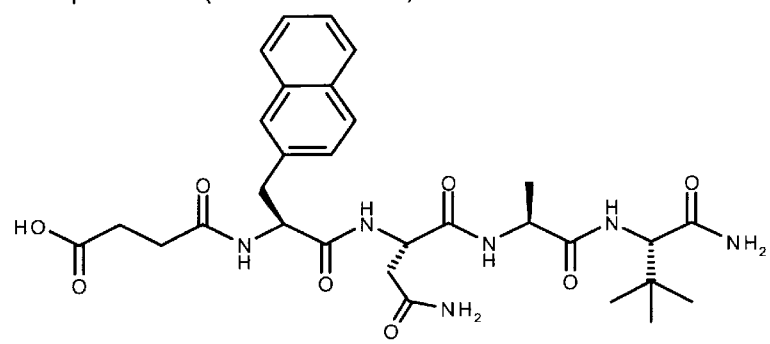
Figure 10:
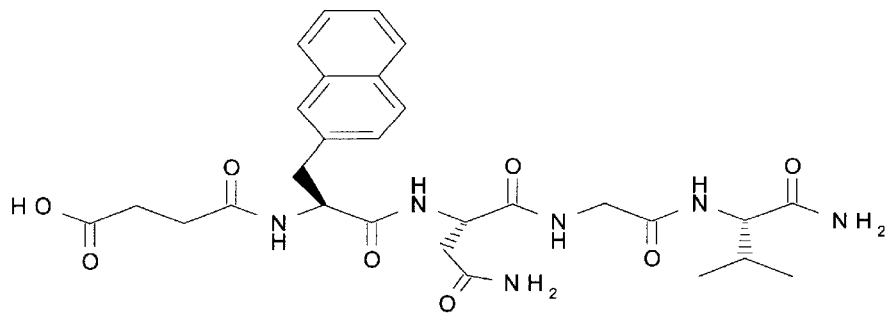
FIG. 10 illustrates the structures of compounds 33 to 36.
Figure 10:
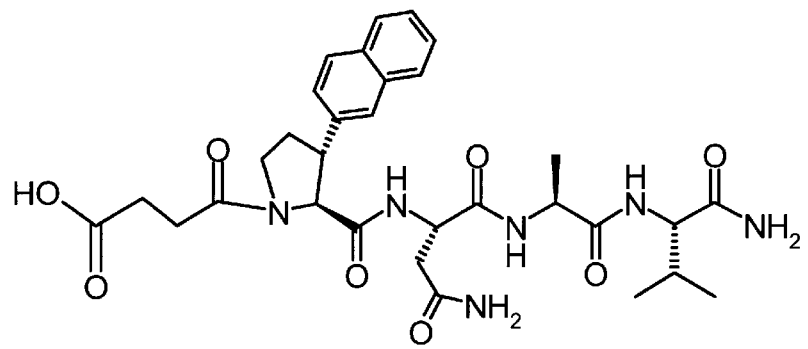
Figure 10:
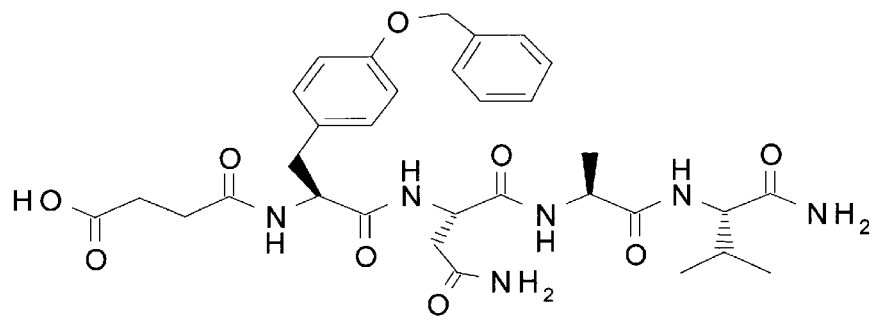
Figure 10:
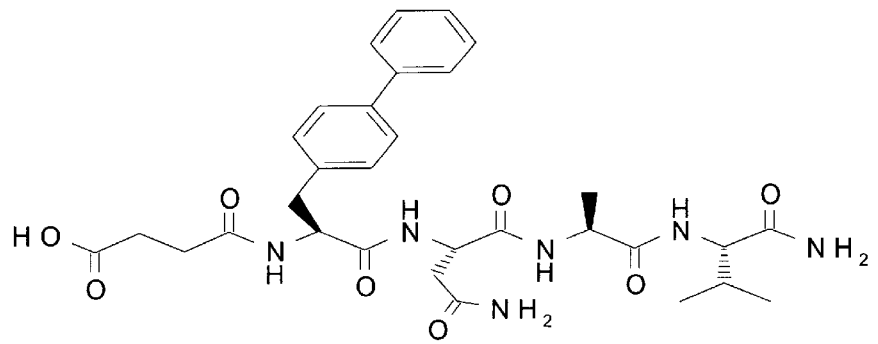
Figure 11:
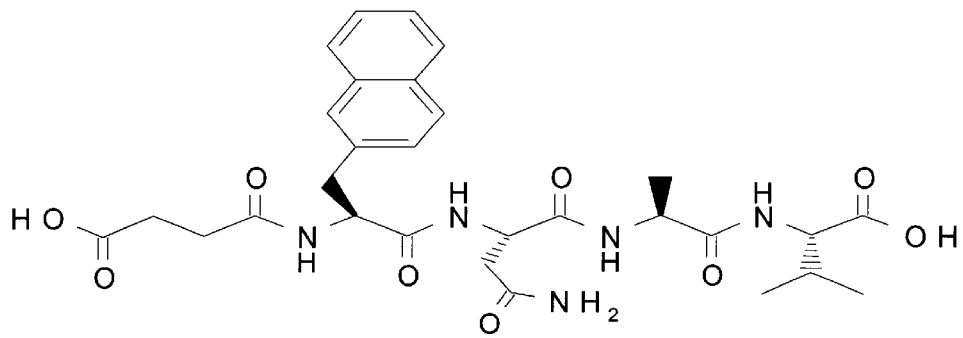
FIG. 11 illustrates the structures of compounds 37 to 40.
Figure 11:
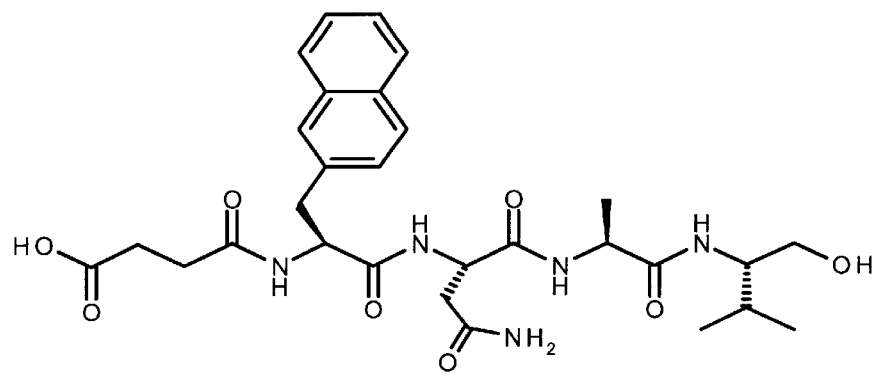
Figure 11:
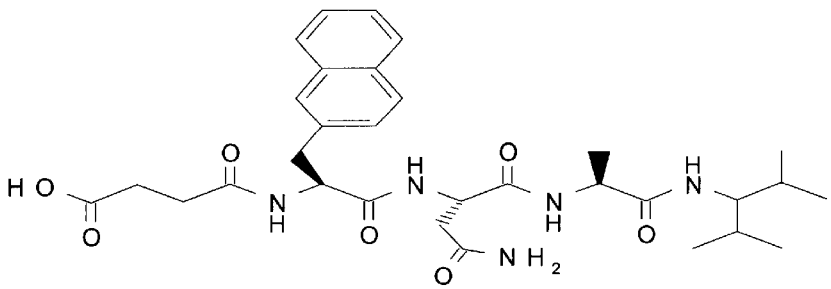
Figure 11:
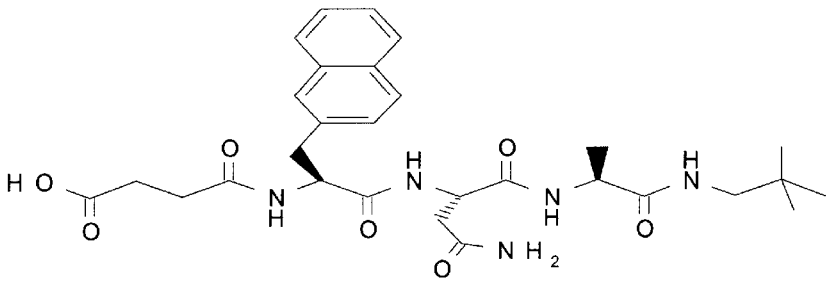
Figure 12:
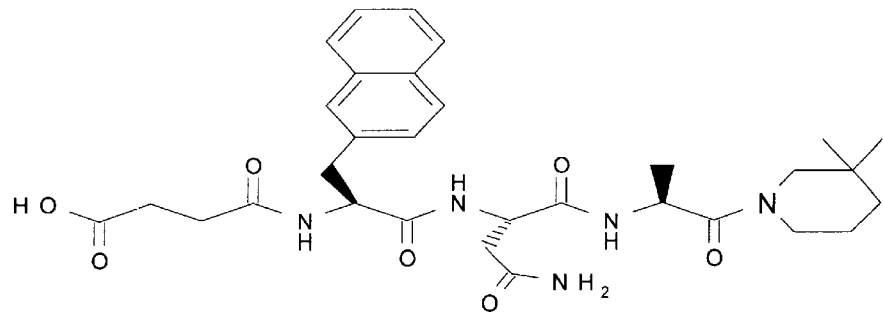
FIG. 12 illustrates the structures of compounds 41 to 43.
Figure 12:
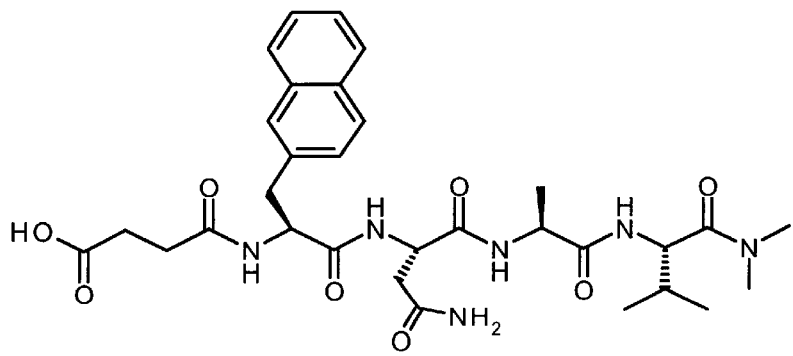
Figure 12:
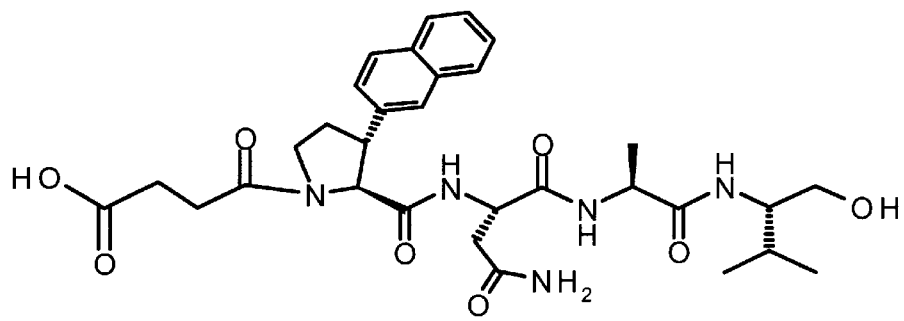

The compounds according to the present invention are unnatural (i.e. naturally not occurring), low molecular weight peptide derivatives which are able to inhibit the laminin/nidogen interaction in the nM concentration range. Surprisingly, the low molecular weight structures which have been found are capable of high-affinity binding to the laminin binding site of nidogen without this requiring an interaction with a tyrosine or histidine from a loop (loop c) adjacent to the actual binding sequence.

It is all the more surprising that the low molecular weight peptide derivatives, with molecular weights between 550 and 800 Da, described in the present invention show inhibition of the same order of magnitude compared to the most active peptide described to date (IC50 of 22 nM) having a molecular weight of about 2700 Da (≙about 50% of an LE module) and comprising an intact S—S loop which presumably stabilizes the structure of the essential NIDPNAV (SEQ ID NO:1) sequence region (J. W. Fox and R. Timpl; U.S. Pat. No. 5,493,008).

The object was achieved by specifically synthesizing, on the basis of structure/function relationships and the published three-dimensional structure of the nidogen binding site, peptide derivatives on resin supports. The building blocks for the peptide syntheses were varied in accordance with suitable criteria to ensure a wide structural diversity and the integration of unnatural building blocks. A suitable, sensitive screening assay was used to test and compare the resulting peptide derivatives for inhibitory activity after they had been cleaved off the support resin.

The compounds according to the present invention can be used for preparing a pharmaceutical for the treatment of a disease which is related to an increased or unwanted synthesis of basement membranes.

Therefore, possible areas of therapeutic use of the present peptide derivatives and/or the physiologically tolerable salts thereof are:

1. All types of late complications of diabetes which are accompanied by thickening of basement membranes (especially in the kidney, eye, vascular system).
2. Hepatic fibrosis, especially alcoholic hepatic fibrosis, characterized by synthesis of a continuous basement membrane in the sinusoids and a capillarization caused thereby.
3. All fibroses (chronic or iatrogenic) in which an increased synthesis of basement membrane or components of the basement membrane can be observed (kidney, lung, skin).
4. Atherosclerosis characterized by a limitation of the regulation of lipid metabolism, which may be caused inter alia by impaired filtration of lipoproteins through the partly capillarized liver sinusoids. The pathological changes in the vascular system which can be observed with atherosclerosis may also in part be attributed to modifications of the composition and structure of the basement membranes in the vessels.
5. Diseases in which angiogenesis contributes to a deterioration in the clinical picture, for example cancers in which neovascularization is required for tumor growth, diabetic retinopathy, retrolental fibroplasia, disorders with a strong inflammatory component (for example rheumatoid arthritis, osteoarthritis, vasculitis), hemangiomas, psoriasis, and many others.

Thus, the compounds according to the present invention and/or their respective physiologically tolerable salts are suitable for use as a pharmaceutical. Therefore, a further object of the present invention is a pharmaceutical composition containing at least one compound according to the present invention and/or its physiologically tolerable salts.

The compounds of the formula I and their physiologically tolerable salts and derivatives can be administered according to the invention to animals, preferably to mammals, and in particular to humans, as pharmaceuticals for therapy or prophylaxis. They can be administered per se, in mixtures with one another or in the form of pharmaceutical preparations which permit enteral or parenteral administration and which as active constituent contain an efficacious dose of at least one compound of the formula I and/or its physiologically tolerable salts and derivatives in addition to customary pharmaceutically innocuous excipients and/or additives.

The pharmaceuticals can be administered systemically or locally. They can be administered, for example, in the form of pills, tablets, film-coated tablets, sugar-coated tablets, granules, hard and soft gelatin capsules, powders, solutions, syrups, emulsions, suspensions or in other pharmaceutical forms. However, administration can also be carried out vaginally or rectally, for example in the form of suppositories, or parenterally or by implantation, for example in the form of injection solutions or infusion solutions, microcapsules or rods, or topically or percutaneously, for example in the form of ointments, solutions or tinctures, or in another way, for example in the form of nasal sprays or aerosol mixtures or as inhalable dry powder preparations. If solutions are parenterally administered they can be administered, for example, intravenously, intramuscularly, subcutaneously, intraarticularly, intrasynovially or in another manner, e.g. by inhalation of wet aerosols or dry powder preparations.

The pharmaceutical preparations according to the invention are prepared in a manner known per se, it being possible to use pharmaceutically inert inorganic and/or organic excipients in addition to the compound(s) of the formula I and/or its/their physiologically tolerable salts and derivatives. For the preparation of pills, tablets, sugar-coated tablets and hard gelatin capsules, it is possible to use, for example, lactose, cornstarch or derivatives thereof, talc, stearic acid or its salts etc. Excipients for soft gelatin capsules and suppositories are, for example, fats, waxes, semisolid and liquid polyols, polyethylene glycols, natural or hardened oils etc. Suitable excipients for the preparation of solutions, for example injection solutions, or of emulsions or syrups are, for example, water, alcohols, glycerol, diols, polyols, sucrose, invert sugar, glucose, vegetable oils etc. Suitable excipients for microcapsules, implants or rods are, for example, copolymers of glycolic acid and lactic acid. The pharmaceutical preparations normally contain approximately 0.5 to 90% by weight of the compounds of the formula I and/or their physiologically tolerable salts and derivatives.

In addition to the active compounds and excipients, the pharmaceutical preparations can additionally contain auxiliaries or additives, such as, for example, fillers, disintegrants, binders, lubricants, wetting agents, stabilizers, emulsifiers, preservatives, sweeteners, colorants, flavorings or aromatizers, thickeners, diluents, buffer substances, solvents or solubilizers, means for achieving a depot effect, salts for altering the osmotic pressure, coating agents or antioxidants. They can also contain two or more compounds of the formula I and/or their physiologically tolerable salts and derivatives. Furthermore, they can also contain one or more other therapeutically or prophylactically active substances in addition to at least one compound of the formula I and/or its physiologically tolerable salts and derivatives. The pharmaceutical preparations normally contain 0.2 to 500 mg, preferably 1 to 100 mg, of active compound of the formula I and/or its physiologically tolerable salts and derivatives per dose.

If the compounds of the formula I or pharmaceutical preparations containing them are administered as aerosols, for example as nasal aerosols or by wet aerosols or dry powder inhalation, this can be effected, for example, using a spray, an atomizer, a pump atomizer, an inhalation apparatus, a metered inhaler or a dry powder inhaler, respectively. Pharmaceutical forms for administration of the compounds of the formula I as an aerosol can be prepared by the process well known to the person skilled in the art. For their preparation, for example, solutions or dispersions of the compounds of the formula I in water, water-alcohol mixtures or suitable saline solutions using customary additives, for example benzyl alcohol or other suitable preservatives, absorption enhancers for increasing the bioavailability, solubilizers, dispersants and others, and, if appropriate, customary propellants, for example chlorofluorohydrocarbons and/or fluorohydrocarbons are suitable, whereas dry powder preparations of the compounds of the formula I and/or their physiologically tolerable salts may be obtained by freeze drying or preferably spray drying aqueous solutions of the compounds of the formula I and/or their physiologically tolerable salts and of suitable water soluble additives, such as sugars or sugar derivatives and amino acids.

The dose when using the compounds of the formula I can vary within wide limits, and as customary it is to be tailored to the individual conditions in each individual case, as is known to the physician. It depends, for example, on the nature and severity of the disease to be treated, on the compound employed or whether an acute or chronic disease state is treated or prophylaxis is conducted or on whether further active compounds are administered in addition to the compounds of the formula I. In general, in the case of oral administration, a daily dose of approximately 0.01 to 100 mg/kg, preferably 0.1 to 10 mg/kg, in particular 0.3 to 2 mg/kg (in each case per kg of body weight) is appropriate in an adult to achieve effective results. In the case of intravenous administration, the daily dose is in general approximately 0.01 to 50 mg/kg, preferably 0.01 to 10 mg/kg of body weight. In particular when relatively large amounts are administered, the daily dose can be divided into a number, for example 2, 3 or 4, of part administrations. If appropriate, depending on individual behavior, it may be necessary to deviate upward or downward from the indicated daily dose.

Furthermore, the compounds of the formula I and their salts according to the present invention can be used as intermediates for the preparation of other compounds, in particular of other pharmaceutical active compounds which are obtainable from compounds of the formula I, for example, by modification or introduction of radicals or functional groups, for example by esterification, reduction, oxidation or other conversions of functional groups.

The peptide derivatives according to the present invention thus found can on the one hand be used directly as therapeutic agent, but they can also form the basis for related structures, which are also suitable for use as therapeutic agent for treating diseases relating to an increased or unwanted synthesis of basement membranes.

A further object of the present invention is a method for identifying a compound that inhibits the interaction of laminin and nidogen wherein the compound according to the present invention is used as a competetive inhibitor. This method may further comprise the formulation of the compound identified in a pharmaceutical acceptable form.

It is also an object of the present invention to provide a method for producing a pharmaceutical composition comprising the identification of a compound that inhibits the interaction of laminin and nidogen wherein the compound according to the present invention is used as a competetive inhibitor and furthermore mixing the compound identified and/or its physiologically tolerable salts with a pharmaceutical acceptable carrier.

It is also an object of the present invention to provide a method for preparing the compound of the formula I according to the present invention.

The compound of formula I

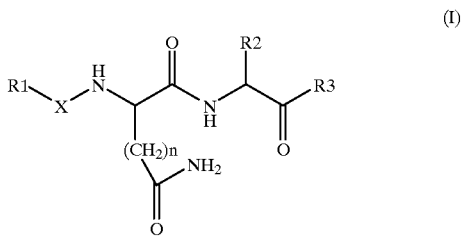

according to the present invention is prepared by a fragment condensation of a compound of formula II

with a compound of formula III

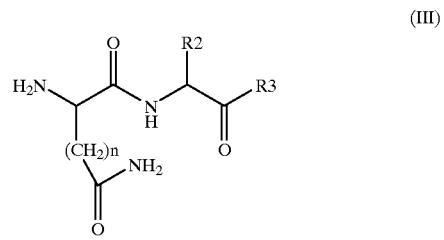

wherein the variables R1, X, n, R2 and R3 have the above-mentioned meanings and whereby the compounds of formulae II and III may be protected at the functional groups defined above by usual protecting groups known in peptide chemistry (see for example Houben-Weyl, Methoden der Organischen Chemie, vol. 15/1 and 15/2, Georg Thieme Verlag, Stuttgart, 1974). Suitable condensation methods are well known in the art (Houben-Weyl, Methoden der Organischen Chemie, vol. 15/1 and 15/2, Georg Thieme Verlag, Stuttgart, 1974). Suitable condensation agents or coupling reagents are for example carbonyl-diimidazoles, carbodiimides, such as di-cyclohexyl-carbodiimide or di-isopropyl-carbodiimide, or O-((cyano(ethoxycarbonyl)methylene)-amino)-N,N,N',N'-tetra-methyl-uronium-tetrafluoro-borate (TOTU) or pyro-phosphoric acid anhydride (PPA). The condensation reactions are carried out under standard conditions. As a rule, it is necessary during peptide condensation to protect amino groups which are not intended to be involved in the coupling reaction by protecting groups which are easily removed under conditions different to the conditions under which coupling occurs. The same applies for the carboxy groups not involved in the coupling reaction, which are preferably protected as $C_1$–$C_6$-alkyl esters, benzyl esters or tert-butyl esters during the coupling reaction. A protection of the amino groups is not necessary in case the amino groups are still present in the form of amino group precursors, e.g. in form of nitro or cyano groups. The amino groups are then formed by a hydration step subsequent to the condensation reaction. After the condensation step the protecting groups are removed by known suitable methods, e.g. benzyloxycarbonyl and benzyl groups can be removed by hydration in benzyl esters; protecting groups of the tert-butyl type are in general cleaved under acidic conditions; the 9-fluorenylmethyloxycarbonyl residue is removed by secondary amines.

The preparation of the compound of the formula I according to the present invention may also be performed by stepwise addition of the respective components, e.g. natural, unnatural amino acids and their derivatives, on a solid phase, whereby the components may be added in various different sequences.

It may also be advantageous in order to produce the compound of formula I not to directly couple the compounds of formulae I and II by a fragment condensation but to couple their respective suitable precursors in order to obtain an intermediate which can be transferred into the compound of the formula I e.g. by derivatization.

The above described method for introducing functional groups not directly, but by the way of their respective precursors into the molecule in order to obtain intermediates from which the final product can easily be obtained by transforming the precursor groups into the respective functional groups subsequently to a condensation reaction may also be applied for different parts of the molecule of the compound of formula I, e.g. for the side chain of the compound of formula, I R1- or R1-X-, respectively.

EXAMPLES

The abbreviations have the following meanings:

| Agents and solvents: | |
|---|---|
| AcOH | acetic acid |
| aq | aqueous |
| BSA | bovine serum albumin |
| DCC | N,N'-dicyclohexylcarbodiimide |
| DCM | dichloromethane |
| DIPEA | N,N-diisopropylethylamine |
| DMAP | 4-dimethylaminopyridine |
| DMF | N,N-dimethylformamide |
| DMSO | Dimethylsulfoxide |
| Et$_2$O | Diethylether |
| EtOAc | Ethylethanoate (acetic acid ethylester) |
| EtOH | ethanol |
| Fmoc-OSucc | Fmoc-O-succinimide |
| HOBT | 1-hydroxybenzotriazole |
| KHMDS | potassiumhexamethyldisilazide |
| n-Buli | n-butyl-lithium |
| MeOH | methanol |
| MTBE | methyl tert-butyl ether |
| TEA | triethylamine |
| TFA | trifluoroacetic acid |
| THF | tetrahydrofuran |
| TMEDA | tetramethylethylendiamine |
| TMSCI | trimethylsilyl chloride |
| TOTU | O-((cyano(ethoxycarbonyl)methylene)amino)-N,N,N',N'-tetramethyluronium tetrafluoroborate |
| TrisN$_3$ | trisilyl azide |
| Chemical groups: | |
| Me | methyl | $CH_3$— |
| Et | ethyl | $CH_3$—$CH_2$— |
| nPr | n-propyl | $CH_3CH_2CH_2$— |
| iPr | isopropyl | $(CH_3)_2CH$— |
| nBu | n-butyl | $CH_3CH_2CH_2CH_2$— |
| iBu | isobutyl | $(CH_3)_2CHCH_2$— |
| tBu | tert-butyl | $(CH_3)_3C$— |
| Ph | phenyl | $C_6H_5$— |
| Fmoc | 9-fluorenylmethoxycarbonyl | |
| Z | benzyloxycarbonyl | $C_6H_5$—$CH_2$—O—CO— |
| BOC | tert-butyloxycarbonyl | $(CH_3)_3C$—O—CO— |

1. Screening of a library of inhibitors of Laminin/Nidogen interaction

The library was designed to find smaller, more potent and more metabolically stable peptides related to the previously known heptapeptide NIDPNAV (SEQ ID NO:1) (Pöschl, E.; Fox, J. W.; Block, D.; Mayer, U.; Timpl, R, (1994) EMBO J. 13; 3741–3747. Pöschl, E.; Mayer, U.; Stetefeld, J.; Baumgartner, R.; Holak, T. A.; Huber, R.; Timpl, R. (1996) EMBO J. 15: 5154–5159. Baumgartner, R.; Czisch, M.; Mayer, U.; Pöschl, E.; Huber, R.; Timpl, R.; Holak, T. A. (1996) J. Mol. Biol. 257; 658–668). The library was synthesized and screened as three sublibraries; pentamer, hexamer and heptamer. Following is a description of the screening strategy for the pentamer sublibrary. The method is representative of the methods employed for the other two sublibraries, except that the hexamers were screened in the first step at about 50 beads per well and the heptamers were screened at about 100 beads per well.

1.1 Screening of the pentamer library.

The pentamer library contained 2,160 different compounds.

1) About 8,800 individual beads were suspended in 0.1% HCl and distributed into seven filter bottom 96 well microtiter plates at approximately fourteen beads per well.

2) The beads were washed twice with 200 μl de-ionized water, then 50 μl of 500 mM HEPES, pH 7.0 was added. The linker used in the library releases one aliquot of compound when the pH is increased to 7.0, and this cleavage step was allowed to proceed overnight.

3) The plates were stacked on top of U-bottom filter plates and centrifuged. The mixtures of compounds released from the beads were collected in the bottom plate, while the corresponding beads remain in the original filter plate.

4) 25 μl DMSO per well was added to the beads to wash remaining free compound from the beads, and the plates were centrifuged again to separate the compounds in solution from the beads. The resulting stock was presumably 27 μM per compound in 333 mM HEPES, 33% DMSO.

5) The compound stocks were preincubated with nidogen (10 μl compound stock to 90 μl nidogen solution) and the assay was performed as described in the attached protocol, yielding a final screening concentration of 2.7 μM per compound.

6) In the 25 assay wells where reproducible inhibition of 62% occurred, the corresponding beads from the original filter plates were suspended in 0.05% HCl, 0.1% Tween-20 and pipetted into five new filter plates at 1 bead per well. Two control beads with the parent compound on the same linker were added to each plate as controls.

7) The beads were washed twice with 200 μl de-ionized water, then 25 μl of 50 mM NaOH was added to each well. The linker used in the library releases the second equimolar aliquot of compound when the pH is increased from 7.0 to 10.0 or more. This cleavage step was allowed to proceed for 3 hours.

8) The plates were stacked on top of U-bottom filter plates and centrifuged. The compounds released from the beads were collected in the bottom plate, while the corresponding beads remained in the original filter plate.

9) The beads were washed with 20 μl of 50 mM HEPES (initial pH 7.0) with 50 mM HCl added, and the solution was centrifuged into the lower plate and combined with the first releasate.

10) beads were washed a third time with 25 μl DMSO, which was allowed to equilibrate with the beads for 10 minutes before centrifugation.

11) The resulting releasates were assayed at 1/10th volume, as in Step #5.

12) Solutions which inhibited as well or better than the control beads (about 50% inhibition) were considered hits. 23 hit beads were recovered, with the other two potential hit wells being explainable by additive weak inhibitors in single wells.

13) Hit solutions were subjected to mass spectrometry to determine the molecular weights.

14) The corresponding individual hit beads were subjected to Edman degradation to determine peptide sequences.

15) The combined MS and Edman data was analyzed to identify the hit compound structures.

The structures and frequency of their recovery are shown below. G-Hopa=glycine hydroxypropyl amide, the linker remnant.

| Frequency | | | | | | | $IC_{50}$, µM |
|---|---|---|---|---|---|---|---|
| 6 | D | Nal2 | N | D | V | G-Hopa (SEQ ID NO: 2) | 0.43 |
| 4 | D | Nal2 | N | A | V | G-Hopa (SEQ ID NO: 3) | 0.37 |
| 4 | D | Nal2 | N | D | I | G-Hopa (SEQ ID NO: 4) | 0.64 |
| 4 | D | Nal2 | N | S | V | G-Hopa (SEQ ID NO: 5) | 0.49 |
| 3 | D | Nal2 | N | S | I | G-Hopa (SEQ ID NO: 6) | 0.81 |
| 2 | D | Nal2 | N | A | I | G-Hopa (SEQ ID NO: 7) | 0.47 |

Legende:
Nal2 = L-3-(2-naphthyl)-alanyl:

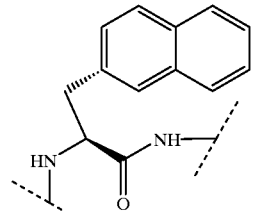

G-Hopa = glycine-3-hydroxypropylamide:

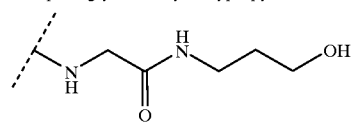

D = Asp (aspartyl),
P = Pro (prolyl),
N = Asn (asparaginyl),
A = Ala (alanyl),
V = Val (valinyl),
S = Ser (seryl),
I = Ile (isoleucyl).

1.2 Procedures: Preparation of the peptide library

Peptide libraries were synthesized by a split/mix synthesis approach (Lam, K. S., Salmon, S. E., Hersh, E. M., Hruby, V. J., Kazmierski, W. M., and Knapp, R. J. (1991) Nature 354, 82; Furka, A., Sebestyen, F., Asgedom, M., and Dibo, G. (1991) lnt. J. Pept. Protein Res. 37, 487) using standard solid-phase peptide Fmoc. chemistry (Stewart, J. M., and Young, J. D. (1984) Solid Phase Peptide Synthesis. Pierce Chemical Co., Rockford, Ill.; Atherton, E., and Sheppard, R. C. (1989) Solid Phase Peptide Synthesis. IRL Press Oxford). Each resin bead was exposed to only a single activated amino acid at each coupling cycle. Therefore, at the completion of the library synthesis, each resin bead expresses only one peptide entity. Since it is not possible to test all compounds separately, we have built the same structure on each resin bead in two copies via differentially cleavable linker, FIG. 1 (Kocis, P., Krchnak, V., and Lebl, M. (1993) Tetr.Lett. 34, 7251; Lebl, M., Krchnak, V., Salmon, S. E., and Lam, K. S. (1994) A Companion to Methods in Enzymolog 6, 381). Release of the peptide from the resin bead can then be carried out in sequential steps using different mechanism of cleavage. Release of the first part of peptide as a hydroxypropylamide is performed in buffer at pH 7–9. The release of the second part of the peptide is achieved by the use of higher pH (Scheme 1).

In the peptide libraries, polyethylene glycol-grafted polystyrene beads or TentaGel®S NH2 were used. In fact, any resin beads that are compatible with peptide synthesis and screening under aqueous conditions are adequate.

Penta-, hexa-, and heptamer library were prepared with one fixed position (L-asparagine). Glycine hydroxypropylamide on C-terminus is a part of a linker:

H-X4X3-Asn-X2X1-Gly-NH (CH2)3OH (2,160 peptides)

H-X5X4X3-Asn-X2X1-Gly-NH (CH2)3OH (25,920 peptides)

H-X6X5X4X3-Asn-X2X1-Gly-NH (CH2)3OH (311,040 peptides)

X1: N-Fmoc-L-amino acids (9) used in the first randomization: Valine, isoleucine, threonine, phenylalanine, β(2-naphthyl)alanine, 2-azetidinecarboxylic acid, proline, cyclohexylglycine, phenylglycine.

X2: N-Fmoc-L-amino acids (4) used in the second randomization: Alanine, glycine, serine, aspartic acid.

X3=X5=X6: N-Fmoc-L-amino acids (12) used in the third, fifth and sixth randomization: Pipecolic acid, β(2-naphthyl)alanine, glutamic acid, lysine, 2-azetidinecarboxylic acid, threonine, proline, asparagine, isoleucine, 3,5-diiodotyrosine, citrulline, arginine.

X4: N-Fmoc-L-amino acids (5) used in the fourth randomization: Aspartic acid, glutamic acid, 2-aminoadipic acid, O-sulfate tyrosine, γ-carboxyglutamic acid.

Resin (PEG-PS.HCl, Millipore®, 20 g, loading 0.58 mmol/g, 220 µm average particle size) was swollen in N,N-dimethylformamide for 2 hours and then neutralized with 10% N,N-diisopropylethylamine in dichloromethane. Resin was washed with dichloromethane and N,N-dimethylformamide. Linker (FIG. 1, 3 eq) was coupled using 1,3-diisopropylcarbodiimide and 1-hydroxybenzotriazole (3 eq each) in N,N-dimethylformamide at room temperature for 12 hours. The reaction was monitored by bromophenol blue method (Krchnak, V., Vagner, J., Safar, P., and Lebl, M. (1988) Collec.Czech.Cem. Commun.53, 2542). Completion of the coupling was then determined by a ninhydrin test (Kaiser, E., Colescott, R. L., Bossinger, C. D., and Cook, P. I. (1969) Anal. Biochem. 34, 595). After washing with N,N-dimethylformamide, Fmoc protecting group was removed with 50% piperidine in N,N-dimethylformamide for 15 min. Resin was then washed with N,N-dimethylformamide and the amount of released fulvene-piperidine adduct was quantitated by UV spectrometry (302 nm). A stable level of resin loading (mmol/g) determined in this manner throughout the library synthesis served as one of the quality control measures.

The resin was divided into 9 equal portions. Nine Fmoc-protected amino acids (X1) were then added separately into each of the resin aliquot and coupled by described procedure for 2 hours. The resin was then pooled in a cylindrical glass vessel fitted with a frit at the bottom. Dry nitrogen was bubbled through for mixing of the resin. Fmoc protecting group was removed as described above.

The resin was divided into 4 equal portions. Four Fmoc-protected amino acids (X2) were then added separately into each of the resin aliquot and coupled using the same coupling protocol. Fmoc protecting group was removed and resin loading was determined. In next cycle, L-asparagine was coupled by described-procedure. The resin was then divided into aliquots for another cycle of coupling. After all the randomization steps were completed, the Fmoc group was removed and the side chain protecting groups were cleaved with a mixture of trifluoroacetic acid (82.5%), anisole (5%), water (5%), thioanisole (5%), ethanedithiole (2.5%) during 2,5 hours. The resin was then washed with trifluoroacetic acid, dichloromethane, N,N-dimethylformamide and methanole. The libraries were stored dried at 4° C.

To verify the quality of the library, several randomly chosen beads were submitted for sequencing by Edman degradation and mass spectrometric techniques.

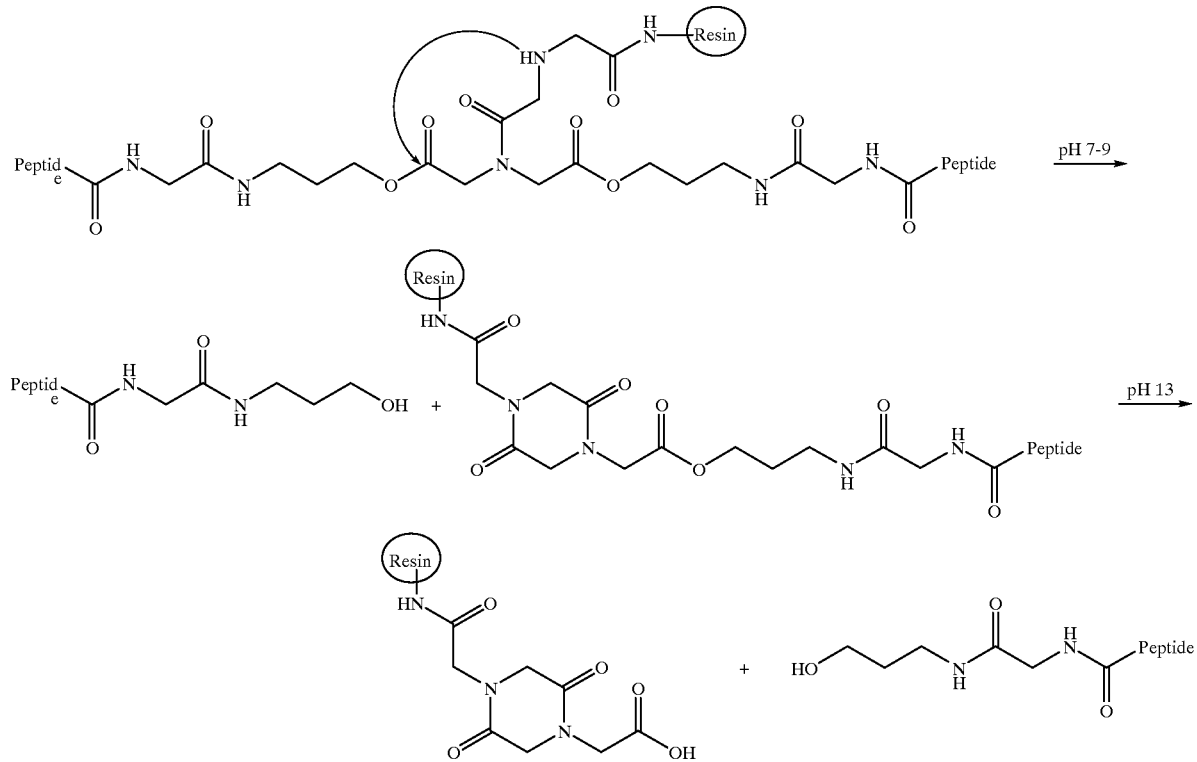

Scheme 1

1.3 Results (see also FIGS. 2–12)

| No | Mw | Purity | IC$_{50}$ [µM] | Structure |
|---|---|---|---|---|
| 1 Control | 855 | >95% | 3.9 | L-Asparaginyl-L-isoleucyl-L-aspartyl-L-prolyl-L-asparaginyl-L-alanyl-L-valyl-glycine-3-hydroxypropylamide<br>H-Asn-Ile-Asp-Pro-Asn-Ala-Val-Gly-NH(CH$_2$)$_3$OH (SEQ ID NO:8) |
| 2 Control | 628 | >95% | 7.7 | L-Aspartyl-L-prolyl-L-asparaginyl-L-alanyl-L-valyl-glycine-3-hydroxypropylamide<br>H-Asp-Pro-Asn-Ala-Val-Gly-NH(CH$_2$)$_3$OH (SEQ ID NO:9) |
| 3 | 772 | >95% | 0.51 | |

-continued

| No | Mw | Purity | IC$_{50}$ [μM] | Structure |
|---|---|---|---|---|
| | | | | H-Asp-Nal(2)-Asn-Asp-Val-Gly-NH(CH$_2$)$_3$OH<br>L-Aspartyl-L-3-(2-naphthyl)alanyl-L-asparaginyl-L-aspartyl-L-valyl-glycine-3-hydroxypropylamide (SEQ ID NO:10) |
| 4 | 744 | >95% | 0.38 | 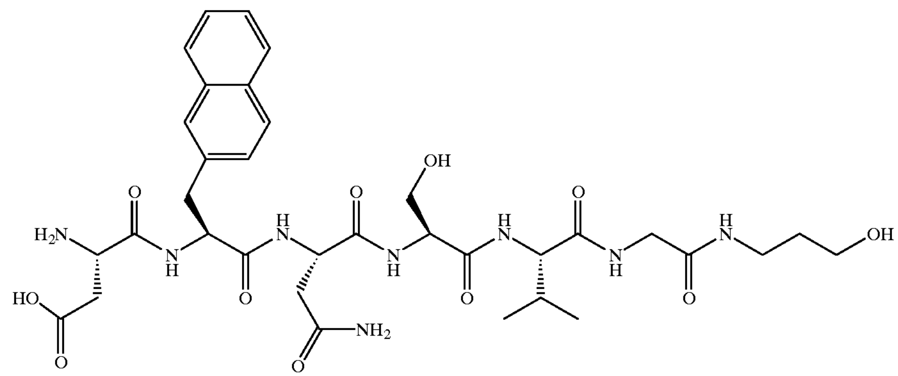 |
| | | | | H-Asp-Nal(2)-Asn-Ser-Val-Gly-NH(CH$_2$)$_3$OH<br>L-Aspartyl-L-3-(2-naphthyl)alanyl-L-asparaginyl-L-seryl-L-valyl-glycine-3-hydroxypropylamide (SEQ ID NO:11) |
| 5 | 728 | >95% | 0.75 | 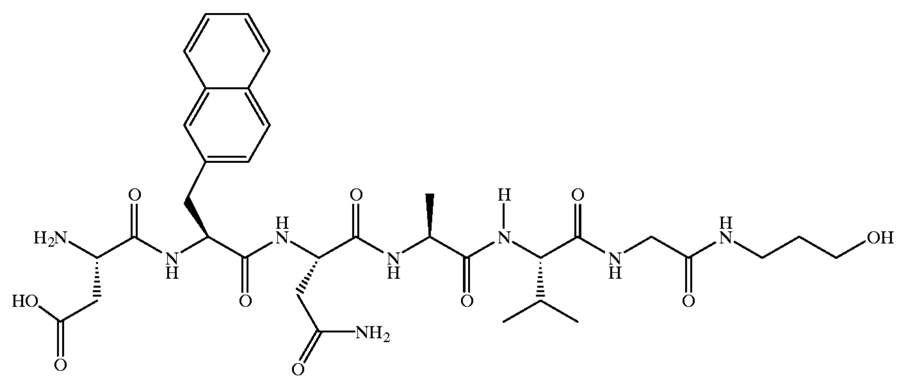 |
| | | | | H-Asp-Nal(2)-Asn-Ala-Val-Gly-NH(CH$_2$)$_3$OH<br>L-Aspartyl-L-3-(2-naphthyl)alanyl-L-asparaginyl-L-alanyl-L-valyl-glycine-3-hydroxypropylamide (SEQ ID NO:12) |

| No | Mw | Purity | IC$_{50}$ [μM] | Structure |
|---|---|---|---|---|
| 6 | 786 | >95% | 1.38 | 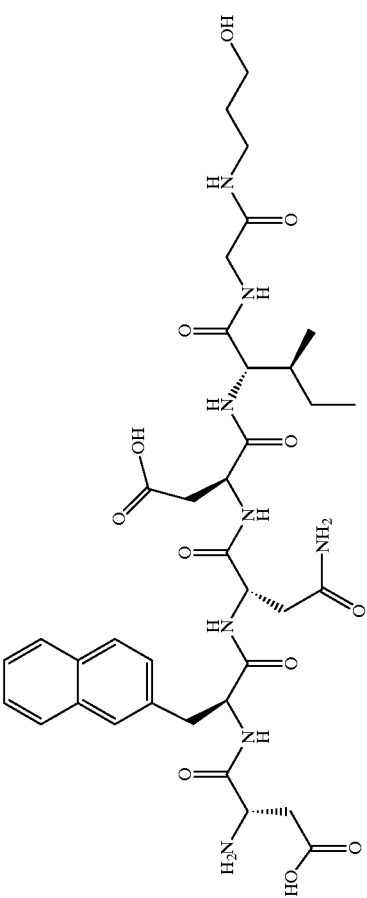 H-Asp-Nal(2)-Asn-Asp-Ile-Gly-NH(CH$_2$)$_3$OH<br>L-Aspartyl-L-3-(2-naphthyl)alanyl-L-asparaginyl-L-aspartyl-L-valyl-glycine-3-hydroxypropylamide (SEQ ID NO:13) |
| 7 | 758 | >95% | 0.6 | 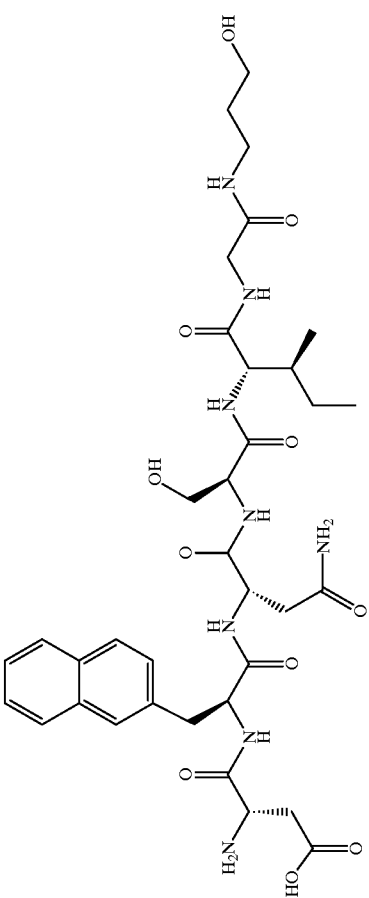 H-Asp-Nal(2)-Asn-Ser-Ile-Gly-NH(CH$_2$)$_3$OH<br>L-Aspartyl-L-3-(2-naphthyl)alanyl-L-asparaginyl-L-seryl-L-isoleucyl-glycine-3-hydroxypropylamide (SEQ ID NO:14) |

-continued
| No | Mw | Purity | IC$_{50}$ [µM] | Structure |
|---|---|---|---|---|
| 8 | 742 | >95% | 0.7 | 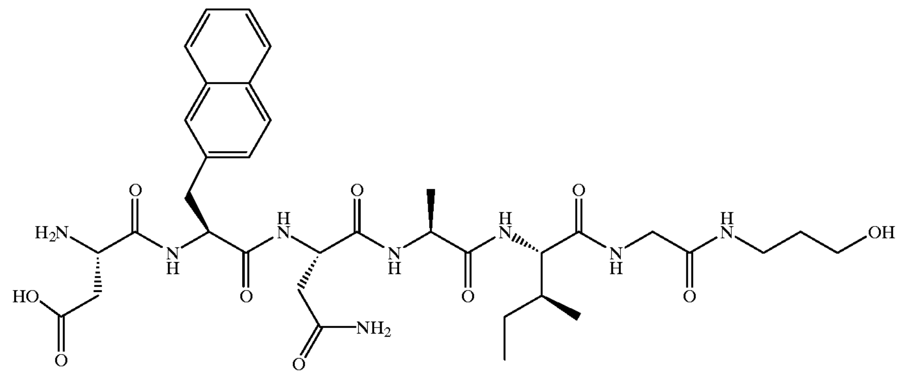 |
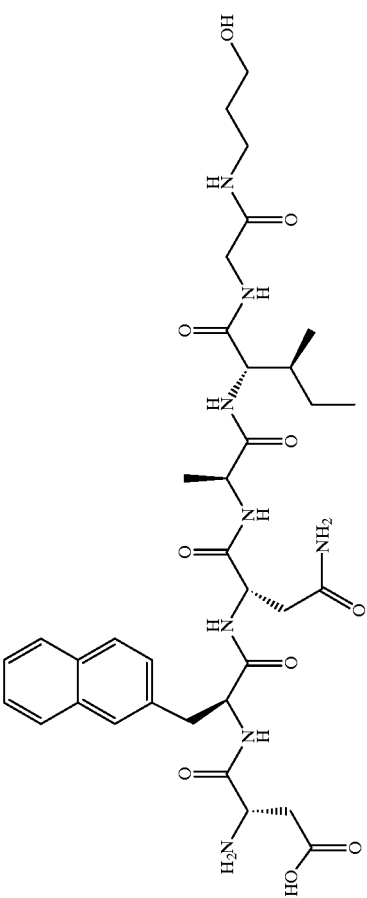
H-Asp-Nal(2)-Asn-Ala-Ile-Gly-NH(CH$_2$)$_3$OH
L-Aspartyl-L-3-(2-naphthyl)alanyl-L-asparaginyl-L-alanyl-L-isoleucyl-glycine-3-hydroxypropylamide (SEQ ID NO:15)
| No | Mw | Purity | IC$_{50}$ [µM] | Structure |
|---|---|---|---|---|
| 9 | 728 | >95% | 8.25 | |
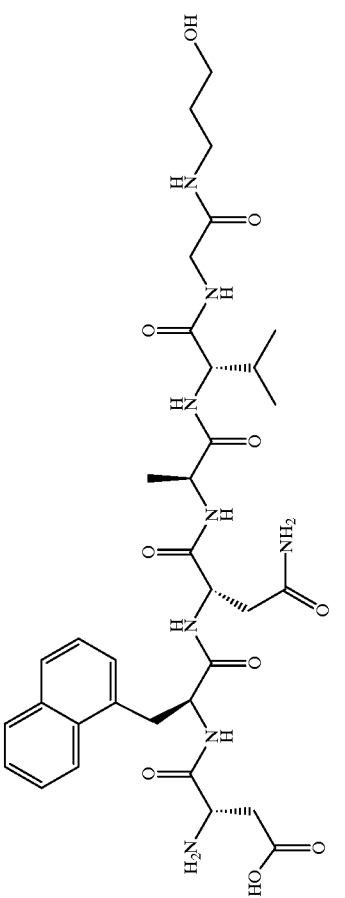
H-Asp-Nal(1)-Asn-Ala-Val-Gly-NH(CH$_2$)$_3$OH
L-Aspartyl-L-3-(1-naphthyl)alanyl-L-asparaginyl-L-alanyl-L-valyl-glycine-3-hydroxypropylamide (SEQ ID NO:16)

-continued
| No | Mw | Purity | IC$_{50}$ [μM] | Structure |
|----|-----|--------|----------------|-----------|
| 10 | 717 | >95% | 8.57 | 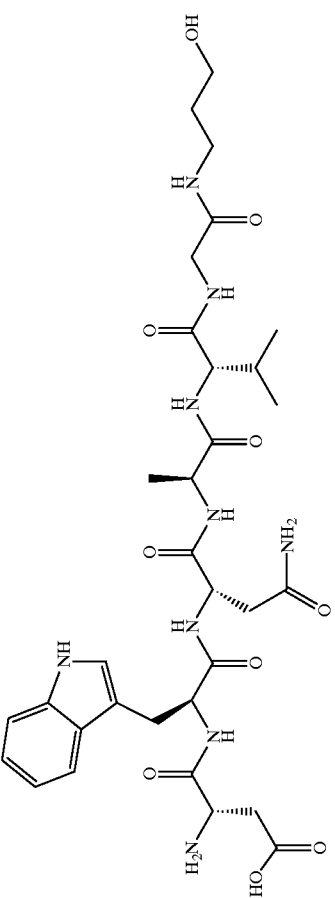 H-Asp-Trp-Asn-Ala-Val-Gly-NH(CH$_2$)$_3$OH L-Aspartyl-L-tryptophanyl-L-asparaginyl-L-alanyl-L-valyl-glycine-3-hydroxypropylamide (SEQ ID NO:17) |
| 11 | 678 | >95% | 3.38 | 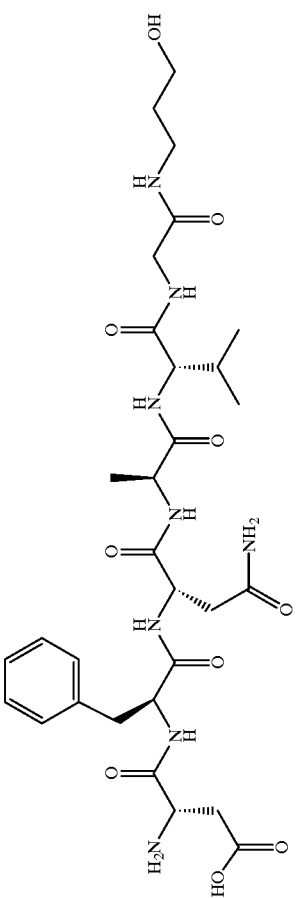 H-Asp-Phe-Asn-Ala-Val-Gly-NH(CH$_2$)$_3$OH L-Aspartyl-L-phenylalanyl-L-asparaginyl-L-alanyl-L-valyl-glycine-3-hydroxypropylamide (SEQ ID NO: 18) |

| No | Mw | Purity | IC$_{50}$ [μM] | Structure |
|---|---|---|---|---|
| 12 | 694 | >95% | 3.79 | H-Asp-Tyr-Asn-Ala-Val-Gly-NH(CH$_2$)$_3$OH<br>L-Aspartyl-L-tyrosyl-L-asparaginyl-L-alanyl-L-valyl-glycine-3-hydroxypropylamide (SEQ ID NO:19) |
| 13 | 734 | >95% | 7.03 | H-Asp-Ala[3-(3-Benzothienyl)]-Asn-Ala-Val-Gly-NH(CH$_2$)$_3$OH<br>L-Aspartyl-L-3-(3-benzothienyl)alanyl-L-asparaginyl-L-alanyl-L-valyl-glycine-3-hydroxypropylamide (SEQ ID NO:20) |

-continued

| No | Mw | Purity | IC$_{50}$ [μM] | Structure |
|---|---|---|---|---|
| 14 | 754 | >95% | 0.94 | 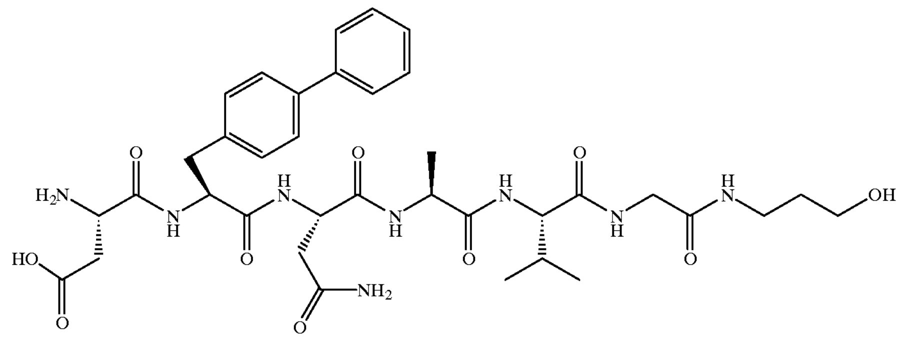 |

H-Asp-Ala[3-(4-Biphenyl)]-Asn-Ala-Val-Gly-NH(CH$_2$)$_3$OH

L-Aspartyl-L-3-(4-biphenyl)alanyl-L-asparaginyl-L-alanyl-L-valyl-glycine-3-hydroxypropylamide (SEQ ID NO:21)

| 15 | 754 | >95% | 26.3 | |

H-Asp-Ala(3,3-Diphenyl)-Asn-Ala-Val-Gly-NH(CH$_2$)$_3$OH

L-Aspartyl-L-(3,3-diphenyl)alanyl-L-asparaginyl-L-alanyl-L-valyl-glycine-3-hydroxypropylamide (SEQ ID NO:22)

| No | Mw | Purity | IC$_{50}$ [μM] | Structure |
|---|---|---|---|---|
| 16 | 720 | 50–75% | 4.28 | L-Aspartyl-L-(3S)-phenylprolyl-L-asparaginyl-L-seryl-L-valyl-glycine-3-hydroxypropylamide<br>H-Asp-Pro[(3S)-Phenyl]-Asn-Ser-Val-Gly-NH(CH$_2$)$_3$OH (SEQ ID NO:23) |
| 17 | 720 | 50–75% | 2.27 | L-Aspartyl-L-(3R)-phenylprolyl-L-asparaginyl-L-seryl-L-valyl-glycine-3-hydroxypropylamide<br>H-Asp-Pro[(3R)-Phenyl]-Asn-Ser-Val-Gly-NH(CH$_2$)$_3$OH (SEQ ID NO:24) |

-continued

| No | Mw | Purity | IC$_{50}$ [μM] | Structure |
|---|---|---|---|---|
| 18 | 695 | 50–75% | 25 | 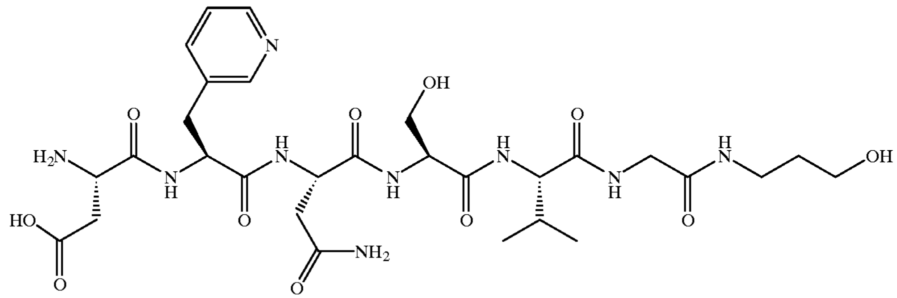 |

L-Aspartyl-L-3-(3-pyridyl)alanyl-L-asparaginyl-L-seryl-L-valyl-glycine-3-hydroxypropylamide
H-Asp-Ala[3-(3-pyridyl)-Asn-Ser-Val-Gly-NH(CH2)3OH (SEQ ID NO:25)

| 19 | 744 | 75–95% | 25 | |

L-Aspartyl-D-3-(2-naphthyl)alanyl-L-asparaginyl-L-seryl-L-valyl-glycine-3-hydroxypropylamide
H-Asp-nal(2)-Asn-Ser-Val-Gly-NH(CH2)3OH (SEQ ID NO:26)

-continued
| No | Mw | Purity | IC$_{50}$ [μM] | Structure |
|---|---|---|---|---|
| 20 | 708 | 50–75% | 32.5 | H-Asp-Hof-Asn-Ser-Val-Gly-NH(CH2)3OH<br>L-Aspartyl-L-homophenylalanyl-L-asparaginyl-L-seryl-L-valyl-glycine-3-hydroxypropylamide (SEQ ID NO:27) |
| 21 | 686 | 75–95% | 0.34 | H-Asp-Nal(2)-Asn-Ser-Val-Gly-NH2<br>L-Aspartyl-L-3-(2-naphthyl)alanyl-L-asparaginyl-L-seryl-L-valyl-glycine-amide (SEQ ID NO:28) |
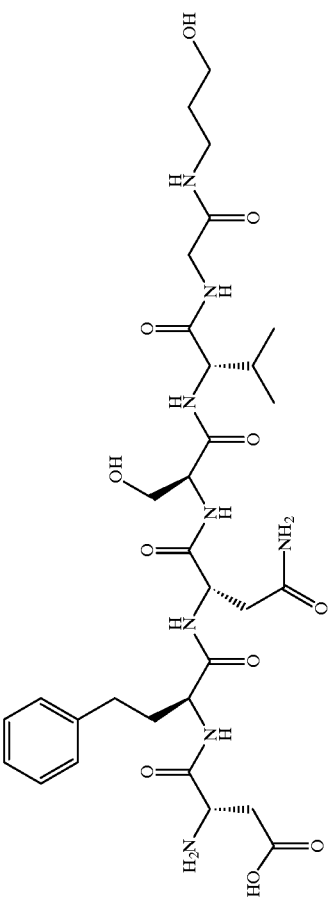
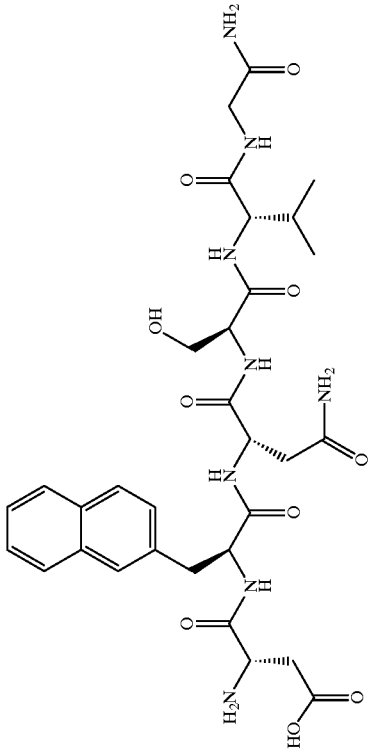

-continued

| No | Mw | Purity | IC$_{50}$ [μM] | Structure |
|---|---|---|---|---|
| 22 | 629 | 75–95% | 0.18 | H-Asp-Nal(2)-Asn-Ser-Val-NH2<br>L-Aspartyl-L-3-(2-naphthyl)alanyl-L-asparaginyl-L-seryl-L-valine-amide (SEQ ID NO:29) |
| 23 | 777 | 50–75% | 1.49 | Phthalyl-Nal(2)-Asn-Ser-Val-Gly-NH(CH2)3OH<br>Phthaloyl-L-3-(2-naphthyl)alanyl-L-asparaginyl-L-seryl-L-valyl-glycine-3-hydroxypropylamide (SEQ ID NO:30) |

-continued

| No | Mw | Purity | IC$_{50}$ [μM] | Structure |
|---|---|---|---|---|
| 24 | 729 | >95% | 0.39 | See Example 2.3 |

Succinyl-L-3-(2-naphthyl)alanyl-L-asparaginyl-L-seryl-L-valyl-glycine-3-hydroxypropylamide
Suc-Nal(2)-Asn-Ser-Val-Gly-NH(CH2)3OH (SEQ ID NO:31)

| No | Mw | Purity | IC$_{50}$ [μM] | Structure |
|---|---|---|---|---|
| 25 | 744 | 75–95% | 0.23 | |

L-β-Aspartyl-L-3-(2-naphthyl)alanyl-L-asparaginyl-L-seryl-L-valyl-glycine-3-hydroxypropylamide
H-βAsp-Nal(2)-Asn-Ser-Val-Gly-NH(CH2)3OH (SEQ ID NO:32)

-continued

| No | Mw | Purity | IC$_{50}$ [μM] | Structure |
|---|---|---|---|---|
| 26 | 743 | 75–95% | 0.45 | Glutaryl-Nal(2)-Asn-Ser-Val-Gly-NH(CH$_2$)$_3$OH<br>Glutaryl-L-3-(2-naphthyl)alanyl-L-asparaginyl-L-seryl-L-valyl-glycine-3-hydroxypropylamide (SEQ ID NO:33) |
| 27 | 901 | >95% | 0.44 | H-Cit-Asp-Nal(2)-Asn-Ser-Val-Gly-NH(CH$_2$)$_3$OH<br>L-Citrulyl-L-aspartyl-L-3-(2-naphthyl)alanyl-L-asparaginyl-L-seryl-L-valyl-glycine-3-hydroxypropylamide (SEQ ID NO:34) |

| No | Mw | Purity | IC$_{50}$ [μM] | Structure |
|----|-----|--------|----------------|-----------|
| 28 | 900 | 75–95% | 0.15 | 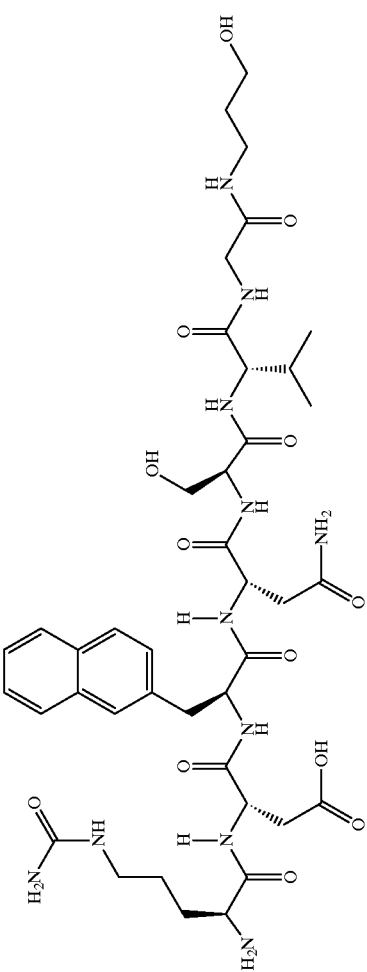 H-Arg-Asp-Nal(2)-Asn-Ser-Val-Gly-NH(CH$_2$)$_3$OH<br>L-Arginyl-L-aspartyl-L-3-(2-naphthyl)alanyl-L-asparaginyl-L-seryl-L-valyl-glycine-3-hydroxypropylamide (SEQ ID NO:35) |
| 29 | 872 | >95% | 0.24 | 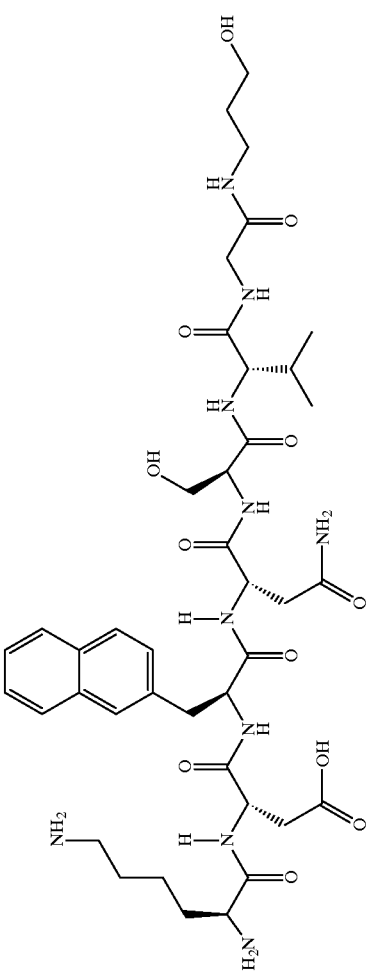 H-Lys-Asp-Nal(2)-Asn-Ser-Val-Gly-NH(CH$_2$)$_3$OH<br>L-Lysyl-L-aspartyl-L-3-(2-naphthyl)alanyl-L-asparaginyl-L-seryl-L-valyl-glycine-3-hydroxypropylamide (SEQ ID NO:36) |

-continued

| No | Mw | Purity | IC$_{50}$ [μM] | Structure |
|---|---|---|---|---|
| 30 | 713 | >95% | 0.25 | Suc-Nal(2)-Asn-Ala-Val-Gly-NH(CH2)3OH<br>Succinyl-L-3-(2-naphthyl)alanyl-L-asparaginyl-L-alanyl-L-valyl-glycine-3-hydroxypropylamide (SEQ ID NO:37) |
| 31 | 598 | >95% | 0.19 | Suc-Nal(2)-Asn-Ala-Val-NH2<br>Succinyl-L-3-(2-naphthyl)alanyl-L-asparaginyl-L-alanyl-L-valine-amide (SEQ ID NO:38) | see example 3.1

-continued

| No | Mw | Purity | IC$_{50}$ [μM] | Structure |
|---|---|---|---|---|
| 32 | 612 | >95% | 0.17 | Succinyl-L-3-(2-naphthyl)alanyl-L-asparaginyl-L-alanyl-L-2-tert.butyl-glycine-amide (SEQ ID NO:39)<br>Suc-Nal(2)-Asn-Ala-Gly(2-tBu)-NH2 |
| 33 | 584 | >95% | 0.72 | Succinyl-L-3-(2-naphthyl)alanyl-L-asparaginyl-glycinyl-L-valine-amide (SEQ ID NO:40)<br>Suc-Nal(2)-Asn-Gly-Val-NH2 |

-continued
| No | Mw | Purity | IC$_{50}$ [µM] | Structure |
|---|---|---|---|---|
| 34 | 624 | >95% | 0.027 | See Example 2.2 |
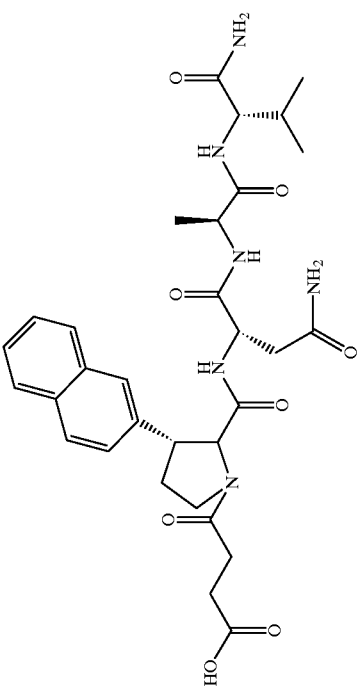
Suc-Pro[(3R)-2-Naphthyl]-Asn-Ala-Val-NH2
Succinyl-L-(3R)-(2-naphthyl)prolyl-L-asparaginyl-L-alanyl-L-valine-amide (SEQ ID NO:41)
| 35 | 654 | >95% | 5.02 | |
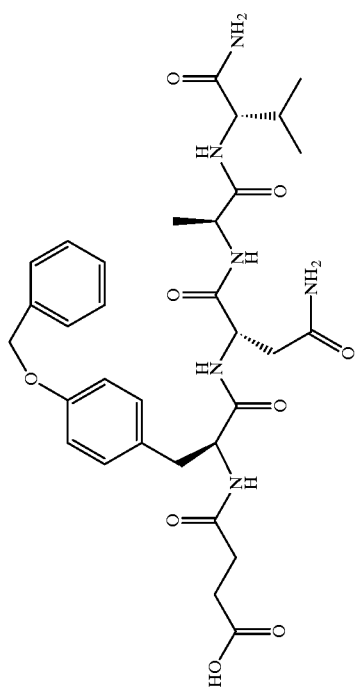
Suc-Tyr(Bzl)-Asn-Ala-Val-NH2
Succinyl-L-O-benzyl-tyrosyl-L-asparaginyl-L-alanyl-L-valine-amide (SEQ ID NO:42)

-continued
| No | Mw | Purity | IC$_{50}$ [μM] | Structure |
|---|---|---|---|---|
| 36 | 624 | >95% | 2.83 | Succinyl-L-3-(4-biphenyl)alanyl-L-asparaginyl-L-alanyl-L-valine-amide (SEQ ID NO:43)<br>Suc-Ala[3-(4-Biphenyl)]-Asn-Ala-Val-NH2 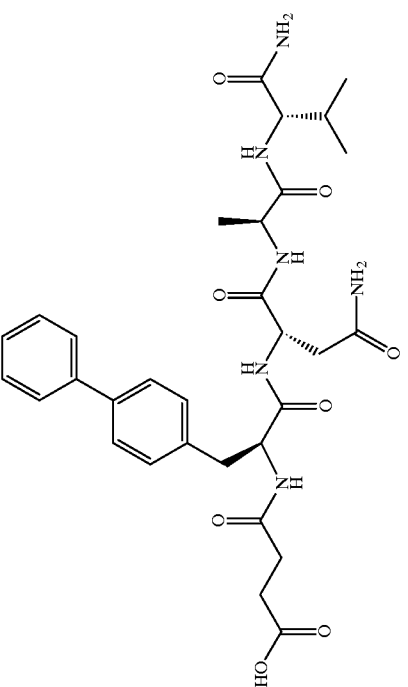 |
| 37 | 599 | >95% | 0.83 | Succinyl-L-3-(2-Naphthyl)alanyl-L-asparaginyl-L-alanyl-L-valine (SEQ ID NO:44)<br>Suc-Nal(2)-Asn-Ala-Val-OH 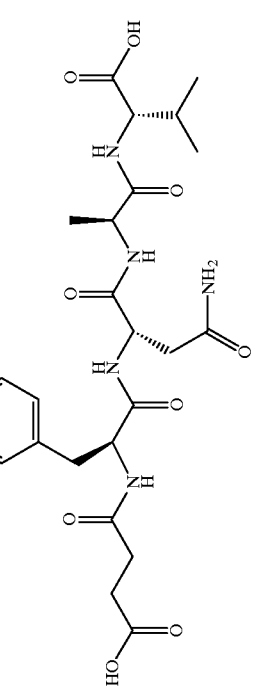 |

-continued
| No | Mw | Purity | IC$_{50}$ [μM] | Structure |
|---|---|---|---|---|
| 38 | 585 | >95% | 0.26 | Succinyl-L-3-(2-Naphthyl)alanyl-L-asparaginyl-L-alaninyl-L-valinol<br>Suc-Nal(2)-Asn-Ala-Val-ol (SEQ ID NO:45) |
| 39 | 597 | >95% | 1.5 | Succinyl-L-3-(2-Naphthyl)alanyl-L-asparaginyl-L-alanine-2,4-dimethylpentylamide<br>Suc-Nal(2)-Asn-Ala-NHCH(ipr)2 (SEQ ID NO:46) |
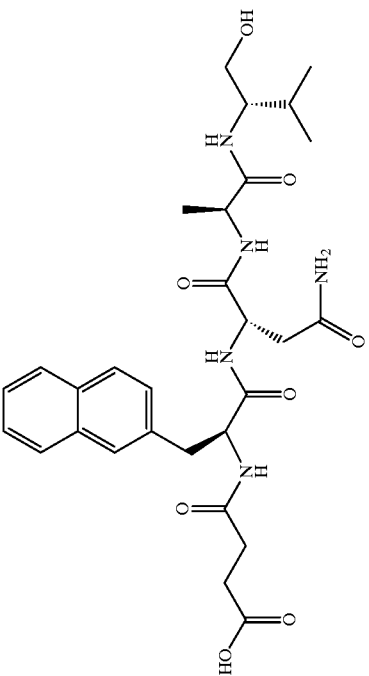
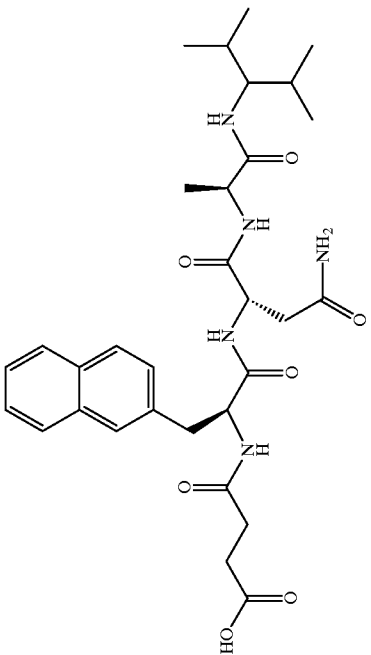

-continued

| No | Mw | Purity | IC$_{50}$ [μM] | Structure |
|---|---|---|---|---|
| 40 | 569 | >95% | 1.16 | Suc-Nal(2)-Asn-Ala-NHCH2C(CH3)3<br>Succinyl-L-3-(2-Naphthyl)alanyl-L-asparaginyl-L-alanine-neopentylamide (SEQ ID NO:47) |
| 41 | 595 | >95% | 8.17 | Suc-Nal(2)-Asn-Ala-3,3-dimethylpiperidine<br>Succinyl-L-3-(2-Naphthyl)alanyl-L-asparaginyl-L-alanine-3,3-dimethylpiperidinylamide (SEQ ID NO:48) |

-continued

| No | Mw | Purity | IC$_{50}$ [μM] | Structure |
|---|---|---|---|---|
| 42 | 626 | 75–95% | 0.24 | Succinyl-L-3-(2-Naphthyl)alanyl-L-asparaginyl-L-alanyl-L-valine-dimethylamide (SEQ ID NO:49)<br>Suc-Nal(2)-Asn-Ala-Val-N(CH3)2 |
| 43 | 611 | >95% | 0.026 | Succinyl-L-(3R)-(2-naphthyl)prolyl-L-asparaginyl-L-alanyl-(2S)-amino-3-methyl-1-butanol (SEQ ID NO:50)<br>Suc-Pro[(3R)-2-Naphthyl]-Asn-Ala-Val-ol |

2. Large scale synthesis

2.1 Synthesis of N-Fmoc-trans-3-(2'-naphthyl)-L-proline (A8)

Summary: N-Fmoc-trans-3-(2'-naphthyl)-L-proline (A8) was prepared in 10 steps:

2.1.2 trans-3-(2'-Naphthyl)-propenoic acid (A2)

To a solution of ester A1 (4.24 g, 18.8 mmol) in THF (75 mL) was added LiOH.H$_2$O (2.36 g, 56.3 mmol) in water (19 mL). The initially heterogenous mixture was stirred vigorously overnight and became homogenous. The reaction

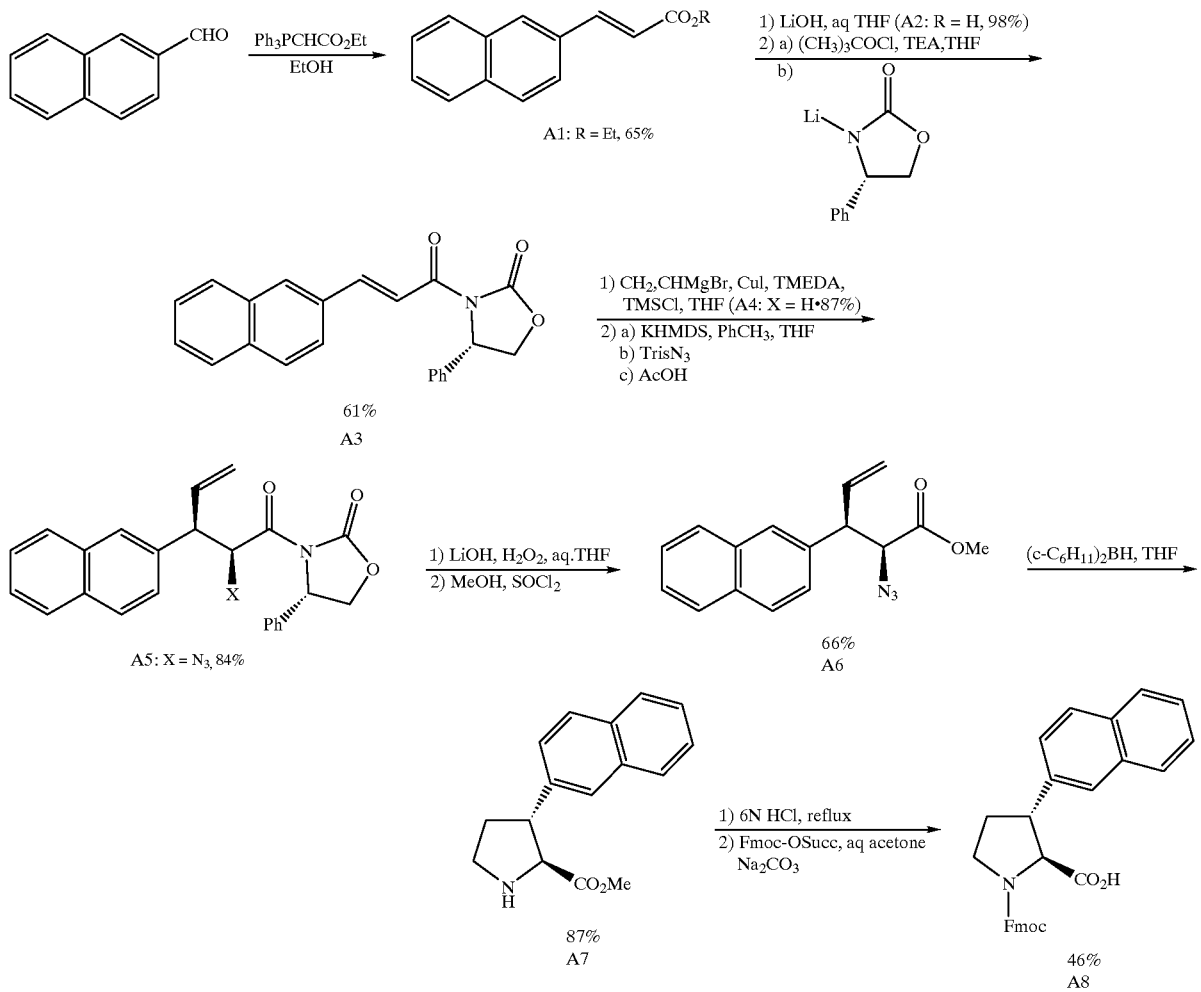

2.1.1 Ethyl trans-3-(2'-naphthyl)-propenoate (A1)

To a stirred solution of 2-naphthaldehyde (7.8 g, 50 mmol) in 50 mL ethanol was added (carbethoxymethylene)triphenylphosphorane (18.3 g, 52.5 mmol). A slight exotherm was noted. A precipitate formed while the mixture stirred overnight. The reaction mixture was diluted with Et$_2$O (500 mL) and washed with 1 M H$_3$PO$_4$ (2×100 mL), saturated NaHCO$_3$ (1×100 mL), water (100 mL), and brine (100 mL). The organic fraction was dried (MgSO$_4$) and concentrated under reduced pressure. The residue was passed through a SiO$_2$ plug eluting with 9:1 hexane:EtOAc. After concentration in vacuo, a near quantitative yield of the product as an 85:15 mixture of geometric isomers (favoring trans, nmr) was recovered. The material was recrystallized from hexane/EtOAc (rich in hexane) to recover 4.5 g of the desired product as a 97:3 mixture of isomers (nmr). The mother liquor was concentrated and recrystallized as before to recover an additional 2.9 g (total 7.4 g, 33 mmol, 65% yield). NMR (CDCl$_3$) δ 7.93 (s, 1 H); 7.88–7.83 (c, 4 H); 7.67 (dd, 1 H, J=1.6, 8.6 Hz); 7.53–7.50 (c, 2 H); 6.55 (d, 1 H, J=16.0 Hz); 4.30 (q, 2 H, J=7.1 Hz); 1.42 (t, 3 H, J=7.1 Hz).

mixture was acidified with concentrated HCl (pH≈2) and a precipitate formed. The heterogenous mixture was transferred to a separatory funnel and extracted with EtOAc (3×150 mL). The combined extracts were dried (MgSO$_4$) and concentrated in vacuo to recover the carboxylic acid as a white solid (3.66 g, 98% yield). NMR (CDCl$_3$) δ 7.97 (d, 1 H, J=15.7 Hz); 7.90 (d, 1 H. J=15.3 Hz); 7.90–7.83 (c, 3 H); 7.70 (dd, 1 H, J=1.6, 8.6 Hz); 7.57–7.50 (c, 2 H); 6.58 (d, 1 H, J=16.0 Hz).

2.1.3 trans-(4S)-3-(3'-(2"-Naphthyl)-propenoyl)4-phenyl-2-oxazolidinone (A3)

A solution of carboxylic acid A2 (3.66 g, 18.5 mmol) and triethylamine (1.87 g, 2.56 mL, 18.5 mmol) in anhydrous THF (74 mL) was cooled to −78° C. Pivaloyl chloride (2.35 g, 2.40 mL, 19.4 mmol) was added over two minutes accompanied by formation of a white precipitate. After 10 minutes, the flask was placed in a 0° C. bath for a duration of 10 minutes after which the flask cooled back to −78° C. for 1.5 h. In a separate flask the oxazolidione derived from L-phenylglycinol (3.31 g, 20.3 mmol) in anhydrous THF (74 mL) was cooled to −78° C. A solution of n-BuLi (1.6 M in hexane, 11.6 mL, 18.5 mmol) was added and stirring continued for about 1 h accompanied by the metalated oxazolidinone precipitating from the THF/hexane solution. The mixed anhydride was added via cannula to the metallated oxazolidinone and the reaction mixture placed in a 0° bath. After 1 h the bath was removed and the mixture warmed to room temperature overnight. The reaction was quenched with 50 mL saturated $NH_4Cl$. THF was removed under reduced pressure and, after transfer to a separatory funnel, the mixture was extracted with $CH_2Cl_2$ (3×75 mL). The combined organic fractions were washed with 1 M NaOH (2×50 mL), dried ($MgSO_4$) and concentrated. The residue was recrystallized from EtOAc/hexane to recover a white solid (3.87 g, 11.2 mmol, 61% yield). NMR ($CDCl_3$) δ 8.05 (d, 1 H, J=15.7 Hz); 7.94 (d, 1 H, J=15.4 Hz); 7.87–7.81 (c, 3 H); 7.76 (dd, 1 H, J=1.5, 8.6 Hz); 7.53–7.47 (c, 2 H); 7.41–7.34 (c, 5 H); 5.58 (dd, 1 H, J=8.7, 3.9 Hz); 4.76 (t, 1 H, J=8.7 Hz); 4.33 (dd, 1 H, J=8.8, 3.9 Hz).

2.1.4 (3'R4S)-3-(3'-(2"-Naphthyl)-4'-pentenoyl)4-phenyl-2-oxazolidinone (A4)

To a solution of CuI (3.96 g, 20.9 mmol) and TMEDA (2.66 g, 3.46 mL, 22.9 mmol) in anhydrous THF (92 mL) at −78° C. was added vinylmagnesium bromide (1.0 M in THF, 20.9 mL, 20.9 mmol). The mixture was stirred for 15 minutes. In a separate flask trimethylsilyl chloride (5.69 g, 6.64 mL, 52.2 mmol) was added to a solution of unsaturated imide A3 (3.87 g, 11.3 mmol) in anhydrous THF (42 mL). Owing to insolubility of the imide, the septum of the flask containing the cuprate reagent was removed and the slurried imide added in one portion rinsing quickly with a small amount of THF. The bath temperature was raised to −30° C. and stirring continued for 1 h. The reaction mixture was poured into 250 mL of a 3:2 mixture of saturated $NH_4Cl$:concentrated $NH_4OH$. The layers were separated and the aqueous fraction extracted with EtOAc (3×200 mL). The combined organic fractions were washed sequentially with saturated $NH_4Cl$ (1×100 mL) and water (1×100 mL). The organic fraction was dried ($MgSO_4$) and concentrated under reduced pressure. The residue was purified by passage through a plug of $SiO_2$ eluting with 4:1 hexane:EtOAc. The eluant was concentrated in vacuo to recover a white solid (3.64 g, 9.81 mmol, 87% yield). NMR ($CDCl_3$) δ 7.87–7.82 (c, 3 H); 7.72 (s, 1 H); 7.54–7.27 (c, 8 H); 6.11 (ddd, 1 H, J=6.7, 10.4, 17.0 Hz); 5.34 (dd, 1 H, J=8.6, 3.5 Hz); 5.10 (d, H, J=8.2 Hz); 5.08 (d, 1 H, J=17.2 Hz); 4.56 (t, 1 H, J=8.8 Hz); 4.26 (dd, 1 H, J=8.8, 3.5 Hz); 4.16 (ddd, 1 H, J=8.1, 7.0, 6.9 Hz); 3.68 (dd, 1 H, J=8.4, 16.5 Hz); 3.50 (dd, 1 H, J=6.5, 16.5 Hz).

2.1.5 (2'S3'R4S)-3-(2'-Azido-3'-(2"-naphthyl)-4'-pentenoyl)-4-phenyl-2-oxazolidinone (A5)

Potassium hexamethyldisilazide (0.5 M in toluene, 25.5 mL, 12.8 mmol) was added in one portion to anhydrous THF (34 mL) at −78° C. Imide A4 (3.64 g, 9.81 mmol) was slurried in THF (34 mL) and added via cannula, rinsing with THF (2×11 mL) to complete the transfer. After 30 min, trisylazide (4.40 g, 14.2 mmol) was dissolved in THF (34 mL), cooled to −78° C., and added via cannula. Thirty minutes later, AcOH (1.41 g, 1.34 mL, 23.4 mmol) was added to quench the reaction. The mixture was stirred at room temperature overnight. The mixture was partitioned between $CH_2Cl_2$ (300 mL) and dilute brine (150 mL). The layers were separated and the aqueous phase extracted with $CH_2Cl_2$ (3×150 mL). The combined organic fractions were dried ($MgSO_4$) and concentrated under reduced pressure. The residue was purified by flash chromatography to recover the product (3.41 g, 8.28 mmol, 84% yield). NMR ($CDCl_3$) δ 7.85–7.82 (c, 3 H); 7.72 (s, 1 H); 7.53–7.47 (c, 2 H); 7.42 (dd, 1 H, J=1.7, 8.5 Hz); 7.37–7.31 (c, 3 H); 7.18–7.15 (c, 2 H); 6.28 (ddd, 1 H, J=8.2, 10.2, 17.1 Hz); 5.63 (d, 1 H, J=10.2 Hz); 5.37 (d, 1 H, J=17.0 Hz); 5.34 (d, 1 H, J=10.2 Hz); 4.83 (dd, 1 H, J=3.0, 8.3 Hz); 4.14 (t, 1 H, J=7.2 Hz); 4.07 (dd, 1 H, J=9.3, 17.9 Hz); 3.94 (dd, 1 H, J=3.0, 5.8 Hz); 3.68 (t, 1 H, J=8.6 Hz).

2.1.6 Methyl (2S3R)-2-Azido-3-(2'-naphthyl)-4pentenoate (A6)

To a solution of imide A5 (3.41 g, 8.28 mmol) in THF (62 mL) was added water (21 mL), 35% $H_2O_2$ (2.7 mL), and $LiOH.H_2O$ (695 mg, 16.6 mmol). After 2 hours $Na_2SO_3$ (4.17 g, 33.1 mmol) was added as a solution in water (41 mL). The mixture was stirred for 15 minutes and THF removed under reduced pressure. The aqueous solution was acidified with HCl and extracted with EtOAc (2×150 mL). The combined extracts were dried ($MgSO_4$) and concentrated under reduced pressure. The residue was passed through a $SiO_2$ plug column eluting with 1:1 hexane:EtOAc to recover, after concentration, a white solid that was presumably a mixture of the carboxylic acid and chiral auxiliary. Recrystallization from hexane/EtOAc yielded the chiral auxiliary as needles. The mother liquor was concentrated and carried on to the esterification step. The residue containing the crude carboxylic acid was dissolved in anhydrous MeOH (46 mL) and cooled to 0° C. Thionyl chloride (1.18 g, 725 μL, 9.94 mmol) was added and, after 10 minutes, the mixture heated at reflux for 2 hours. Water (1.0 mL) was added to the mixture, stirred for 10 minutes, and the contents of the flask concentrated under reduced pressure. The residue was partitioned between EtOAc (150 mL) and brine (100 mL). The layers were separated and the organic fraction was dried ($MgSO_4$) and concentrated under reduced pressure. The residue was purified by flash chromatography (19:1 hexane:EtOAc) to recover the methyl ester (1.54 g, 5.48 mmol, 66% yield). NMR ($CDCl_3$) δ 7.84–7.80 (c, 3 H); 7.71 (s, 1 H); 7.50–7.46 (c, 2 H); 7.39 (dd, 1 H, J=1.8, 8.5 Hz); 6.23 (ddd, 1 H, J=8.3, 10.9, 17.6 Hz); 5.30 (d, 1 H, J=9.9 Hz); 5.28 (d, 1 H, J=17.7 Hz); 4.22 (d, 1 H, J=7.5 Hz); 4.06 (t, 1 H, J=7.9 Hz).

2.1.7 trans-3-(2'-naphthyl)-L-proline methyl ester (A7)

Borane-methyl sulfide complex (2.0 M in THF, 6.57 mL, 13.1 mmol) was diluted with anhydrous THF (26 mL) and cooled to 0° C. Cyclohexene (2.16 g, 2.66 mL, 26.3 mmol) was added cautiously via syringe. After 30 minutes a white precipitate had formed. Stirring was continued for three hours. The contents of the flask were concentrated in vacuo. The reagent was slurried in $CH_2Cl_2$ (36 mL) and cooled to 0° C. Vinyl azide A6 (1.23 g, 4.38 mmol) was dissolved in $CH_2Cl_2$ (9 mL) and added via cannula. The reaction mixture became pale yellow and gas evolution was evident.

The mixture was warmed to room temperature overnight. Added MeOH (26 mL) and stirred for an additional 15 minutes. The mixture was concentrated under reduced pressure. The residue was taken up in $Et_2O$ (25 mL) and extracted with 0.1 M HCl (5×25 mL). The aqueous extracts were basicified with saturated $NaHCO_3$ and extracted with $CH_2Cl_2$ (3×100 mL). The organic extracts were dried ($MgSO_4$) and concentrated in vacuo to recover the cyclized product along with some dicyclohexyl borane derived contaminants (974 mg, 3.82 mmol, 87% yield of crude material). NMR ($CDCl_3$) δ 7.84–7.78 (c, 3 H); 7.71 (s, 1 H); 7.49–7.41 (c, 3 H); 3.91 (d, 1 H, J=6.9 Hz); 3.69 (s, 3 H); 3.63 (m, 1 H), 3.48 (dd, 1 H, J=8.2, 15.4 Hz); 3.27 (d, 1 H, J=7.8 Hz); 3.25 (d, 1 H, J=7.8 Hz); 2.33 (m, 1 H), 2.09 (m, 1 H).

2.1.8 N-Fmoc-trans-3-(2'-naphthyl)-L-proline (A8)

510 mg (2 mmol) of methyl ester (A7) in 12 ml of 6N HCl are heated 100° C. for 10 hours. The reaction solution is concentrated under reduced pressure and the solid residue is suspended in 15 ml of acetone. The suspension is adjusted to pH 9–10 using 2N $Na_2CO_3$ solution. 742 mg (2.2 mmol) of Fmoc-O-succinimide are then added slowly. The pH is subsequently adjusted to 9–10 and the mixture is stirred at room temperature for 4 hours and then allowed to stand at room temperature overnight. The pH is subsequently adjusted to 2 using conc. HCl, and the mixture is admixed with ethyl acetate. 560 mg of the precipitated product are filtered off with suction. The aqueous phase is extracted three times with ethyl acetate and subsequently admixed with methylene chloride. This gives a further 185 mg of product as a precipitate. Yield:745 mg (80.4%). NMR (d6-DMSO) δ 7.95–7.80 (c, 6 H); 7.68 (d, 1 H, J=7.3 Hz); 7.60 (d, 1 H, J=7.4 Hz); 7.50–7.34 (c, 6 H); 7.25 (m, 1 H), 4.39–4.15 (c, 4 H); 3.70–3.48 (c, 3 H); 2.29 (m, 1 H); 2.14 (m, 1 H).

2.2 N-Succinyl-trans-3-(2'-naphthyl)-L-prolyl-L-asparaginyl-L-alaninyl-L-valine-amide (SEQ ID NO:41) (34)

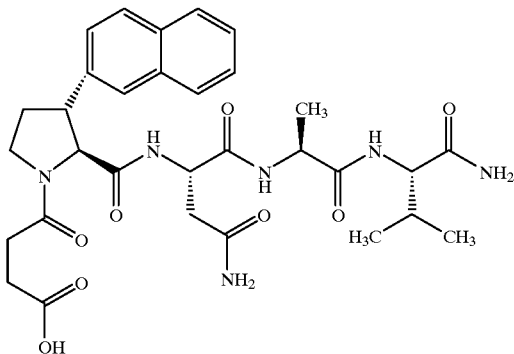

34

2.2.1 N-Fmoc-trans-3-(2'-naphthyl)-L-proline-L-asparagine-L-alanine-L-valine-amide (SEQ ID NO:41) (B1)

463.5 mg (1 mmol) of N-Fmoc-trans-3-(2'-naphthyl)-L-proline (A8), 338 mg of H-Asn-Ala-Val-$NH_2$ hydrochloride (prepared according to customary methods of peptide chemistry) and 135 mg of HOBT are dissolved in 20 ml of DMF. At 0° C., 0.13 ml of N-ethylmorpholine and 220 mg of DCC are added. The mixture is stirred at 0° C. for 1 hour and then at room temperature for 3 hours and is subsequently allowed to stand at room temperature overnight. The precipitate is filtered off with suction and the solution is concentrated under high vacuum. The residue is partitioned between pentanol and $NaHCO_3$ solution. The pentanol phase is washed with $KHSO_4$ solution and $H_2O$/NaCl solution. The precipitate is filtered off with suction and thoroughly triturated with diethyl ether. This gives 473 mg of product. The pentanol phase is dried using $Na_2SO_4$ and concentrated. The residue is triturated twice with diethyl ether. This gives another 257 mg of product.

Yield: 730 mg (97.7%).

2.2.2 trans-3-(2'-Naphthyl)-L-proline-L-asparagine-L-alanine-L-valine-amide (SEQ ID NO:41) (B2).

248 mg (0.332 mmol) of N-Fmoc-trans-3-(2'-naphthyl)-L-proline-L-asparagine-L-alanine-L-valine-amide (SEQ ID NO:41) B1 are taken up in 5 ml of DMF. 0.35 ml (3.32 mmol) of diethylamine are added and the mixture is stirred at room temperature for 15 minutes. The mixture is filtered off with suction through a clarifying layer and concentrated under high vacuum. The solid residue is triturated with diethyl ether and filtered off with suction.

Yield: 141 mg (81%).

2.2.3 Methyl tert-butyl succinate (B3).

Under argon, 13.2 g (100 mmol) of monomethyl succinate are suspended in 500 ml of methylene chloride. Over a period of 30 minutes, 12.9 ml (150 mmol) of oxalyl chloride are added dropwise, and the mixture is subsequently stirred at room temperature for 6 hours. After approximately 3.5 hours, a clear solution results. 300 ml of tert-butanol are subsequently added dropwise. The mixture is then allowed to stand at room temperature for 21 hours, and the clear solution is concentrated. The residue is dissolved in ethyl acetate and washed with $H_2O$, $NaHCO_3$ solution and $H_2O$. The solution is dried with $Na_2SO_4$ and concentrated.

Yield: 21.6 g (crude oil-like product).

2.2.4 Mono tert-butyl succinate (B4)

9.4 g (50 mmol) of methyl tert-butyl succinate (B3) are dissolved in 115 ml of 1,4-dioxane. 110 ml of 0.5N NaOH are subsequently added. The mixture is allowed to stand at room temperature, and product precipitates out. The mixture is allowed to stand at room temperature over the weekend and is subsequently concentrated. The aqueous solution is extracted using diethyl ether. The aqueous phase is cooled to 0° C. and acidified to pH 4 using cold 2N $H_2SO_4$. The mixture is subsequently extracted five times using diethyl ether. The organic phases are combined, washed with $H_2O$, dried with $Na_2SO_4$ and concentrated. Yield: 5.62 g of an oil (64.5%).

2.2.5 N-tert-Butyl-succinyl-trans-3-(2'-naphthyl)-L-proline-L-asparagine-L-alanine-L-valine-amide (SEQ ID NO:41) (B5)

262 mg (0.5 mmol) of trans-3-(2'-naphthyl)-L-proline-L-asparagine-L-alanine-L-valine-amide (SEQ ID NO:41) (B2), 87.1 mg (0.5 mmol) of mono-tert-butyl succinate (B4) and 67.5 mg of HOBt are dissolved in 5 ml of DMF. At 0° C., 110 mg of DCC are added and the mixture is stirred at 0° C. for 1 hour and then at room temperature for 2 hours and allowed to stand at room temperature overnight. The precipitate is filtered off with suction and the filtrate is concentrated under high vacuum. The residue is triturated with $NaHCO_3$ solution, filtered off with suction, washed with $H_2O$ and dried in a desiccator.

Yield: 169 mg (49.6%).

2.2.6 N-Succinyl-trans-3-(2'-naphthyl)-L-proline-L-asparagine-L-alanine-L-valine-amide (SEQ ID NO:41) (34)

316 mg of N-tert-butyl-succinyl-trans-3-(2'-naphthyl)-L-proline-L-asparagine-L-alanine-L-valine-amide (SEQ ID NO:41) (B5) are dissolved in 2 ml of 90% strength trifluoroacetic acid and allowed to stand at room temperature for 1 hour. The mixture is subsequently filtered through a clarifying layer and concentrated. The residue is triturated with diethyl ether and filtered off with suction. This gives 159 mg of crude product. For .purification, the substance is chromatographed over Sephadex® LH20 using a butanol/glacial acetic acid/water mixture.

Yield: 27.5 mg (9.5%). m/z: 625.298949 (M+H)+ (high resolution mass spectrum).

NMR data of compound 34: (SEQ ID NO: 41)

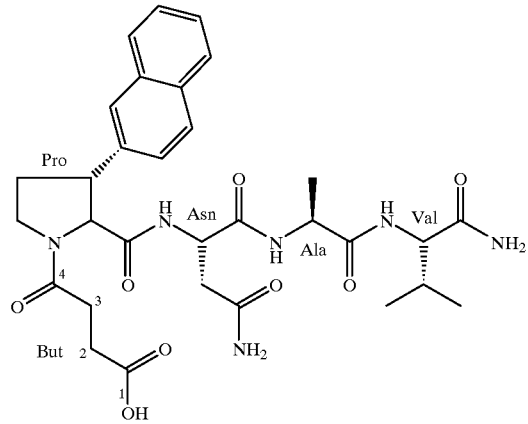

Chemical shifts of compound 34 in DMSO at 300 K.:

| See formula above | $^1$H trans | $^1$H cis | $^{13}$C trans | $^{13}$C cis |
|---|---|---|---|---|
| But-1 | — | — | 173.88 | 173.92 |
| But-2 | 2.54/2.46 | 2.61/2.20 | 28.64 | 28.37 |
| But-3 | 2.70/2.54 | 2.56/2.39 | 28.80 | 28.80 |
| But-4 | — | — | 170.67 | 170.22 |
| Pro-α | 4.39 | 4.68 | 66.18 | 65.46 |
| Pro-C' | — | — | 171.03 | 170.94 |
| Pro-β | 3.55 | 3.68 | 47.42 | 49.45 |
| Pro-γ | 2.40/2.16 | 2.33/1.94 | 32.02 | 30.41 |
| Pro-δ | 3.81/3.72 | 3.59/3.53 | 46.12 | 45.40 |
| Nap-1 | — | — | 138.79 | 139.55 |
| Nap-2 | 7.76 | 7.78 | 125.14 | 124.79 |
| Nap-2a | — | — | 132.97 | 132.97 |
| Nap-3 | 7.87 | 7.87 | 127.66 | 127.66 |
| Nap-4 | 7.49 | 7.49 | 126.03 | 126.03 |
| Nap-5 | 7.48 | 7.48 | 125.63 | 425.63 |
| Nap-6 | 7.88 | 7.88 | 127.33 | 127.33 |
| Nap-6a | — | — | 131.98 | 131.98 |
| Nap-7 | 7.87 | 7.89 | 127.97 | 127.97 |
| Nap-8 | 7.45 | 7.46 | 125.96 | 125.96 |
| Asn-NH | 8.31 | 8.50 | — | — |
| Asn-α | 4.44 | 4.64 | 50.13 | 49.79 |
| Asn-C' | — | — | 170.58 | 170.29 |
| Asn-β | 2.64/2.46 | 2.57/2.45 | 36.96 | 36.25 |
| Asn-γ-C' | — | — | 171.73 | 171.44 |
| Asn-δ-NH2 | 7.41/6.93 | 7.33/6.93 | — | — |

NMR data of compound 34: (SEQ ID NO: 41)

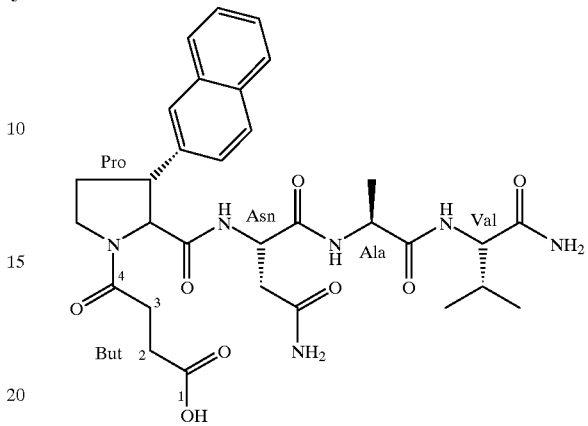

Chemical shifts of compound 34 in DMSO at 300 K.:

| See formula above | $^1$H trans | $^1$H cis | $^{13}$C trans | $^{13}$C cis |
|---|---|---|---|---|
| Ala-NH | 7.74 | 8.02 | — | — |
| Ala-α | 4.19 | 4.27 | 48.71 | 48.46 |
| Ala-C' | — | — | 171.84 | 171.78 |
| Ala-β | 1.22 | 1.19 | 17.49 | 18.04 |
| Val-NH | 7.48 | 7.70 | — | — |
| Val-α | 4.04 | 4.08 | 57.69 | 57.57 |
| Val-C' | — | — | 172.77 | 172.73 |
| Val-β | 1.97 | 1.97 | 30.08 | 30.29 |
| Val-γ | 0.82 | 0.86 | 19.24 | 19.27 |
| Val-γ' | 0.82 | 0.84 | 17.89 | 17.97 |
| Val-NH2 | 7.15/6.99 | 7.27/7.00 | — | — |

2.3 N-Succinyl-L-(2-naphthyl)alaninly-L-asparaginyl-L-serinyl-L-valinyl-glycine-3-hydroxypropylamide (SEQ ID NO:31) (24)

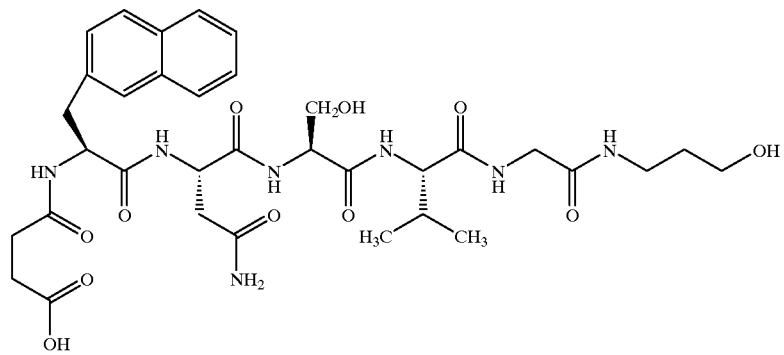

2.3.1 Benzyloxycarbonyl-glycine-(3-propanol)amide (C1)

627 g (30 mmol) of Gly-OH, 2.45 ml of 3-amino-1-propanol and 4.05 g of HOBt are dissolved in 60 ml of DMF. At 0° C., 6.6 g of DCC are added. The mixture is stirred at 0° C. for 1 hour and at room temperature for 3 hours and allowed to stand at room temperature overnight The precipitate is filtered off with suction and the filtrate is concentrated under high vacuum. The residue is partitioned between ethyl acetate and $NaHCO_3$ solution. The organic phase is then washed with $NaHCO_3$ solution and $H_2O$/NaCl, dried using $Na_2SO_4$ and concentrated. The residue is triturated with diethyl ether.

Yield: 7.05 g (88.2%).

2.3.2 Benzyloxycarbonyl-glycine-(3-propanol tert-butyl ester)amide (C2)

7 g (26.28 mmol) of benzyloxycarbonyl-glycine-(3-propanol)amide (C1) are dissolved in 60 ml of dioxane. At low temperature (liquid $CO_2$), 6 ml of $H_2SO_4$ are added slowly. Subsequently, 60 ml of condensed isobutylene are added. The mixture is shaken in an autoclave at room temperature and a nitrogen pressure of approximately 20 bar for 3 days. The mixture is then admixed with diethyl ether and extracted three times with 2N $Na_2CO_3$ solution. The aqueous solution is washed with diethyl ether. The organic phases are combined, washed with water, dried with $Na_2SO_4$ and concentrated.

Yield: 7.98 g (94.2%).

2.3.3 Glycine-(3-propanol tert-butyl ester)amide hydrochloride (C3)

7.98 g (24.75 mmol) of benzyloxycarbonyl-glycine-(3-propanol tert-butyl ester)amide (C2) are dissolved in 80 ml of MeOH, admixed with Pd/carbon and hydrogenated on an autotitrator using methanolic HCl and $H_2$. The catalyst is subsequently filtered off with suction and the filtrate is concentrated. The residue is dried under high vacuum.

Yield: 4.7 g (84.5%).

2.3.4 Benzyloxycarbonyl-L-valine-glycine-(3-propanol tert-butyl ester)amide (C4)

5.13 g (20.43 mmol) of benzyloxycarbonyl-Val-OH, 4.59 g (20.43 mmol) of glycine-(3-propanol tert-butyl ester) amide hydrochloride (C3) and 2.75 g of HOBt are dissolved in 60 ml of DMF. At 0° C., 2.65 ml of N-ethylmorpholine and 4.5 g of DCC are added. The mixture is stirred at 0° C. for 1 hour and then at room temperature for 2 hours. The mixture is allowed to stand at room temperature overnight and then concentrated under high vacuum. The residue is partitioned between glacial acetic acid and $NaHCO_3$ solution. The glacial acetic acid phase is then washed with $NaHCO_3$ solution, $KHSO_4$ solution and $H_2O$/NaCl, dried using $Na_2SO_4$ and concentrated. The solid residue is triturated with diethyl ether and filtered off with suction.

Yield: 7.32 g (85%).

2.3.5 L-Valine-glycine-(3-propanol tert-butyl ester)amide hydrochloride (C5)

7.29 g (17.3 mmol) of benzyloxycarbonyl-L-valine-glycine-(3-propanol tert-butyl ester)amide (C4) are dissolved in 90 ml of MeOH, admixed with Pd/carbon and hydrogenated on an autotitrator using methanolic HCl. The catalyst is subsequently filtered off with suction and the filtrate is concentrated. The residue (amorphous) is dried under high vacuum, triturated with diethyl ether and filtered off with suction.

Yield: 5.22 g (93.2%).

2.3.6 Benzyloxycarbonyl-L-serine(tert-butyl ester)-L-valine-glycine-(3-propanol tert-butyl ester)amide (C6)

5.46 g (18.5 mmol) of Z-Ser(But)OH, 6 g (18.5 mmol) of L-valine-glycine-(3-propanol tert-butyl ester)amide hydrochloride (C5) and 2.5 g of HOBt are dissolved in 60 ml of DMF. At 0° C., 2.4 ml of N-ethylmorpholine and 4.07 g of DCC are added. The mixture is stirred at 0° C. for 1 hour and at room temperature for 3 hours. The mixture is allowed to stand at room temperature overnight and then concentrated under high vacuum. The solid residue is partitioned between glacial acetic acid and $NaHCO_3$ solution. The glacial acetic acid phase is washed with $NaHCO_3$ solution, $KHSO_4$ solution and $H_2O$/NaCl, dried using $Na_2SO_4$ and concentrated. The residue is triturated with diethyl ether and filtered off with suction.

Yield: 9.74 g (93.2%).

2.3.7 L-Serine(tert-butyl ester)-L-valine-glycine-(3-propanol tert-butyl ester) amide hydrochloride (C7)

9.74 g (17.25 mmol) of benzyloxycarbonyl-L-serine(tert-butyl ester)-L-valine-glycine-(3-propanol tert-butyl ester) amide (C6) are dissolved in approximately 100 ml of MeOH, admixed with Pd/carbon and hydrogenated on an autotitrator using methanolic HCl. The catalyst is subsequently filtered off with suction and the filtrate is concentrated. The residue (amorphous) is dried under high vacuum and subsequently triturated with diethyl ether and filtered off with suction.

Yield: 8.02 g (99.6%).

2.3.8 Benzyloxycarbonyl-L-asparagine-L-serine(tert-butyl ester)-L-valine-glycine-(3-propanol tert-butyl ester)amide (SEQ ID NO:52) (C8)

4.53 g (17 mmol) of Z-Asn-OH, 7.94 g of L-serine(tert-butyl ester)-L-valine-glycine-(3-propanol tert-butyl ester) amide hydrochloride (C7) and 2.3 g of HOBt are dissolved in 60 ml of DMF. At 0° C., 2.21 ml of N-ethylmorpholine and 3.74 g of DCC are added. The mixture is stirred at 0° C. for 1 hour and at room temperature for 3 hours and then concentrated under high vacuum. The residue is partitioned between pentanol and $NaHCO_3$ solution. The pentanol phase is washed with $NaHCO_3$ solution, $KHSO_4$ solution and $H_2O$/NaCl, dried over $Na_2SO_4$ and filtered off with suction, and the filtrate is concentrated under high vacuum. The residue is triturated with diethyl ether, cooled and filtered off with suction. The product is dried in a desiccator over $P_2O_5$.

Yield: 10.8 g (93.6%).

2.3.9 L-Asparagine-L-serine(tert-butyl ester)-L-valine-glycine-(3-propanol tert-butyl ester)amide hydrochloride (SEQ ID NO:52) (C9)

10.8 g (15.9 mmol) of benzyloxycarbonyl-L-asparagine-L-serine(tert-butyl ester)-L-valine-glycine-(3-propanol tert-butyl ester)amide (SEQ ID NO:52) (C8) are dissolved in approximately 160 ml of warm MeOH, admixed with Pd/carbon and hydrogenated on an autotitrator using methanolic HCl. The catalyst is subsequently filtered off with suction and the filtrate is concentrated. The amorphous residue is dried under high vacuum, triturated with diethyl ether, cooled and filtered off with suction.

Yield: 8.96 g (97%).

2.3.10 Benzyloxycarbonyl-L-2-naphthylalanine-L-asparagine-L-serine(tert-butyl ester)-L-valine-glycine-(3-propanol tert-butyl ester)amide (SEQ ID NO:53) (C10)

5.24 g (15 mmol) of benzyloxycarbonyl-2-Nal-OH, 8.72 g (15 mmol) of L-asparagine-L-serine(tert-butyl ester)-L-valine-glycine-(3-propanol tert-butyl ester)amide hydrochloride (SEQ ID NO:52) (C9) and 2.04 g of HOBt are dissolved in 60 ml of DMF. At 0° C., 1.95 ml of N-ethylmorpholine and 3.3 g of DCC are added. The mixture is stirred at 0° C. for 1-hour and at room temperature for 3 hours. The mixture is then allowed to stand at room temperature overnight, diluted with DMF and heated slightly. The precipitate is subsequently filtered off with suction and the filtrate is concentrated under high vacuum. The residue is triturated with $NaHCO_3$ solution and filtered off with suction and is then triturated with $KHSO_4$ solution, filtered off with suction, triturated with $H_2O$, filtered off with suction and washed with $H_2O$ and dried in a desiccator over $P_2O_5$.

Yield: 13.25 g (>99%).

2.3.11 L-2-Naphthylalanine-L-asparagine-L-serine(tert-butyl ester)-L-valine-glycine-(3-propanol tert-butyl ester) amide hydrochloride (SEQ ID NO:53) (C11)

8.85 g (10.1 mmol) of benzyloxycarbonyl-L-2-naphthylalanine-L-asparagine-L-serine(tert-butyl ester)-L-valine-glycine-(3-propanol tert-butyl ester)amide (SEQ ID NO:53) (C10) are partly dissolved in 270 ml of MeOH, admixed with Pd/carbon and hydrogenated on an autotitrator using methanolic HCl. The suspension is diluted with DMF. After approximately 6 hours, the mixture is concentrated to half its original volume. All the material dissolves. The mixture is allowed to stand at room temperature overnight. The catalyst is subsequently filtered off with suction and the filtrate is diluted with the same amount of MeOH, admixed with new catalysts (Pd/carbon) and hydrogenated further on the autotitrator. After 7 hours, the mixture is allowed to stand at room temperature overnight. The mixture is subsequently hydrogenated for another 4 hours, the catalyst is filtered off with suction and the filtrate is concentrated. The residue (amorphous) is dried under high vacuum and subsequently triturated with diethyl ether and filtered off with suction.

Yield: 7.56 g (96.2%).

2.3.12 N-tert-Butyl-succinyl-L-2-naphthylalanine-L-asparagine-L-serine-L-valine-glycine-(3-propanol)amide (SEQ ID NO:54) (C12)

523 mg (3 mmol) of L-2-naphthylalanine-L-asparagine-L-serine(tert-butyl ester)-L-valine-glycine-(3-propanol tert-butyl ester)amide hydrochloride (SEQ ID NO:53) (C11), 2.33 g of mono-tert-butyl succinate (B4) and 405 mg of HOBt are dissolved in 20 ml of DMF. At 0° C., 0.39 ml of N-ethylmorpholine and 660 mg of DCC are added. The mixture is stirred at 0° C. for 1 hour, at room temperature for 2 hours and then allowed to stand at room temperature overnight. The mixture is concentrated under high vacuum and the solid residue is triturated with $NaHCO_3$ solution and filtered off with suction. The product is subsequently triturated with $KHSO_4$ solution and filtered off with suction, washed with $H_2O$ and dried in a desiccator over $P_2O_5$.

Yield: 3.04 g (crude product).

2.3.13 N-Succinyl-L-2-naphthylalanine-L-asparagine-L-serine-L-valine-glycine-(3-propanol)amide (SEQ ID NO:54) (24)

3 g (crude product) of N-tert-butyl-succinyl-L-2-naphthylalanine-L-asparagine-L-serine-L-valine-glycine-(3-propanol)amide SEQ ID NO:54 (C12) are dissolved in 30 ml of 90% strength trifluoroacetic acid and allowed to stand at room temperature for 1 hour. The mixture is subsequently concentrated and the residue is triturated with diethyl ether and filtered off with suction. This gives 2.6 g of crude product. For purification, 250 mg of crude product are dissolved in warm glacial acetic acid and chromatographed over Sephadex LH20 using a butanol/glacial acetic acid/water mixture.

Yield: 103 mg m/z: 730.341246 $(M+H)^{+0}$ (high resolution mass spectrum).

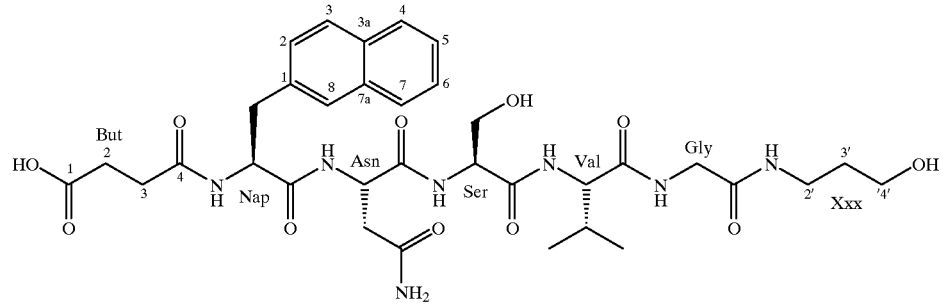

NMR data of compound 24: (SEQ ID NO: 54)

Chemical shifts of compound 24 in DMSO at 300 K.:

| See formula above | $^1H$ | $^{13}C$ |
|---|---|---|
| But-1 | — | 173.71 |
| But-2 | 2.29 | 28.99 |
| But-3 | 2.32/2.26 | 29.91 |
| But-4 | — | 171.15 |
| Nap-NH | 8.19 | — |
| Nap-α | 4.60 | 53.92 |
| Nap-C' | — | 171.20 |
| Nap-β | 3.19/2.91 | 37.56 |
| Nap-1 | — | 135.62 |
| Nap-2 | 7.42 | 127.85 |
| Nap-3 | 7.80 | 127.30 |
| Nap-3a | — | 131.75 |
| Nap-4 | 7.85 | 127.38 |
| Nap-5 | 7.44 | 125.31 |
| Nap-6 | 7.47 | 125.83 |
| Nap-7 | 7.82 | 127.38 |

-continued

NMR data of compound 24: (SEQ ID NO: 54)

Chemical shifts of compound 24 in DMSO at 300 K.:

| See formula above | $^1$H | $^{13}$C |
|---|---|---|
| Nap-7a | — | 132.91 |
| Nap-8 | 7.73 | 127.38 |
| Asn-NH | 8.35 | — |
| Asn-α | 4.60 | 49.73 |
| Asn-C' | — | 170.92 |
| Asn-β | 2.60/2.49 | 37.03 |
| Asn-γ-C' | — | 171.73 |
| Asn-δ-NH2 | 7.44/6.99 | — |
| Ser-NH | 7.89 | — |
| Ser-α | 4.33 | 55.15 |
| Ser-C' | — | 170.13 |
| Ser-β | 3.66/3.56 | 61.52 |
| Ser-OH | 4.93 | — |
| Val-NH | 7.82 | — |
| Val-α | 4.10 | 58.37 |
| Val-C' | — | 171.02 |
| Val-β | 2.04 | 29.91 |
| Val-γ | 0.86 | 19.17 |
| Val-γ' | 0.86 | 18.11 |
| Gly-NH | 8.06 | — |
| Gly-α | 3.65 | 41.97 |
| Gly-C' | — | 168.45 |
| Xxx-NH | 7.63 | — |
| Xxx-2' | 3.10 | 35.78 |
| Xxx-3' | 1.54 | 32.24 |
| Xxx-4' | 3.40 | 58.33 |
| Xxx-4'-OH | 4.40 | — |

3. Inhibition of laminin/nidogen interaction and biological activity

Unless expressly stated, the chemicals used were purchased from Merck (Darmstadt), Sigma (Munich) or Riedel de Haën (Seelze).

The isolation of laminin P1 from human placenta, human nidogen from transfected HEK-293 cells and mouse laminin γ1III 3–5 from HEK-293 cells is described in WO 98/31709.

Example 3.1

Inhibition Assays—Inhibition of Laminin/nidogen Binding with the Peptide Derivatives Found 3.1.1. HTS screening assay (highly sensitive assay variant):

Time-Resolved Fluorescence Assay

Coating of test tubes

Microtiter plates (for example FluoroNunc®) were coated with 75 μl of a 0.1 μg/ml solution of laminin P1 (in 0.159 g of $Na_2CO_3$, 0.293 g of $NaHCO_3$, 0.02 g of $NaN_3$/liter, pH 9.2) at room temperature for 1 hour. The solution was then tipped off, and free binding sites were blocked by incubation with 0.5% BSA (in 7.9 g of NaCl, 1.2 g of $Na_2HPO_4$, 0.31 g of KCl, 0.23 g of $NaH_2PO_4$, 0.04% Tween 20/liter, pH 7.2) at room temperature for 0.5 hour. Completion of the blocking reaction was followed by decantation of the solution and washing once with 250 μl of washing buffer (PBS/0.04% Tween).

Sequential inhibition

In parallel with the coating, a preincubation of 85–100 μl of a 0.25 nM nidogen solution (recombinantly produced human nidogen) with inhibitor or standard was carried out in a separate reaction vessel (1 hour at room temperature in 7.9 g of NaCl, 1.2 g of $Na_2HPO_4$, 0.31 g of KCl, 0.23 g of $NaH_2PO_4$, 0.04% Tween 20/liter, 0.5% BSA, pH 7.2). 75 μl of the preincubation (nidogen+inhibitor or standard) were transferred into the coated wells of the microtiter plate and incubated at room temperature for 1 hour. This was followed by washing twice with PBS/0.04% Tween.

Detection of the bound nidogen took place by incubation (at room temperature) for 1 hour with 75 μl of a specific antibody preparation obtained from yolks of eggs from a chicken immunized with human nidogen. The IgY fraction was used in a dilution of 1:500 in PBS/0.04% Tween. The complex of nidogen and specifically bound antibodies was, after washing twice with PBS/0.04% Tween, detected by adding anti-chicken IgY-biotin (75 μl of a 1:2500 dilution; Promega, Madison, Wis. 53711, 608-274-4330). An incubation time of 1 hour and washing twice with PBS/0.04% Tween were followed for this purpose by incubation with streptavidin-europium (Wallac; 1 hour at room temperature) and washing twice with PBS/0.04% Tween. It was finally possible, after adding 100 μl of enhancement solution (Wallac) and shaking for 5 minutes, to measure a fluorescence signal in a Victor multilabel counter using the europium protocol. The relation between the amount, of bound nidogen in the solutions with inhibitor and that of nidogen without added inhibitor was found.

3.1.2. Three-day equilibrium assay

Selected inhibitors were investigated for inhibitory activity in this assay variant. The assay is described in U.S. Pat. No. 5,493,008.

The following table compares IC50 values of selected substances with the results of the HTS screening assay. It is clear that the 3-day assay gives slightly lower measured values and, as expected, is more sensitive than the screening assay. However, it is also clear from the comparison that inhibitory structures can be identified reliably with the screening assay developed by us.

TABLE 2

Characterization of specific inhibitors of the laminin/nidogen association; IC50 values (μM) in the various assay variants

| Structure | HTS assay | 3-day equilibrium assay |
| --- | --- | --- |
| NIDPNAV (SEQ ID NO:1) | 3.9 | 1.2 |
| DPNAV (SEQ ID NO:51) | 7.7 | 5.0 |
| Compound 24 | 0.36 | 0.09 |
| Compound 31 | 0.19 | 0.085 |

Example 3.2 (hypothetical)

Testing the biological activity of the peptide derivatives

Several models which are described in detail in the literature can be used to test the biological activity of the peptide derivatives.

Some representative ones are mentioned below:

Formation of tubuli in cultures of embryonic kidneys.
Grobstein, C.; (1956) Exp. Cell Res. 10: 424–440.
Ekblom, P. et al. (1994) Development 120: 2003–2014

Branching morphology in embryonic lungs.
Ekblom, P. et al. (1994) Development 120: 2003–2014

Branching morphology in embryonic salivary glands.
Grobstein, C. (1953) J. Exp. Zool.124: 383–413
Kadoya, Y. et al. (1997) Development 124: 683–691

Basement membrane assembly in a organotypic skin culture.
Smola, H.; Stark, H.-J.; Thiekötter, G.; Mirancea, N.; Krieg, T.; Fusenig, N. E. (1998) Exp. Cell Res. 239: 399–410

Reconstitution of hydra from disintegrated cells.
Yang, Y. G.; Mayura, K.; Spainhour, C. B.; Edwards Jr., J. F.; Phillips, T. D. (1993) Toxicology 85: 179–198

Thickening of basement membranes in hydra after culturing at increased glucose concentration.
Zhang, X.; Huff, J. K.; Hudson, B. G.; Sarras Jr.; M. P. (1990) Diabetologia 33: 704–707

All types of quantitative angiogenesis assays summarized in a review article by Jain, R. K. et al. in Nature Medicine (1997) Vol. 3, No. 11, for example:

Induction of Haemangiomes in mice by implantation of cells from spontaneous hemangioendotheliomes.
O'Reilly, M. S.; Brem, M. S.; Folkman, J. (1995) J. Pediatr. Surg. 30:2; 325–329

Growth of micro-vessels in a serum-free culture of rat aorta.
Nicosia, R. F.; Ottinetti, A. (1990) Lab. Invest Vol.63, No. 1, 115–122

Formation of capillaries of endothelic cells on microcarriers after imbedding into a fibrin gel.
Nehis, V.; Drenckhahn, D. (1995) Microvascular Research 50: 311–322.

---

We claim:
1. A compound of formula I

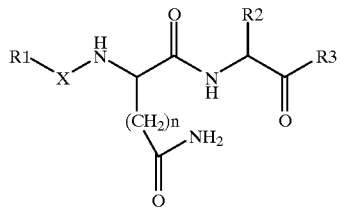
(I)

in any stereoisomeric form,
or a physiologically tolerable salt thereof,
or a mixture thereof,
wherein
R1 is

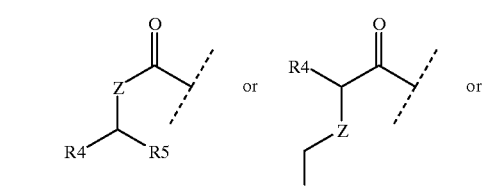

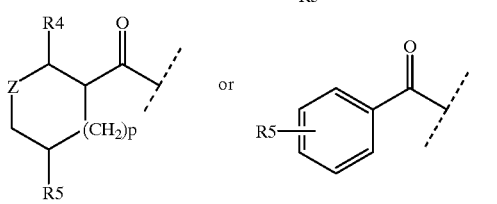

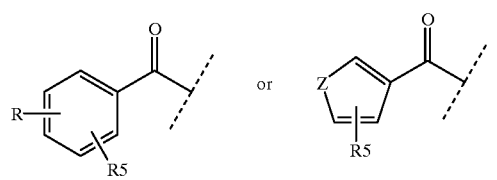

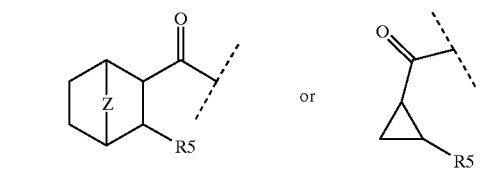

wherein
R4 is —A, —NH₂, —NHR, —NR₂,

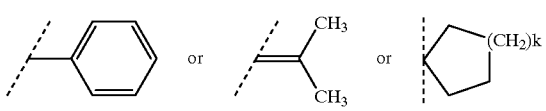

and R5 is —(CH₂)$_t$COOA, —(CH₂)$_t$CONH₂, —(CH₂)$_t$NH₂, —(CH₂)$_t$—SO₃H,

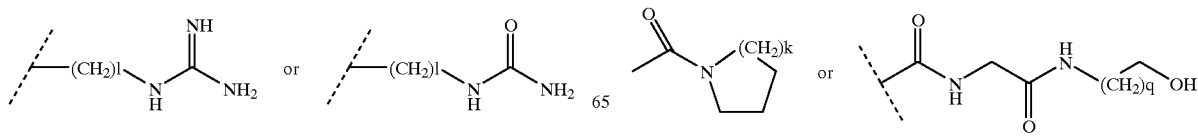

X is

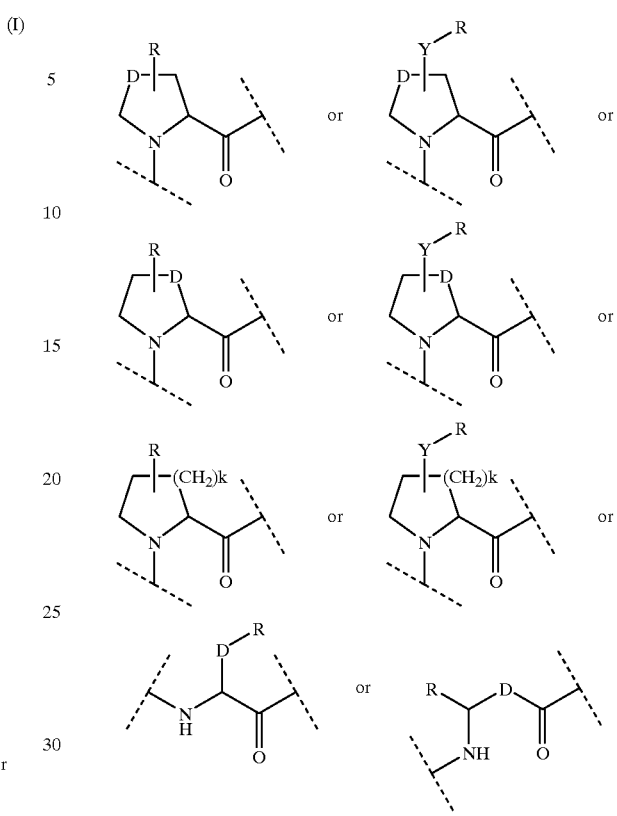

wherein
Y is O, S, —N(A)—CO— or —(CH₂)$_r$—,
D is (CH₂)$_r$, O, S, NH, NR, (CH₂)$_r$—O, (CH₂)$_r$—S, (CH₂)$_r$—NH or (CH₂)$_r$NR and R2 is —E—OH, —E—COOH or —E—CONH₂,
wherein E is a linear or branched $C_1$–$C_{10}$-alkyl chain, which is unsubstituted or substituted by —A, —(CH₂)$_m$—OH, —(CH₂)$_m$—COOH, —(CH₂)$_m$—C(O)NA₂ or by a $C_5$–$C_{10}$-cycloalkyl group,
or E is $C_5$–$C_{10}$-cycloalkyl, which is unsubstituted or substituted by —A, —(CH₂)$_m$—OH, —(CH₂)$_m$—COOH, —(CH₂)$_m$—C(O)NA₂ or by a $C_5$–$C_{10}$-cycloalkyl group, R3 is

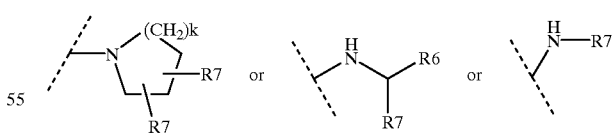

wherein R6 is —H, —COOH, —CONH₂, —CONHR, —CONR₂, —CH₂OH or

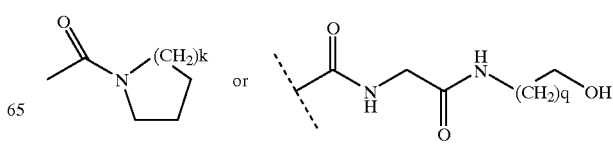

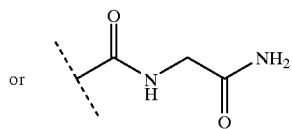 or and wherein R7 is a linear or branched $C_1$–$C_{10}$-alkyl group, which is unsubstituted or substituted by —A, —$(CH_2)_m$—OH, —$(CH_2)_m$—COOH, —$(CH_2)_m$—C(O)NA$_2$ or by a $C_5$–$C_{10}$-cycloalkyl group, or R7 is a $C_5$–$C_{10}$-cycloalkyl group, which is unsubstituted or substituted by —A, —$(CH_2)_m$—OH, —$(CH_2)_m$—COOH, —$(CH_2)_m$—C(O)NA$_2$ or by a $C_5$–$C_{10}$-cycloalkyl group, and R is branched or unbranched $C_1$–$C_6$-alkyl, $C_2$–$C_6$-alkenyl, $C_2$–$C_6$-alkynyl, $C_5$–$C_{10}$-cycloalkyl, Het or Ar which are unsubstituted or substituted by one or more halogen, $C_1$–$C_6$-alkyloxy, branched or unbranched $C_1$–$C_6$-alkyl, $C_2$–$C_6$-alkenyl, $C_2$–$C_6$-alkynyl or $C_5$–$C_{10}$-cycloalkyl groups or by —$C_1$–$C_6$-alkyl-Het, —$C_1$–$C_6$-alkyl-Ar, —O—$C_1$–$C_6$-alkyl-Het, —O—$C_1$–$C_6$-alkyl-Ar, Het or by Ar, wherein Het is a monocyclic or bicyclic, 5- to 10-membered aromatic or non-aromatic ring containing 1 or 2 equal or different hetero-atoms as members of said ring, the heteroatoms being selected from the group consisting of nitrogen, oxygen and sulfur, which ring is unsubstituted or substituted by one or more hydroxy or carboxy groups, and wherein Ar is a monocyclic or bicyclic 5- to 10-membered aromatic ring which is unsubstituted or substituted by one or more hydroxy or carboxy groups, Z is $(CH_2)_m$, O, S, NH, NR, N—C(O)—R or NSO$_2$R, A is H or $C_1$–$C_4$-alkyl l, m and r are each independently integers from 0 to 3, n and k are each independently integers from 1 to 2, p is an integer from 0 to 1 and q is an integer from 1 to 3.

2. A compound as claimed in claim 1, wherein n is 1.

3. A compound as claimed in claim 1, wherein R in group X is Het or Ar which are unsubstituted or substituted by —$C_1$–$C_6$-alkyl-Het, —$C_1$–$C_6$-alkyl-Ar, —O—$C_1$–$C_6$-alkyl-Het, —O—$C_1$–$C_6$-alkyl-Ar, Het or by Ar.

4. A compound as claimed in claim 3, wherein R in group X is Het and Het is

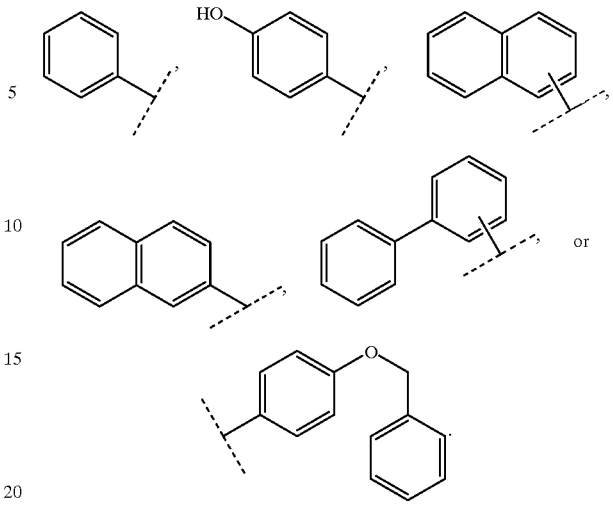

5. A compound as claimed in claim 3, wherein R in group X is Ar and Ar is

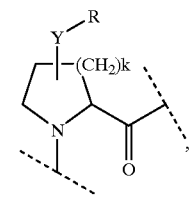

6. A compound as claimed in claim 1, wherein X is a group of the formula

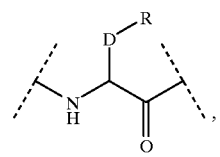

wherein Y is —$(CH_2)_r$— and r is 0 or 1.

7. A compound as claimed in claim 1, wherein X is a group of the formula

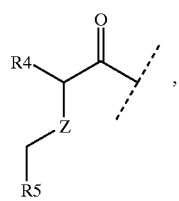

wherein D is —$(CH_2)_r$— and r is 0 or 1.

8. A compound as claimed in claim 1, wherein R1 is a group of the formula wherein Z is $(CH_2)_m$, m is 0 or 1, R5 is —$(CH_2)_r$—COOH or —$(CH_2)_r$—CONH$_2$, and R4 is —NH$_2$ or H, and l is 0.

9. A compound as claimed in claim 1, wherein R1 is a group of the formula

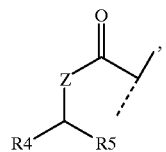

wherein Z is —(CH$_2$)$_m$—, m is 1, R4 is —NH$_2$, R5 is —(CH$_2$)$_l$—COOH, and l is 0.

10. A compound as claimed in claim 1, wherein R1 is a group of the formula

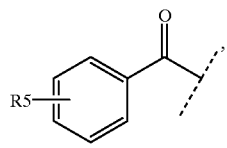

wherein R5 is —(CH$_2$)$_l$—COOH and l is 0.

11. A compound as claimed in claim 1, wherein R2 is —CH$_2$—COOH, or —CH$_2$—OH.

12. A compound as claimed in claim 1, wherein R3 is a group of the formula

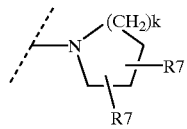

and k is 2.

13. A compound as claimed in claim 1, wherein R3 is

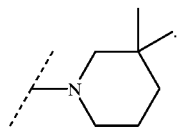

14. A compound as claimed in claim 1, wherein R3 is a group of the formula

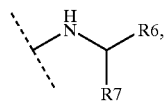

wherein
R7 is —CH(CH$_3$)$_2$, —C(CH$_3$)$_3$, —CH(CH$_3$)CH$_2$—CH$_3$, or —CH$_2$—CH(CH$_3$)$_2$, and
R6 is —H, —COOH, —CONH$_2$, —CH$_2$OH, —CON(CH$_3$)$_2$, or

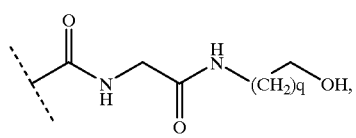

wherein q is 2.

15. A compound as claimed in claim 1, wherein R3 is a group of the formula

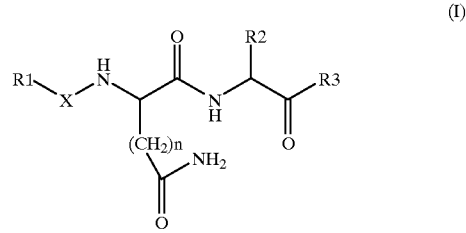

wherein R7 is —CH(CH$_3$)$_2$)$_2$ or —CH$_2$C(CH$_3$)$_3$.

16. A compound as claimed in claim 1, wherein R2 is —CH$_2$OH.

17. A compound of formula I (I)

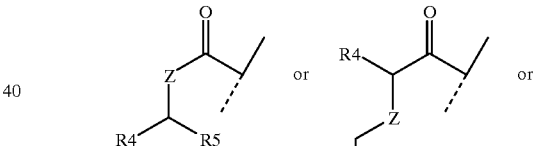

in any stereoisomeric form,
or a physiologically tolerable salt thereof,
or a mixture thereof, wherein R1 is

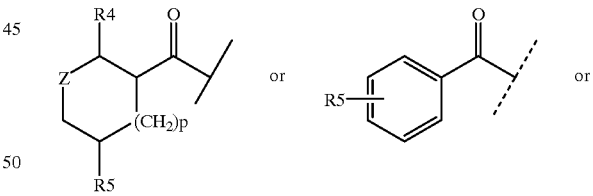

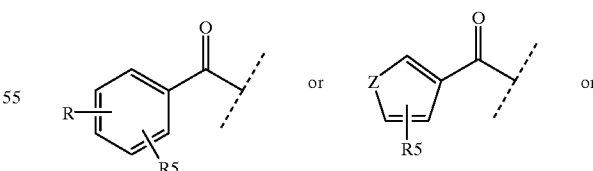

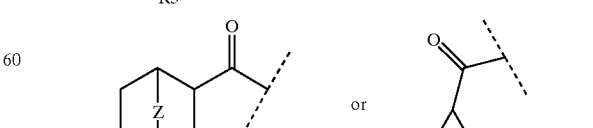

wherein

R4 is —A, —NH$_2$, —NHR, —NR$_2$,

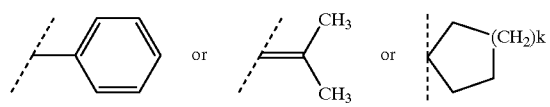

and R5 is —(CH$_2$)$_l$COOA, —(CH$_2$)$_l$CONH$_2$, —(CH$_2$)$_l$NH$_2$, —(CH$_2$)$_l$—SO$_3$H,

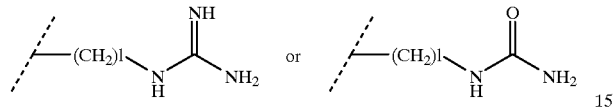

X is

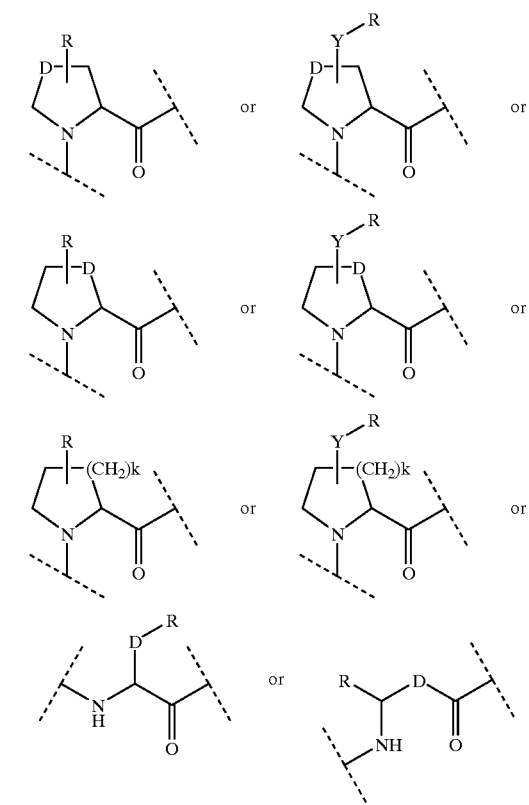

wherein
Y is O, S, —N(A)—CO— or —(CH$_2$)$_r$—,
D is (CH$_2$)$_r$, O, S, NH, NR, (CH$_2$)$_r$—O, (CH$_2$)$_r$—S, (CH$_2$)$_r$—NH or (CH$_2$)$_r$NR and
R2 is —CH$_3$,
R3 is

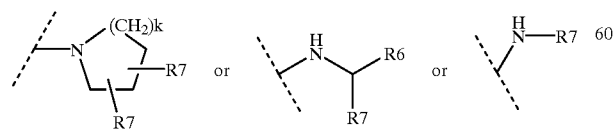

wherein R6 is —H, —COOH, —CONH$_2$, —CONHR, —CONR$_2$, —CH$_2$OH or

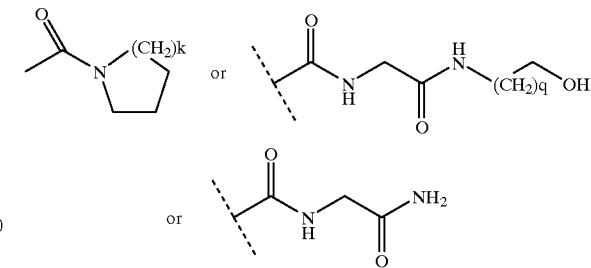

and wherein R7 is a linear or branched C$_1$–C$_{10}$-alkyl group, which is unsubstituted or substituted by —A, —(CH$_2$)$_m$—OH, —(CH$_2$)$_m$—COOH, —(CH$_2$)$_m$—C(O)NA$_2$ or by a C$_5$–C$_{10}$-cycloalkyl group, or R7 is a C$_5$–C$_{10}$-cycloalkyl group, which is unsubstituted or substituted by —A, —(CH$_2$)$_m$—OH, —(CH$_2$)$_m$—COOH, —(CH$_2$)$_m$—C(O)NA$_2$ or by a C$_5$–C$_{10}$-cycloalkyl group, and R is branched or unbranched C$_1$–C$_6$alkyl, C$_2$–C$_6$-alkenyl, C$_2$–C$_6$-alkynyl, C$_5$–C$_{10}$-cycloalkyl, Het or Ar which are unsubstituted or substituted by one or more halogen, C$_1$–C$_6$-alkyloxy, branched or unbranched C$_1$–C$_6$-alkyl, C$_2$–C$_6$-alkenyl, C$_2$–C$_6$-alkynyl or C$_5$–C$_{10}$-cycloalkyl groups or by —C$_1$–C$_6$-alkyl-Het, —C$_1$–C$_6$-alkyl-Ar, —O—C$_1$–C$_6$-alkyl-Het, —O—C$_1$–C$_6$-alkyl-Ar, Het or by Ar, wherein Het is a monocyclic or bicyclic, 5- to 10-membered aromatic or non-aromatic ring containing 1 or 2 equal or different hetero-atoms as members of said ring, the heteroatoms being selected from the group consisting of nitrogen, oxygen and sulfur, which ring is unsubstituted or substituted by one or more hydroxy or carboxy groups, and wherein Ar is a monocyclic or bicyclic 5- to 10-membered aromatic ring which is unsubstituted or substituted by one or more hydroxy or carboxy groups, Z is (CH$_2$)$_m$, O, S, NH, NR, N—C(O)—R or NSO$_2$R, A is H or C$_1$–C$_4$-alkyl l, m and r are each independently integers from 0 to 3, n and k are each independently integers from 1 to 2, p is an integer from 0 to 1 and q is an integer from 1 to 3.

18. A compound as claimed in claim 1, wherein R1 is

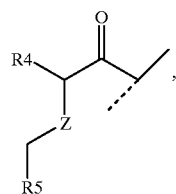

and wherein R4 is H; Z is (CH$_2$)$_m$, where m is 0; and R5 is —(CH$_2$)$_l$COOA, where l is 0 and A is H.

19. A compound as claimed in claim 1, wherein X is

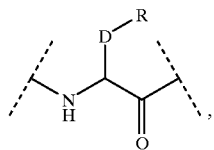

wherein D is (CH$_2$)$_r$ and r is 1; and R is

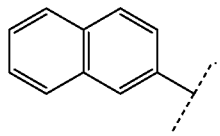

20. A compound as claimed in claim 1, wherein X is

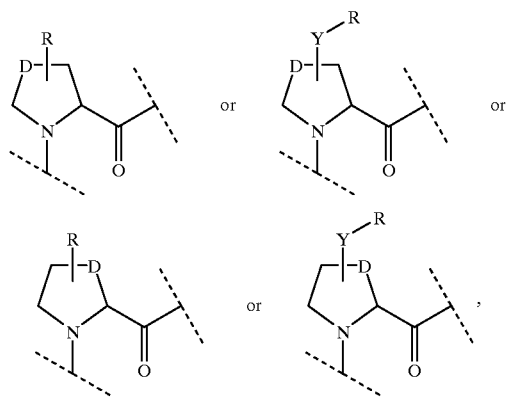

21. A compound as claimed in claim 1, wherein R3 is

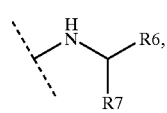

and wherein R6 is

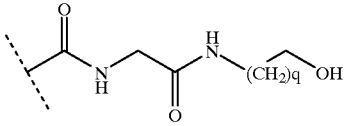

where q is 2, and R7 is —(CH)CH$_3$CH$_3$.

22. A compound as claimed in claim 1, wherein R3 is

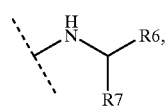

and wherein R6 is —CONH$_2$ and R7 is —(CH)CH$_3$CH$_3$.

23. A compound as claimed in claim 1, wherein the compound is

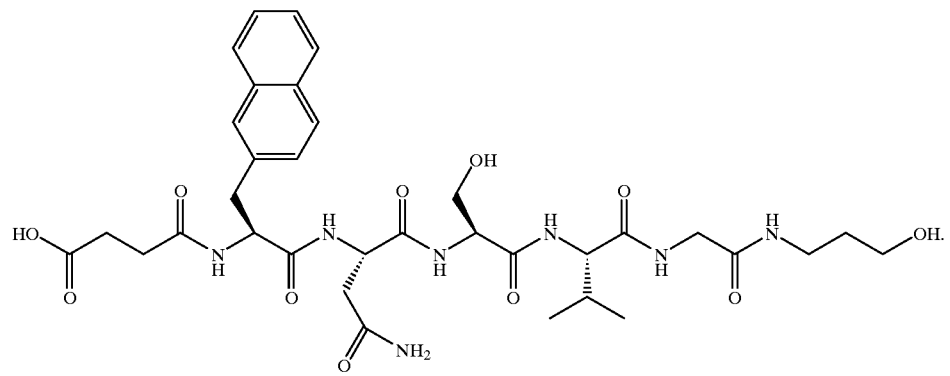

wherein D and Y are both (CH$_2$)$_r$, r is 0; and R is

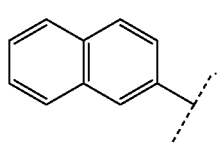

24. A compound of the formula

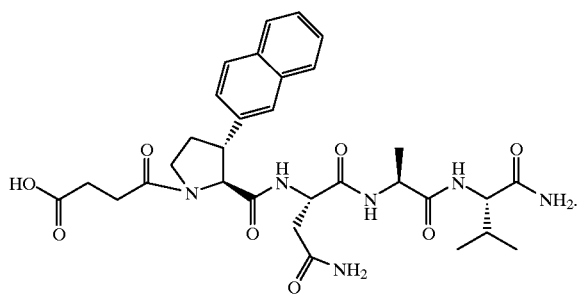

25. A pharmaceutical composition, comprising at least one compound as claimed in claim 1 and at least one pharmaceutically acceptable excipient.

26. A method for the treatment of a disease which is related to an increased or unwanted synthesis of basement membranes, which comprises administering to a host in need of the treatment an effective amount of at least one compound as claimed in claim 1.

27. A method as claimed in claim 26, wherein the disease is a late complication of diabetes mellitus; atherosclerosis; cancer; diabetic retinopathia; fibroplasia retrolentalis; or psoriasis.

28. A method as claimed in claim 26, wherein the disease is a fibrosis accompanied by an increased synthesis of basement membranes or their components.

29. A method as claimed in claim 28, wherein the disease is a fibrosis of the liver.

30. A method as claimed in claim 26, wherein the disease is related to a strong inflammatory component.

31. A method as claimed in claim 30, wherein the disease is rheumatoic arthritis; osteoarthritis; or vasculitis.

32. A method as claimed in claim 26, wherein the disease is related to haemangiomes.

33. A method for identifying a compound that inhibits the interaction of laminin and nidogen, which comprises measuring the inhibition of the compound together with a compound as claimed in claim 1 as a competitive inhibitor.

34. A method as claimed in claim 33, wherein the compound to be identified is formulated in a pharmaceutical acceptable form.

* * * * *

UNITED STATES PATENT AND TRADEMARK OFFICE
CERTIFICATE OF CORRECTION

PATENT NO.    : 6,365,572 B1
DATED         : April 2, 2002
INVENTOR(S)   : Hanz Ulrich Stilz et al.

It is certified that error appears in the above-identified patent and that said Letters Patent is hereby corrected as shown below:

Column 109,
Lines 1-9, in the structural formula

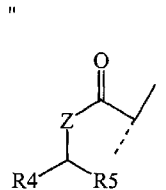    should read    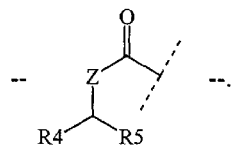

Column 110,
In the first three structural formulae immediately following line 35

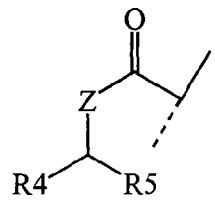 or 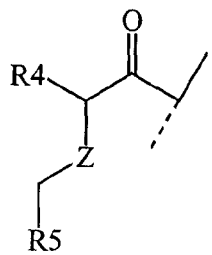 or 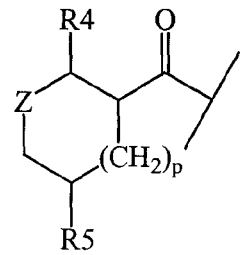

should read

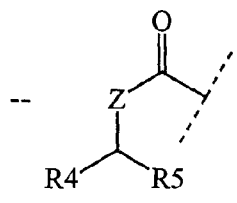 or 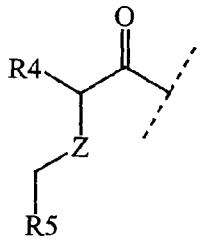 or 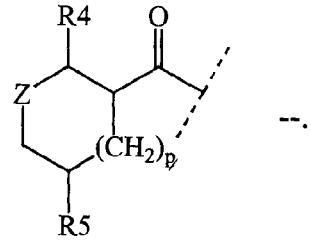

UNITED STATES PATENT AND TRADEMARK OFFICE
CERTIFICATE OF CORRECTION

PATENT NO. : 6,365,572 B1
DATED : April 2, 2002
INVENTOR(S) : Hanz Ulrich Stilz et al.

It is certified that error appears in the above-identified patent and that said Letters Patent is hereby corrected as shown below:

Column 112,
Line 23, "$C_1$-$C_6$alkyl" should read -- $C_1$-$C_6$-alkyl --.
In the structural formula immediately following line 53

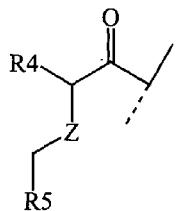   should read   -- 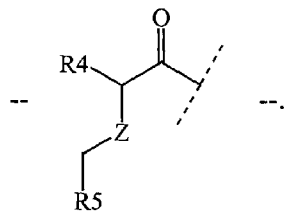 --.

Columns 113-114,
After the structural formula, insert -- (SEQ ID NO: 31) --.

Signed and Sealed this

Twenty-second Day of October, 2002

Attest:

Attesting Officer

JAMES E. ROGAN
*Director of the United States Patent and Trademark Office*

SEQUENCE LISTING

```
<160> NUMBER OF SEQ ID NOS: 54

<210> SEQ ID NO 1
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Ile Asp Pro Asn Ala Val
  1               5

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: Nal2
<221> NAME/KEY: MOD_RES
```

```
<222> LOCATION: (6)
<223> OTHER INFORMATION: G-Hopa

<400> SEQUENCE: 2

Asp Xaa Asn Asp Val Xaa
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: Nal2
<221> NAME/KEY: MOD_RES
<222> LOCATION: (6)
<223> OTHER INFORMATION: G-Hopa

<400> SEQUENCE: 3

Asp Xaa Asn Ala Val Xaa
 1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: Nal2
<221> NAME/KEY: MOD_RES
<222> LOCATION: (6)
<223> OTHER INFORMATION: G-Hopa

<400> SEQUENCE: 4

Asp Xaa Asn Asp Ile Xaa
 1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: Nal2
<221> NAME/KEY: MOD_RES
<222> LOCATION: (6)
<223> OTHER INFORMATION: G-Hopa

<400> SEQUENCE: 5

Asp Xaa Asn Ser Val Xaa
 1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: Nal2
```

```
<221> NAME/KEY: MOD_RES
<222> LOCATION: (6)
<223> OTHER INFORMATION: G-Hopa

<400> SEQUENCE: 6

Asp Xaa Asn Ser Ile Xaa
 1               5

<210> SEQ ID NO 7
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: Nal2
<221> NAME/KEY: MOD_RES
<222> LOCATION: (6)
<223> OTHER INFORMATION: G-Hopa

<400> SEQUENCE: 7

Asp Xaa Asn Ala Ile Xaa
 1               5

<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (8)
<223> OTHER INFORMATION: glycine-3-hydroxypropylamide

<400> SEQUENCE: 8

Asn Ile Asp Pro Asn Ala Val Xaa
 1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: glycine-3-hydroxypropylamide

<400> SEQUENCE: 9

Asp Pro Asn Ala Val Xaa
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: 3-(2-naphthyl)alanyl
<221> NAME/KEY: MOD_RES
<222> LOCATION: (6)
<223> OTHER INFORMATION: glycine-3-hydroxypropylamide

<400> SEQUENCE: 10
```

Asp Xaa Asn Asp Val Xaa
 1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: 3-(2-naphthyl)alanyl
<221> NAME/KEY: MOD_RES
<222> LOCATION: (6)
<223> OTHER INFORMATION: glycine-3-hydroxypropylamide

<400> SEQUENCE: 11

Asp Xaa Asn Ser Val Xaa
 1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: 3-(2-naphthyl)alanyl
<221> NAME/KEY: MOD_RES
<222> LOCATION: (6)
<223> OTHER INFORMATION: glycine-3-hydroxypropylamide

<400> SEQUENCE: 12

Asp Xaa Asn Ala Val Xaa
 1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: 3-(2-naphthyl)alanyl
<221> NAME/KEY: MOD_RES
<222> LOCATION: (6)
<223> OTHER INFORMATION: glycine-3-hydroxypropylamide

<400> SEQUENCE: 13

Asp Xaa Asn Asp Ile Xaa
 1               5

<210> SEQ ID NO 14
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: 3-(2-naphthyl)alanyl
<221> NAME/KEY: MOD_RES
<222> LOCATION: (6)
<223> OTHER INFORMATION: glycine-3-hydroxypropylamide -continued

```
<400> SEQUENCE: 14

Asp Xaa Asn Ser Ile Xaa
 1               5

<210> SEQ ID NO 15
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: 3-(2-naphthyl)alanyl
<221> NAME/KEY: MOD_RES
<222> LOCATION: (6)
<223> OTHER INFORMATION: glycine-3-hydroxypropylamide

<400> SEQUENCE: 15

Asp Xaa Asn Ala Ile Xaa
 1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: 3-(1-naphthyl)alanyl
<221> NAME/KEY: MOD_RES
<222> LOCATION: (6)
<223> OTHER INFORMATION: glycine-3-hydroxypropylamide

<400> SEQUENCE: 16

Asp Xaa Asn Ala Val Xaa
 1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: glycine-3-hydroxypropylamide

<400> SEQUENCE: 17

Asp Trp Asn Ala Val Xaa
 1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: glycine-3-hydroxypropylamide

<400> SEQUENCE: 18

Asp Phe Asn Ala Val Xaa
 1               5
```

```
<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (6)
<223> OTHER INFORMATION: glycine-3-hydroxypropylamide

<400> SEQUENCE: 19

Asp Tyr Asn Ala Val Xaa
 1               5

<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: 3-(3-benzothienyl)alanyl
<221> NAME/KEY: MOD_RES
<222> LOCATION: (6)
<223> OTHER INFORMATION: glycine-3-hydroxypropylamide

<400> SEQUENCE: 20

Asp Xaa Asn Ala Val Xaa
 1               5

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: 3-(4-biphenyl)alanyl
<221> NAME/KEY: MOD_RES
<222> LOCATION: (6)
<223> OTHER INFORMATION: glycine-3-hydroxypropylamide

<400> SEQUENCE: 21

Asp Xaa Asn Ala Val Xaa
 1               5

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: (3.3-diphenyl)alanyl
<221> NAME/KEY: MOD_RES
<222> LOCATION: (6)
<223> OTHER INFORMATION: glycine-3-hydroxypropylamide

<400> SEQUENCE: 22

Asp Xaa Asn Ala Val Xaa
 1               5

<210> SEQ ID NO 23
```

```
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: (3S)-phenylprolyl
<221> NAME/KEY: MOD_RES
<222> LOCATION: (6)
<223> OTHER INFORMATION: glycine-3-hydroxypropylamide

<400> SEQUENCE: 23

Asp Xaa Asn Ser Val Xaa
 1               5

<210> SEQ ID NO 24
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: (3R)-phenylprolyl
<221> NAME/KEY: MOD_RES
<222> LOCATION: (6)
<223> OTHER INFORMATION: glycine-3-hydroxypropylamide

<400> SEQUENCE: 24

Asp Xaa Asn Ser Val Xaa
 1               5

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: 3-(3-pyridyl)alanyl
<221> NAME/KEY: MOD_RES
<222> LOCATION: (6)
<223> OTHER INFORMATION: glycine-3-hydroxypropylamide

<400> SEQUENCE: 25

Asp Xaa Asn Ser Val Xaa
 1               5

<210> SEQ ID NO 26
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: (2-naphthyl)alanyl
<221> NAME/KEY: MOD_RES
<222> LOCATION: (6)
<223> OTHER INFORMATION: glycine-3-hydroxypropylamide

<400> SEQUENCE: 26

Asp Xaa Asn Ser Val Xaa
 1               5
```

```
<210> SEQ ID NO 27
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: homophenylalanyl
<221> NAME/KEY: MOD_RES
<222> LOCATION: (6)
<223> OTHER INFORMATION: glycine-3-hydroxypropylamide

<400> SEQUENCE: 27

Asp Xaa Asn Ser Val Xaa
 1               5

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: 3-(2-naphthyl)alanyl
<223> OTHER INFORMATION: C-term amidation

<400> SEQUENCE: 28

Asp Xaa Asn Ser Val Gly
 1               5

<210> SEQ ID NO 29
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: 3-(2-naphthyl)alanyl
<223> OTHER INFORMATION: C-term amidation

<400> SEQUENCE: 29

Asp Xaa Asn Ser Val
 1               5

<210> SEQ ID NO 30
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 3-(2-naphthyl)alanyl
<221> NAME/KEY: MOD_RES
<222> LOCATION: (5)
<223> OTHER INFORMATION: glycine-3-hydroxypropylamide

<400> SEQUENCE: 30

Xaa Asn Ser Val Xaa
 1               5

<210> SEQ ID NO 31
<211> LENGTH: 5
<212> TYPE: PRT
```

```
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 3-(2-naphthyl)alanyl
<221> NAME/KEY: MOD_RES
<222> LOCATION: (5)
<223> OTHER INFORMATION: glycine-3-hydroxypropylamide

<400> SEQUENCE: 31

Xaa Asn Ser Val Xaa
 1               5

<210> SEQ ID NO 32
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: B-Aspartyl
<221> NAME/KEY: MOD_RES
<222> LOCATION: (2)
<223> OTHER INFORMATION: 3-(2-naphthyl)alanyl
<221> NAME/KEY: MOD_RES
<222> LOCATION: (6)
<223> OTHER INFORMATION: glycine-3-hydroxypropylamide

<400> SEQUENCE: 32

Xaa Xaa Asn Ser Val Xaa
 1               5

<210> SEQ ID NO 33
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 3-(2-naphthyl)alanyl
<221> NAME/KEY: MOD_RES
<222> LOCATION: (5)
<223> OTHER INFORMATION: glycine-3-hydroxypropylamide

<400> SEQUENCE: 33

Xaa Asn Ser Val Xaa
 1               5

<210> SEQ ID NO 34
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: Citrulyl
<221> NAME/KEY: MOD_RES
<222> LOCATION: (3)
<223> OTHER INFORMATION: 3-(2-naphthyl)alanyl
<221> NAME/KEY: MOD_RES
<222> LOCATION: (7)
<223> OTHER INFORMATION: glycine-3-hydroxypropylamide

<400> SEQUENCE: 34
```

```
Xaa Asp Xaa Asn Ser Val Xaa
 1               5

<210> SEQ ID NO 35
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: 3-(2-naphthyl)alanyl
<221> NAME/KEY: MOD_RES
<222> LOCATION: (7)
<223> OTHER INFORMATION: glycine-3-hydroxypropylamide

<400> SEQUENCE: 35

Arg Asp Xaa Asn Ser Val Xaa
 1               5

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (3)
<223> OTHER INFORMATION: 3-(2-naphthyl)alanyl
<221> NAME/KEY: MOD_RES
<222> LOCATION: (7)
<223> OTHER INFORMATION: glycine-3-hydroxypropylamide

<400> SEQUENCE: 36

Lys Asp Xaa Asn Ser Val Xaa
 1               5

<210> SEQ ID NO 37
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 3-(2-naphthyl)alanyl
<221> NAME/KEY: MOD_RES
<222> LOCATION: (5)
<223> OTHER INFORMATION: glycine-3-hydroxypropylamide

<400> SEQUENCE: 37

Xaa Asn Ala Val Xaa
 1               5

<210> SEQ ID NO 38
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 3-(2-naphthyl)alanyl
<223> OTHER INFORMATION: C-term amidation

<400> SEQUENCE: 38

Xaa Asn Ala Val
```

```
<210> SEQ ID NO 39
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 3-(2-naphthyl)alanyl
<221> NAME/KEY: MOD_RES
<222> LOCATION: (4)
<223> OTHER INFORMATION: 2-tert-butyl-glycine
<223> OTHER INFORMATION: C-term amidation

<400> SEQUENCE: 39

Xaa Asn Ala Xaa
  1

<210> SEQ ID NO 40
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 3-(2-naphthyl)alanyl
<223> OTHER INFORMATION: C-term amidation

<400> SEQUENCE: 40

Xaa Asn Gly Val
  1

<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: (3R)-(2-naphthyl)prolyl
<223> OTHER INFORMATION: C-term amidation

<400> SEQUENCE: 41

Xaa Asn Ala Val
  1

<210> SEQ ID NO 42
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: O-benzyl-tyrosyl
<223> OTHER INFORMATION: C-term amidation

<400> SEQUENCE: 42

Xaa Asn Ala Val
  1

<210> SEQ ID NO 43
```

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 3-(4-biphenyl)alanyl
<223> OTHER INFORMATION: C-term amidation

<400> SEQUENCE: 43

Xaa Asn Ala Val
 1

<210> SEQ ID NO 44
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 3-(2-naphthyl)alanyl

<400> SEQUENCE: 44

Xaa Asn Ala Val
 1

<210> SEQ ID NO 45
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 3-(2-naphthyl)alanyl

<400> SEQUENCE: 45

Xaa Asn Ala Val
 1

<210> SEQ ID NO 46
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 3-(2-naphthyl)alanyl
<221> NAME/KEY: MOD_RES
<222> LOCATION: (3)
<223> OTHER INFORMATION: alanine-2,4-dimethylpentylamide

<400> SEQUENCE: 46

Xaa Asn Xaa
 1

<210> SEQ ID NO 47
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
```

```
<222> LOCATION: (1)
<223> OTHER INFORMATION: 3-(2-naphthyl)alanyl
<221> NAME/KEY: MOD_RES
<222> LOCATION: (3)
<223> OTHER INFORMATION: alanine-neopentylamide

<400> SEQUENCE: 47

Xaa Asn Xaa
 1

<210> SEQ ID NO 48
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 3-(2-naphthyl)alanyl
<221> NAME/KEY: MOD_RES
<222> LOCATION: (3)
<223> OTHER INFORMATION: alanine-3,3-dimethylpiperidinylamide

<400> SEQUENCE: 48

Xaa Asn Xaa
 1

<210> SEQ ID NO 49
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 3-(2-naphthyl)alanyl

<400> SEQUENCE: 49

Xaa Asn Ala Val
 1

<210> SEQ ID NO 50
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: (3R)-(2-naphthyl)prolyl

<400> SEQUENCE: 50

Xaa Asn Ala Val
 1

<210> SEQ ID NO 51
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

Asp Pro Asn Ala Val
 1               5
```

```
<210> SEQ ID NO 52
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (2)
<223> OTHER INFORMATION: serine(tert-butyl ester)
<221> NAME/KEY: MOD_RES
<222> LOCATION: (4)
<223> OTHER INFORMATION: glycine-(3-propanol tert-butyl ester)
<223> OTHER INFORMATION: C-term amidation

<400> SEQUENCE: 52

Asp Xaa Val Xaa
 1

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: L-2-naphthylalanine
<221> NAME/KEY: MOD_RES
<222> LOCATION: (3)
<223> OTHER INFORMATION: serine(tert-butyl ester)
<221> NAME/KEY: MOD_RES
<222> LOCATION: (5)
<223> OTHER INFORMATION: glycine-(3-propanol tert-butyl ester)
<223> OTHER INFORMATION: C-term amidation

<400> SEQUENCE: 53

Xaa Asp Xaa Val Xaa
 1               5

<210> SEQ ID NO 54
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<221> NAME/KEY: MOD_RES
<222> LOCATION: (1)
<223> OTHER INFORMATION: 2-naphthylalanine
<221> NAME/KEY: MOD_RES
<222> LOCATION: (5)
<223> OTHER INFORMATION: glycine-(3-propanol)
<223> OTHER INFORMATION: C-term amidation

<400> SEQUENCE: 54

Xaa Asp Ser Val Xaa
 1               5
```